United States Patent
Vogl et al.

(10) Patent No.: US 11,155,824 B2
(45) Date of Patent: Oct. 26, 2021

(54) EPISOMAL PLASMID VECTORS

(71) Applicant: bisy e.U., Hofstätten an der Raab (AT)

(72) Inventors: Thomas Vogl, Graz (AT); Anton Glieder, Gleisdorf (AT); Richard Wasmayer, Leoben (AT)

(73) Assignee: BISY E.U., Hofstätten an der Raab (AT)

(*) Notice: Subject to any disclaimer, the term of this patent is extended or adjusted under 35 U.S.C. 154(b) by 342 days.

(21) Appl. No.: 15/762,551

(22) PCT Filed: Sep. 29, 2016

(86) PCT No.: PCT/EP2016/073240
§ 371 (c)(1),
(2) Date: Mar. 22, 2018

(87) PCT Pub. No.: WO2017/055436
PCT Pub. Date: Apr. 6, 2017

(65) Prior Publication Data
US 2019/0078104 A1   Mar. 14, 2019

(30) Foreign Application Priority Data
Sep. 29, 2015 (EP) .................................. 15187431

(51) Int. Cl.
*C12N 15/81* (2006.01)
*C40B 50/06* (2006.01)

(52) U.S. Cl.
CPC ........... *C12N 15/815* (2013.01); *C12N 15/81* (2013.01); *C40B 50/06* (2013.01); *C12N 2800/108* (2013.01)

(58) Field of Classification Search
None
See application file for complete search history.

(56) References Cited

U.S. PATENT DOCUMENTS

2015/0011407 A1*  1/2015  Vogl ................... C12N 15/1086
                                                     506/9
2016/0097053 A1*  4/2016  Tolstorukov ......... C12N 15/815
                                                     435/196

FOREIGN PATENT DOCUMENTS

EP           2862933 A2     4/2015

OTHER PUBLICATIONS

Ahmad et al, "Protein expression in Pichia pastoris: recent achievements and perspectives for heterologous protein production", Appl Microbiol Biotechnol., 2014, 98(12):5301-5301.
Arenhart et al, "Use of homologous recombination in yeast to create chimeric bovine viral diarrhea virus cDNA clones", Brazilian J Microbiol, 2016, 47:993-999.
Astola et al, Isolation of Sparus auratus prolactin gene and activity of the cis-acting regulatory elements, Gen. Comp. Endocrinol., 2003, 134:57-61.
Camattari et al, "Characterization of a panARS-based episomal vector in the methylotrophic yeast Pichia pastoris for recombinant protein production and synthetic biology applications"; Microb Cell Fact, 2016, 15:139; 11 pages.
Chen et al, "Transcriptional terminators of RNA polymerase II are associated with yeast replication origins", Nucleic Acids Research, 24(15):2885-2893, 1996.
Cregg et al, "Expression in the Yeast Pichia pastoris", Methods in Enzymology, 2009, 463(09):169-189.
Curran et al, "Use of High Capacity Terminators in *Saccharomyces cerevisiae* to Increase mRNA half-life and Improve Gene Expression Control for Metabolic Engineering Applications", Metab Eng, 2013,19:88-97.
Gasser et al, "Pichia pastoris: protein production host and model organism for biomedical research", Future Microbiol., 2013, 8(2):191-208.
Gibson et al, "Enzymatic assembly of DNA molecules up to several hundred kilobases", Nat Methods, 2009, 6(5):343-345.
Hartner et al, "Promoter library designed for tine-tuned gene expression in Pichia pastoris", Nucleic Acids Res. Jul. 2008; 36(12), e76; 15 pages.
Hwang et al, "Isolation and characterisation of tilapia h-actin promoter and comparison of its activity with carp h-actin promoter", Biochim. Biophys. Acta, 2003, 1625:11-18.
Joska et al, "A universal cloning method based on yeast homologous recombination that is simple, efficient, and versatile", J Microbiol Methods, 2014,100(1):46-51.
Kim et al, "The skeletal muscle a-actin gene of channel catfish (*Ictalurus punctatus*) and its association with piscine specific SINE elements", Gene, 2000, 252:173-181.
Kuberl et al, "High-quality genome sequence of Pichia pastoris CBS7435", J Biotechnol., 2011,154(4):312-320.
Lee et al, "An episomal expression vector for screening mutant gene libraries in Pichia pastoris", Plasmid vol. 54(1):80-85 (2005).
Liachko et al, "A Comprehensive Genome-Wide Map of Autonomously Replicating Sequences in a Naive Genome", PLoS Genet., May 13, 2010;6(5):e1000946.
Liachko et al, "An autonomously replicating sequence for use in a wide range of budding yeasts", FEMS Yeast Res., 2014, 14(2):364-347.
Liachko et al, "High-resolution mapping, characterization, and optimization of autonomously replicating sequences in yeast", Genome Res., 2013, 23(4):698-704.
Liachko et al, "GC-Rlch DNA Elements Enable Replication Origin Activity in the Methylotrophic Yeast Pichia pastoris", PLoS Genet. Mar. 6, 2014;10(3):e1004169, 13 pages.

(Continued)

*Primary Examiner* — Channing S Mahatan
(74) *Attorney, Agent, or Firm* — Loza & Loza, LLP; Michael F. Fedrick

(57) ABSTRACT

An episomal plasmid comprising a gene of interest (GOI) and an autonomously replicating sequence (ARS) which is not operably linked to the GOI, which ARS comprises or consists of a nucleotide sequence identified as any of SEQ ID NO:2, SEQ ID NO:3, SEQ ID NO:5, or SEQ ID NO:6-11, or a functionally active variant of any of the foregoing which is characterized by at least 60% sequence identity thereto.

Figure 1A:
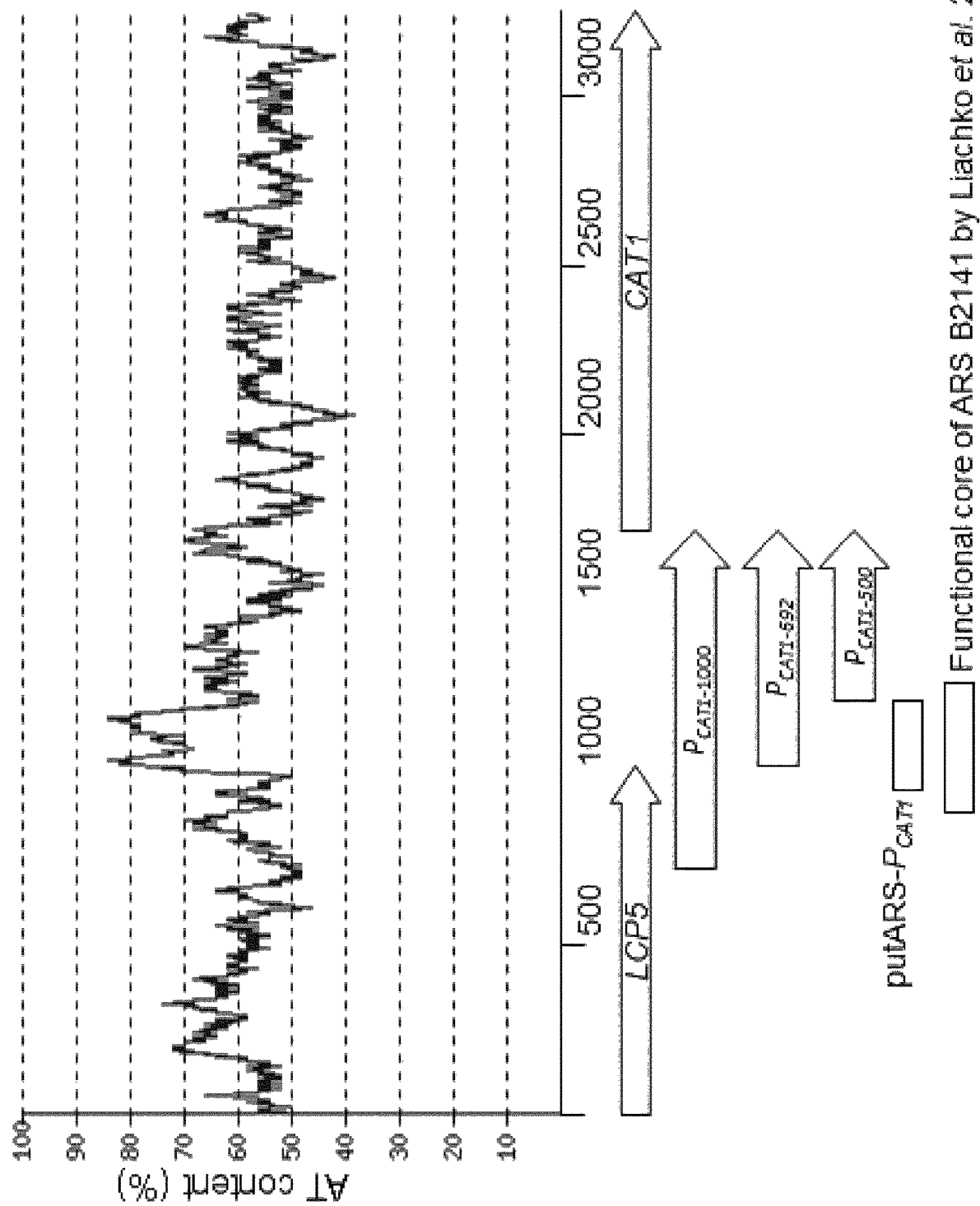

12 Claims, 39 Drawing Sheets
Specification includes a Sequence Listing.

(56) References Cited

OTHER PUBLICATIONS

Lin-Cereghino et al, "Condensed protocol for competent cell preparation and transformation of the methylotrophic yeast Pichia pastoris", Biotechniques., 2005, 38(1):44-48.
Naatsaari et al, "Deletion of the Pichia pastoris KU70 Homologue Facilitates Platform Strain Generation for Gene Expression and Synthetic Biology", PLoS One. 2012;7(6):e39720; 13 pages.
Oldenburg et al, "Recombination-mediated PCR-directed plasmid construction in vivo in yeast", Nucleic Acids Res., 1997, 25(2):451-452.
Orr-Weaver et al, "Yeast transformation: A model system for the study of recombination", Proc Natl Acad Sci USA, 1981, 78(10): 6354-6358.
Peng et al, "Recent advances in the genome-wide study of DNA replication origins of yeast", Front Microbiol. 2015, vol. 6, article 117, pp. 1-7.
Ruth et al, "Perspectives on Synthetic Promoters for Biocatalysis and Biotransformation", Chembiochem, 2010, 11(6):761-765.
Sohn et al, "A Novel Autonomously Replicating Sequence (ARS) for Multiple Integration in the Yeast Hansenula polymorpha DL-1", Journal of Bacteriology, 1996, 178(15):4420-4428.
Van Leeuwen et al, "Rapid and Efficient Plasmid Construction by Homologous Recombination in Yeast", Cold Spring Harb Protoc, 2015, pp. 853-861; doi:10.1101/pdb.prot085100.
Vina-Gonzalez et al, "Directed Evolution Method in *Saccharomyces cerevisiae*: Mutant Library Creation and Screening", J Vis Exp JoVE; 2016;(110):e53761; 7 pages.
Vogl et al, "Restriction site free cloning (RSFC) plasmid family for seamless, sequence independent cloning in Pichia pastoris", Microb Cell Fact. 2015, 14:103, 15 pages.
Vogl et al, "Regulation of Pichia pastoris promoters and its consequences for protein production", N Biotechnol., 2013, 30(4):385-404.
Vogl et al, "Synthetic Core Promoters for Pichia pastoris", ACS Synth. Biol., 2014, 3 (3): 188-191.
Vogl et al, "New opportunities by synthetic biology for biopharmaceutical production in Pichia pastoris", Current Opinion in Biotechnology, 2013, 24(6):1094-1101.
Weis et al, "Reliable high-throughput screening with Pichia pastoris by limiting yeast cell death phenomena", FEMS Yeast Res., 2004, 5(2):179-189.
Wiedner et al, "Discovery of a novel (R)-selective bacterial hydroxynitrile lyase from Acidobacterium capsulatum", Computational and Structural Biotechnology Journal, 2014, 10(16):58-62.
Yurimoto et al, "Characterization and High-level Production of D-Amino Acid Oxidase in Candida boidinii", Bioscience Biotechnology Biochemistry, 2001, 65 (3):627-633.
International Search Report for PCT/EP16/73240 dated Feb. 13, 2017; 10 pages.
Written Opinion for PCT/EP16/73240 dated Feb. 13, 2017; 10 pages.
Invitation to Pay Additional Fees and Partial International Search Report for PCT/EP16/73240 dated Jan. 2, 2017; 7 pages.
Extended European Search Report for EP15187431.0 dated Mar. 15, 2016; 10 pages.
Volckaert et al., Mol. Mar. Biol. Biotechnol., 1994, 3:57-69.
Kimihiko Mizutani, Biosci. Biotechnol. Biochem., 2015, 79(1):1-10.
Translation of Office Action in corresponding Japanese Patent Application No. 2018-517256 dated Jul. 21, 2020.

* cited by examiner

| Type of plasmid | Circular ARS ($P_{CAT1-692}$) | | | | Genomic integration ($P_{CAT1-500}$) | | | |
|---|---|---|---|---|---|---|---|---|
| Marker | GUT1 | | Zeocin | | GUT1 | | Zeocin | |
| GOI | MeHNL | LuHNL | MeHNL | LuHNL | MeHNL | LuHNL | MeHNL | LuHNL |
| Transformation efficiency (cfu/µg DNA) | 27500 | 40800 | 11900 | 88400 | 404 | 162 | 467 | 528 |
| MV±SD | 42150 ± 33018 | | | | 390 ± 160 | | | |

Fig. 8
A
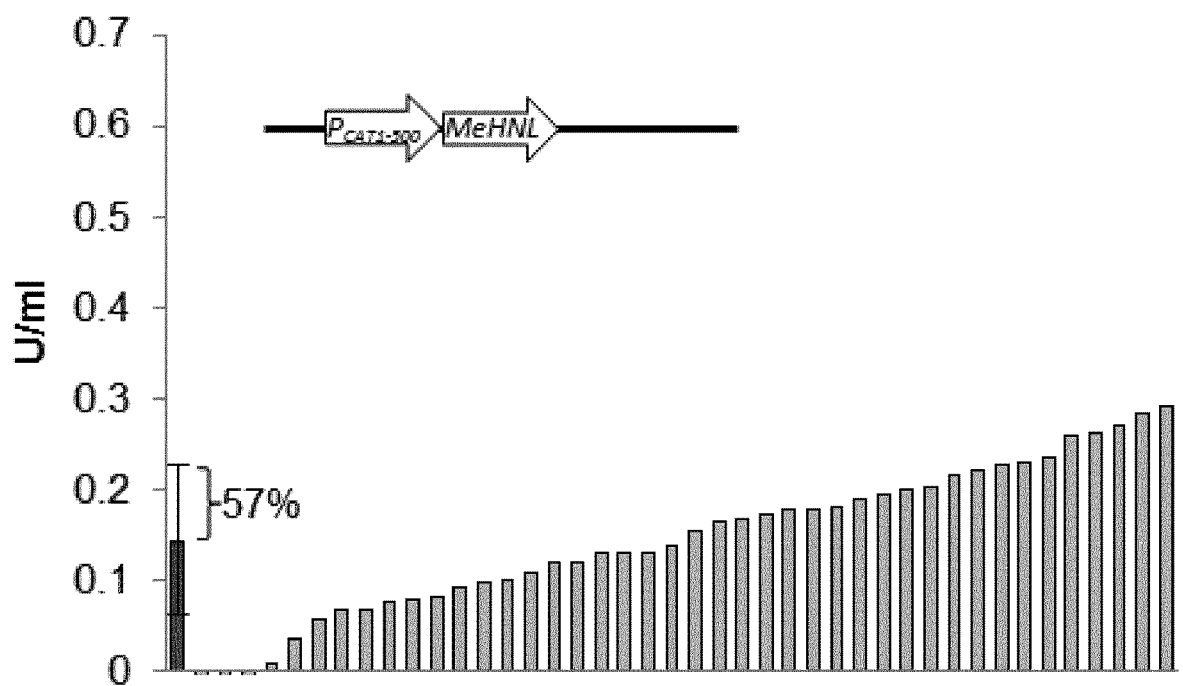
B
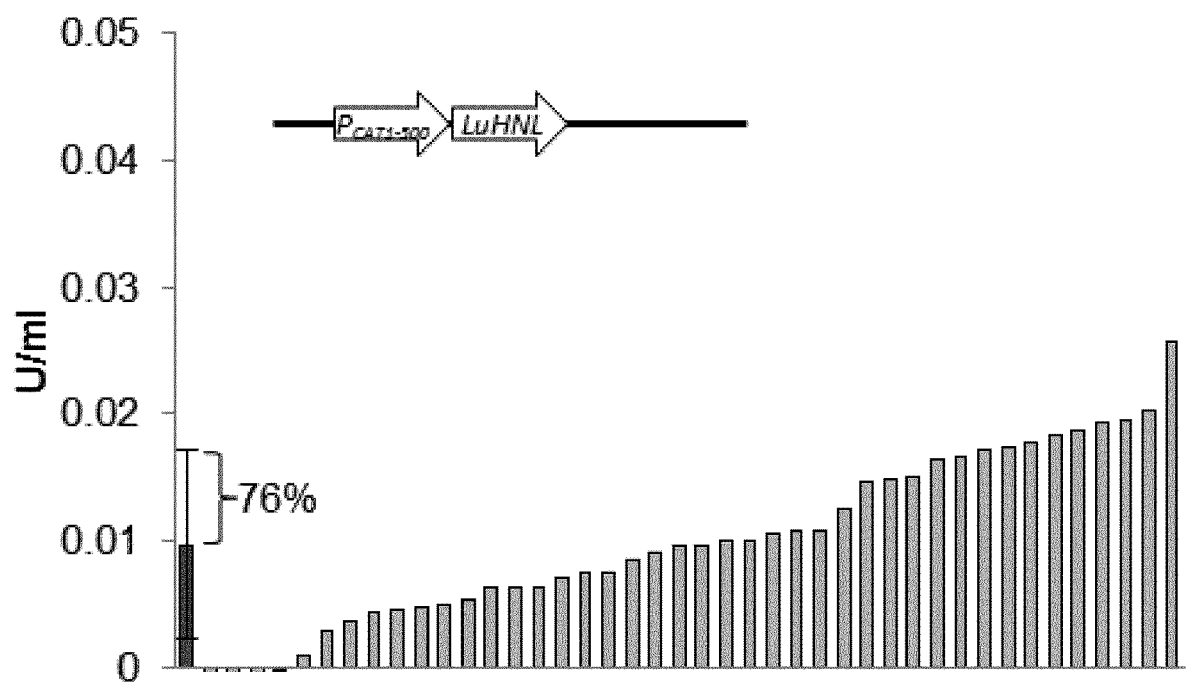

Fig. 9

Sequence of P$_{CAT1-692}$ (SEQ ID NO: 1)

agtgtgtaatcatatatataataaatgaggaataataattgaatagagatttaacgagtcgaagtttctgaaatatacgcac
agtttatatttatgattttgatatctaactacagtcttctccatatatttaactataaataataaagtatataactcttatgaaactgt
ttcaccacatttttttctacgtaatcgaactccgaatgcggttctcctgtaaccttaattgtagcatagatcacttaaataaactc
atggcctgacatctgtacacgttcttattggtcttttagcaatcttgaagtctttctattgttccggtcggcattacctaataaattc
gaatcgagattgctagtacctgatatcatatgaagtaatcatcacatgcaagttccatgatacctctactaatggaattga
acaaagtttaagcttctcgcacgagaccgaatccatactatgcaccctcaaagtgggattagtcaggaaagctgagc
aattaacttccctcgattggcctggacttttcgcttagcctgccgcaatcggtaagtttcattatcccagcggggtgatagcct
ctgttgctcatcaggccaaaatcatatataagctgtagacccagcacttcaattacttgaaattcaccataacacttgctcta
gtcaagacttacaattaaa

Fig. 10

Sequence of putARS-P$_{CAT}$ (SEQ ID NO: 2)

aaaagtgcgaggaagaataaaaatactgcttcctccgcctgggaaagagcaaaaagacgcagaggaaactaaagt
gtgtaatcatatatataataaatgaggaataataattgaatagagatttaacgagtcgaagtttctgaaatatacgcacagt
ttatatttatgattttgatatctaactacagtcttctccatatatttaactataaataataaagtatataactcttatgaaactgtttc
accacatttttttctacg

Fig.11

Sequence of P$_{CAT500-692}$ (SEQ ID NO:3)

agtgtgtaatcatatatataataaatgaggaataataattgaatagagatttaacgagtcgaagtttctgaaatatacgcac
agtttatatttatgattttgatatctaactacagtcttctccatatatttaactataaataataaagtatataactcttatgaaactgt
ttcaccacatttttttctacg

Fig. 12

Sequence of CAT1-500 promoter without ARS sequence (SEQ ID NO:4)

taatcgaactccgaatgcggttctcctgtaaccttaattgtagcatagatcacttaaataaactcatggcctgacatctgtac
acgttcttattggtcttttagcaatcttgaagtctttctattgttccggtcggcattacctaataaattcgaatcgagattgctagta
cctgatatcatatgaagtaatcatcacatgcaagttccatgatacctctactaatggaattgaacaaagtttaagcttctcg
cacgagaccgaatccatactatgcaccctcaaagtgggattagtcaggaaagctgagcaattaacttccctcgattgg
cctggacttttcgcttagcctgccgcaatcggtaagtttcattatcccagcggggtgatagcctctgttgctcatcaggccaa
aatcatatataagctgtagacccagcacttcaattacttgaaattcaccataacacttgctctagtcaagacttacaattaaa

Fig.13

Sequence of CbAOD1 Promoter ARS (SEQ ID NO:5)

GGAGTATACGTAAATATATAATTATATATAATCATATATATGAATACAATGCAATGA
AAGTGAATATGATAAGATTGAAATAATAACAAACAGCGATAAATATATCTCAAAATG
GAGTTACACAACAAATAATAATAAAATATAAATTATAAATTATAAATTATAAAAGAAT
AAAAAATAAACCCCACTAATTTATTTTATTAAAAGATAGATTGGTATCTTTACTTAAT
AACAATTCTGAAACTTTATTCACTTAATTTTATTTAACTTATTTAATTTATTTTACCC
CAGTTTTTCAGTACAATGCAGCTCCGAAACTTTATTTGGCTGTGATTTGGCTGTGA
TTTGGCTGTGATTTGGCTTGGCTTGGCTGGCTGGAATTGTCTCCTGCAGGAATTG
CTCGGGGTCCGGTTCTCCCGCTGGCTGGCTATTTGGCGGGCTGGCTATTTGGCG
GGCTGGCTGGCTGGCTGCTCTGCCATCTGCTGTGGCCACCCCGCATCTCTGGAT
GCACGCCGTGCAGCTGGACGTGCGTCTACCCTGCAGCCGTGTGCCTTATTTCCC
AATCTCCCAATCTCTCAATCTGCCAGTCAGCCAAAACACCGGCCAGGCAGGCAG
GCAGGCAGGCAGGCAGGCAGTGAAGCCTTCCCACGCCCACTCCGCATAAACAT
CCCCAGCAGTTTCCCCAGCAGTTTCCCCAGCTTTTCAATTTAATAAAATAGCCTGT
TTCTGTTTCTGTTTTATATTATACAATTTTTATCCTAATAATTACTCTTTCGGGAAT
TAAATAATAATTATATCATATACCCATATCACATTTTACTATATTTACTATCTATAAAT
AAATTCATATTATAATATTAATTTATATTCGCTTAATTAAAATGCTCTTTTCCATCAT
CATCATCATCATCATCACGAGTTTTCGGTTATCAATACTCTTTTCATTAATTTCT
AGAATTTCATTATTTATTTTTATTGACTGGAAATTTTCAATCAATTTTATTTATTTTT
ATTTATTTATTTTCATATTCTTAGATTTAAACTTTTTAGATGACCGCTATTTTACTTAC
TTACTTACTGTTGTTTATATTATGATAAGAATTAATTTTCATATTTATGATGATGAT
GATGTAAATTTAACCTAGTATACTATTTTAAAGTTATCACTATCTTTTAGTGCTGGC
ATTTTTTATTCTATTTTCATATATGTATATACGTAAATTAAGTATCATCACGCTGCTT
ACTGTACGTTTAAAATGTGGAGATGGAAATAGAGATGGGGATGAAGATGAAGATG
ATGAGAATTATAAACCATTCATTCATTAATCAATCAATATAACTTATAAAAAAATTTA
TATTTAAATGAATTAATTTCCTTTATTTTAATAATATCGTTAATTCTTTTAAATTCTAT
TTTATTTTAATTCTTTCTTTATCATAGTTATCATATAACAATTATATAACATAGATACA
CAATTATTATTTCATTATCATATTATTTTTTAAAATATTGATTATTTTTAAAATAATAT
CTTAATTAATTAATTTTTACGAATATACAAATTTTAACGACTTACTTTTTTTAACGAA
TTTTAACGAACTTTTAAAAAAACAAAAAAAAAAAAACAAAATTATTTTTCAATA

Figure 14

Sequence of AOD-F1 (SEQ ID NO:6)

GGAGTATACGTAAATATATAATTATATATAATCATATATATGAATACAATGCAATGA
AAGTGAATATGATAAGATTGAAATAATAACAAACAGCGATAAATATATCTCAAAATG
GAGTTACACAACAAATAATAATAAAATATAAATTATAAATTATAAATTATAAAAGAAT
AAAAAATAAACCCCACTAATTTATTTTATTAAAAGATAGATTGGTATCTTTACTTAAT
AACAATTCTGAAACTTTATTCACTTAATTTTATTTAACTTATTTAATTTATTTT

Figure 15

Sequence of AOD-F2 (SEQ ID NO:7)

TACCCCAGTTTTTCAGTACAATGCAGCTCCGAAACTTTATTTGGCTGTGATTTGGC
TGTGATTTGGCTGTGATTTGGCTTGGCTTGGCTGGCTGGAATTGTCTCCTGCAGG
AATTGCTCGGGGTCCGGTTCTCCCGCTGGCTGGCTATTTGGCGGGCTGGCTATT
TGGCGGGCTGGCTGGCTGGCTGCTCTGCCATCTGCTGTGGCCACCCCGCATCTC
TGGATGCACGCCGTGCAGCTGGACGTGCGTCTACCCTGCAGCCGTGTGCCTTAT
TTCCCAATCTCCCAATCTCTCAATCTGCCAGTCAGCCAAAACACCGGCCAGGCAG
GCAGGCAGGCAGGCAGGCAGGCAGTGAAGCCTTCCCACGCCCCACTCCGCA

Figure 16

Sequence of AOD-F3 (SEQ ID NO:8)

TAAACATCCCCAGCAGTTTCCCCAGCAGTTTCCCCAGCTTTTCAATTTAATAAAAT
AGCCTGTTTCTGTTTCTGTTTTATATTATACAATTTTTTATCCTAATAATTACTCTTT
CGGGAATTAAATAATAATTATATCATATACCCATATCACATTTTACTATATTTACTAT
CTATAAATAAATTCATATTATAATATTAATTTATATTCGCTTAATTAAAAT

Figure 17

Sequence of AOD-F4 (SEQ ID NO:9)

GCTCTTTTCCATCATCATCATCATCATCATCATCACGAGTTTTCGGTTATCAATACT
CTTTTCATTAATTTCTAGAATTTCATTATTTATTTTTTATTGACTGGAAATTTTCAATC
AATTTTATTTATTTTTATTTATTTATTTTCATATTCTTAGATTTAAACTTTTTAGATGA
CCGCTATTTTACTTACTTACTTACTGTTGTTTTATATTATGATAAGAATTAATTTTCA
TATTTATGATGATGATGATGTAAATTTAACCTAGTATACTATTTTAAAGTTATCACTA
TCTTTTAGTGCTGGCATTTTTTATTCTATTTTCATATATGTATATACGTAAATTAAGT
ATCATCA

Figure 18

Sequence of AOD-F5 (SEQ ID NO:10)

CGCTGCTTACTGTACGTTTAAAATGTGGAGATGGAAATAGAGATGGGGATGAAGA
TGAAGATGATGAGAATTATAAACCATTCATTCATTAATCAATCAATATAACTTATAA
AAAAATTTATATTTAAATGAATTAATTTCCTTTATTTTAATAATATCGTTAATTCTTTT
AAATTCTATTTTATTTTAATTCTTTCTTTATCATAGTTATCATATAACAATTATATAAC
ATAGATACACAATTATTATTTCATTATCATATTATTTTTTAAAATATTGATTATTTTTA
AAATAATATCTTAATTAATTAATTTTTACGAATATACAAATTTTAACGACTTACTTTTT
TTAACGAATTTTAACGAACTTTTAAAAAAACAAAAAAAAAAAAACAAAATTATTTTTC
AATA

Figure 19

Sequence of AOD-F6 (SEQ ID NO:11)

TAAACATCCCCAGCAGTTTCCCCAGCAGTTTCCCCAGCTTTTCAATTTAATAAAAT
AGCCTGTTTCTGTTTCTGTTTTATATTATACAATTTTTTATCCTAATAATTACTCTTT
CGGGAATTAAATAATAATTATATCATATACCCATATCACATTTTACTATATTTACTAT
CTATAAATAAATTCATATTATAATATTAATTTATATTCGCTTAATTAAAATGCTCTTTT
CCATCATCATCATCATCATCATCATCACGAGTTTTCGGTTATCAATACTCTTTTCAT
TAATTTCTAGAATTTCATTATTTATTTTTATTGACTGGAAATTTTCAATCAATTTTAT
TTATTTTTATTTATTTATTTTCATATTCTTAGATTTAAACTTTTTAGATGACCGCTATT
TTACTTACTTACTTACTGTTGTTTTATATTATGATAAGAATTAATTTTCATATTTATGA
TGATGATGATGTAAATTTAACCTAGTATACTATTTTAAAGTTATCACTATCTTTTAGT
GCTGGCATTTTTTATTCTATTTTCATATATGTATATACGTAAATTAAGTATCATCACG
CTGCTTACTGTACGTTAAAATGTGGAGATGGAAATAGAGATGGGGATGAAGATG
AAGATGATGAGAATTATAAACCATTCATTCATTAATCAATCAATATAACTTATAAAAA
AATTTATATTTAAATGAATTAATTTCCTTTATTTTAATAATATCGTTAATTCTTTTAAA
TTCTATTTTATTTTAATTCTTTCTTTATCATAGTTATCATATAACAATTATATAACATA
GATACACAATTATTATTTCATTATCATATTATTTTTTAAAATATTGATTATTTTTAAAA
TAATATCTTAATTAATTAATTTTTACGAATATACAAATTTTAACGACTTACTTTTTTTA
ACGAATTTTAACGAACTTTTAAAAAAACAAAAAAAAAAAAACAAAATTATTTTTCAAT
A

Figure 20

Sequence of pCAT1noCore (SEQ ID NO:12)

AGTGTGTAATCATATATATAATAAATGAGGAATAATAATTGAATAGAGATTTAACGA
GTCGAAGTTTCTGAAATATACGCACAGTTTATATTTATGATTTTGATATCTAACTAC
AGTCTTCTCCATATATTTAACTATAAATAATAAAGTATATAACTCTTATGAAACTGTT
TCACCACATTTTTTTCTACGTAATCGAACTCCGAATGCGGTTCTCCTGTAACCTTA
ATTGTAGCATAGATCACTTAAATAAACTCATGGCCTGACATCTGTACACGTTCTTAT
TGGTCTTTTAGCAATCTTGAAGTCTTTCTATTGTTCCGGTCGGCATTACCTAATAAA
TTCGAATCGAGATTGCTAGTACCTGATATCATATGAAGTAATCATCACATGCAAGT
TCCATGATACCCTCTACTAATGGAATTGAACAAAGTTTAAGCTTCTCGCACGAGAC
CGAATCCATACTATGCACCCCTCAAAGTTGGGATTAGTCAGGAAAGCTGAGCAAT
TAACTTCCCTCGATTGGCCTGGACTTTTCGCTTAGCCTGCCGCAATCGGTAAGTTT
CATTATCCCAGCGGGGTGATAGCCTCTGTTGCTCATCAGGCCAAAATCA

Figure 21

Sequence of SapI cloning stuffer (SEQ ID NO:13)

ATGAGAAGAGCGAATTCGGCGCGCCGGTAAGATCCAAATCGATGAATTGACCAA
GCACTACGGTATGAAGCCAGAAGACTACACTGCTGTCAGATGTGGTATGAATGTC
GCCAAGTACATCATCGAAGATAAGATTGATGCTGGTATTGGTATCGAATGTATGCA
ACAAGTCGAATTGGAAGAGTACTTGGCCAAGCAAGGCAGACCAGCTTCTGATGCT
AAAATGTTGAGAATTGACAAGTTGGCTTGCTTGGGTTGCTGTTGTTTCTGTACCGT
TCTTTACATCTGCAACGATGAATTTTGAAGAAAACCCTGAAAAGGTCAGAAAGT
TCTTGAAAGCCATCAAGAAGGCAACCGACTACGTTCTAGCCGACCCTGTGAAGGC
TTGGAAAGAATACATCGACTTCAAGCCTCAATTGAACAGCTCTTCATAA

Fig. 33

SEQ ID NO:72
ATTTAAATTTTTTGTAGAAATGTCTTGGTGTCCTCGTCCAATCAGGTAGCCATCTCTGAAATATCTGG
CTCCGTTGCAACTCCGAACGACCTGCTGGCAACGTAAAATTCTCCGGGGTAAAACTTAAATGTGGA
GTAATGGAACCAGAAACGTCTCTTCCCTTCTCTCTCCTTCCACCGCCCGTTACCGTCCCTAGGAAAT
TTTACTCTGCTGGAGAGCTTCTTCTACGGCCCCCTTGCAGCAATGTTCTTCCCAGCATTACGTTGCG
GGTAAAACGGAGGTCGTGTACCCGACCTAGCAGCCCAGGGATGGAAAAGTCCCGGCCGTCGCTG
GCAATAATAGCGGGCGGACGCATGTCATGAGATTATTGGAAACCACCAGAATCGAATATAAAAGGC
GAACACCTTTCCCAATTTTGGTTTCTCCTGACCCAAAGACTTTAAATTTAATTTATTTGTCCCTATTTC
AATCAATTGAACAACTATCAAAACACAATGAGAAGAGCGAATTCGGCGCGCCGGTAAGATCCAAAT
CGATGAATTGACCAAGCACTACGGTATGAAGCCAGAAGACTACACTGCTGTCAGATGTGGTATGAA
TGTCGCCAAGTACATCATCGAAGATAAGATTGATGCTGGTATTGGTATCGAATGTATGCAACAAGTC
GAATTGGAAGAGTACTTGGCCAAGCAAGGCAGACCAGCTTCTGATGCTAAAATGTTGAGAATTGAC
AAGTTGGCTTGCTTGGGTTGCTGTTGTTTCTGTACCGTTCTTTACATCTGCAACGATGAATTTTTGAA
GAAAAACCCTGAAAAGGTCAGAAAGTTCTTGAAAGCCATCAAGAAGGCAACCGACTACGTTCTAGC
CGACCCTGTGAAGGCTTGGAAAGAATACATCGACTTCAAGCCTCAATTGAACAGCTCTTCATAAGC
GGCCGCTCAAGAGGATGTCAGAATGCCATTTGCCTGAGAGATGCAGGCTTCATTTTTGATACTTTTT
TATTTGTAACCTATATAGTATAGGATTTTTTTTGTCATTTTGTTTCTTCTCGTACGAGCTTGCTCCTGA
TCAGCCTATCTCGCAGCAGATGAATATCTTGTGGTAGGGGTTTGGGAAAATCATTCGAGTTTGATGT
TTTTCTTGGTATTTCCCACTCCTCTTCAGAGTACAGAAGATTAAGTGAGACCTTCGTTTGTGCGGAT
CCTTCAGTAATGTCTTGTTTCTTTTGTTGCAGTGGTGAGCCATTTTGACTTCGTGAAAGTTTCTTTAG
AATAGTTGTTTCCAGAGGCCAAACATTCCACCCGTAGTAAAGTGCAAGCGTAGGAAGACCAAGACT
GGCATAAATCAGGTATAAGTGTCGAGCACTGGCAGGTGATCTTCTGAAAGTTTCTACTAGCAGATAA
GATCCAGTAGTCATGCATATGGCAACAATGTACCGTGTGGATCTAAGAACGCGTCCTACTAACCTT
CGCATTCGTTGGTCCAGTTTGTTGTTATCGATCAACGTGACAAGGTTGTCGATTCCGCGTAAGCAT
GCATACCCAAGGACGCCTGTTGCAATTCCAAGTGAGCCAGTTCCAACAATCTTTGTAATATTAGAGC
ACTTCATTGTGTTGCGCTTGAAAGTAAAATGCGAACAAATTAAGAGATAATCTCGAAACCGCGACTT
CAAACGCCAATATGATGTGCGGCACACAATAAGCGTTCATATCCGCTGGGTGACTTTCTCGCTTTAA
AAAATTATCCGAAAAAATTTTCTAGAGTGTTGTTACTTTATACTTCCGGCTCGTATAATACGACAAGG
TGTAAGGAGGACTAAACCATGGCTAAACTCACCTCTGCTGTTCCAGTCCTGACTGCTCGTGATGTT
GCTGGTGCTGTTGAGTTCTGGACTGATAGACTCGGTTTCTCCCGTGACTTCGTAGAGGACGACTTT
GCCGGTGTTGTACGTGACGACGTTACCCTGTTCATCTCCGCAGTTCAGGACCAGGTTGTGCCAGA
CAACACTCTGGCATGGGTATGGGTTCGTGGTCTGGACGAACTGTACGCTGAGTGGTCTGAGGTCG
TGTCTACCAACTTCCGTGATGCATCTGGTCCAGCTATGACCGAGATCGGTGAACAGCCCTGGGGTC
GTGAGTTTGCACTGCGTGATCCAGCTGGTAACTGCGTGCATTTCGTCGCAGAGGAACAGGACTAA
GGAGTATACGTAAATATATAATTATATATAATCATATATATGAATACAATGCAATGAAAGTGAATATGA
TAAGATTGAAATAATAACAAACAGCGATAAATATATCTCAAAATGGAGTTACACAACAAATAATAATA
AAATATAAATTATAAATTATAAATTATAAAAGAATAAAAAATAAACCCCACTAATTTATTTTATTAAAAG
ATAGATTGGTATCTTTACTTAATAACAATTCTGAAACTTTATTCACTTAATTTTATTTAACTTATTTAAT
TTATTTTATCCTTAGCGAAAGCTAAGGATTTTTTTAGGTACCACTGAGCGTCAGACCCCGTAGAAA
AGATCAAAGGATCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCGAAGGTAACTGG
CTTCAGCAGAGCGCAGATACCAAATACTGTTCTTCTAGTGTAGCCGTAGTTAGGCCACCACTTCAA
GAACTCTGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCGGTCGG
GCTGAACGGGGGGTTCGTGCACACAGCCCAGCTTGGAGCGAACGACCTACACCGAACTGAGATAC
CTACAGCGTGAGCTATGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGTATCTT
TATAGTCCTGTCGGGTTTCGCCACCTCTGACTTGAGCGTCGATTTTTGTGATGCTCGTCAGGGGGG
CGGAGCCTATGGAAAAACGCCAGCAACGCGGCCTTTTTACGGTTCCTGGCCTTTTGCTGGCCTTTT
GCTCACATGT

Fig. 33 continued

SEQ ID NO:85
AGATCCAATTCCCGCTTTGACTGCCTGAAATCTCCATCGCCTACAATGATGACATTTGGATTTGGTT
GACTCATGTTGGTATTGTGAAATAGACGCAGATCGGGAACACTGAAAAATACACAGTTATTATTCAT
TTAAATGACCCTTGTGACTGACACTTTGGGAGTCCCTATTCTACTTAGTCTCATATCGCATGAAACTT
TTGATAAATTATTTTCTGATAGGAATTTTTCATCAGATATTATCATCGCGGCTTACGTAATAACAAAAA
AAATTGATGGAGTCTATACTAGGCTAACATAAACTAAGTTATTAATTAAACAAAACAAAACGTACTAG
CATTACTGTCATATATAAGGGCTCCTAACTAAAACTGTAAAGACTTCCCGTGCGGCCGCCTACTTAC
CTGGGGACAAGCTCAATGATTTTTGAGTATAGTGGTTGTGCAATGCTTCGTGCATAACGGAACAAG
AGAAAACGTTTCCTTGTTGCCATCTAGATTTGTCTACAGTTAGCTTAGAATACAAGAAGAATGAACC
ATCAGAATCGAGGACTGGAGGGGTGGTTTTGTAGTTATTCTCAGGTTGTCCATTAGATTCCCATTCT
ACCGCGATATCTGAAGGGTAAAAACCTTTCACCAGACATGTTAGAGAAACTTGGTTTTTAGTCAGTT
CGTCCCTCGAAGGAGGCAATGTGTACACCTGAGGTTCACGTGGCTGACCCTTAGCTTTACTAATAG
TCTTTTCAATTGGAGCAGGCAGAGCTTTGTTGGATACCTTACACTTGTACTCCTTGCCGTTCAGCCA
GTCCTGGTGGAGAACAGTCAACACGCTCACTACTCTGTAGGTTGAATTATATTGCTCCTCTCTTGGT
TTGGTTTTAGCGTTATGGACTTCAACACCATCGACATACCAATTAAATTTCACTTCAGGATCCTCGTG
TGAAACGTCAACAACAACACATGTGACCTCTGGCGTTCTGCTGATCATAAGAGTGTCTTTTGGCTTG
GGCGGGAAAAGAAAGACTGAGGGACCACCTAACAGTTCAGGTGCTGGGCAAGGTGGACAAGTATG
GGTTTTGTCGCAACTCTTCGGTTCAACCTTTTTATCGACCTTTGTATTACTTGGCTTATGGTTAACAT
TACAAATGTATGTCTGAGTACCCAAGCTGGATGATGGCACAGTGACCACGGATGATAGGGAGTACA
ATCCTGAGCTTTGCAAAACGGCGGGGAATGTATGAACACCAGAAGTTAAAGCTCCACTATTCCACG
ACACAGTGACTGGTTCTGGGAAATAGTCTTTAACTAAACAACCCAAGGCAGCCGTACCACCGGATG
TAGACTTGGAAGAAGGTGCAAGAGGAAACACCGAGGGACCCTTTGTGGAAGCGGATGAAACTGTG
ACAAGTGTTCCTTGTCCCCAATAATCCATTGCGTAGAAACCATCACCACCCCATCGAGAACAATAAT
AGACAGCAGTGTCCTCAGCCCTCAGGCTATTCATCTGCAAGTAAGCAGTGTTTTTAGATGTATCAGC
AGAAATAGTAAATCTACCTTTAACACTATCGGCATATCTAGTATATCCATTAGTGGGGTATATTCTGG
CAACCCACTCCAAACCTTTACCAGGAGCTTGTCTAACCCAATGGATGTATGTGTCCTTGATGTTAAA
TCCGGAGGCAGCGCAGGACAATCTCAGGGATCCGCCAGGCTGCACTAGACCACCACCTGATTCTA
CCAGTTGCACCTCAGCTTCAGCCTCACGCTTTTCCAAAGACACGCCCTCTTCCTTTGCAGCAATTGA
TGCTATCGTAGTATTGATGAATAACAACCCATTATTCGTCGAATTACTGAATGGCAAAACAGCAACG
TCAAAGTCTCCCTCTAAATCGGAGTATCCGATTACAGCCTCTGCTGGGATTTGTGCGGTTTCATCCT
CTGTTGTAGTATTCACAGGGGCAGCTAATGCGGACGATGCTGCAAAAAGTACAGCGGTGAAAATAC
TTGGAAAACGCATTTTTGATGTTTGATAGTTTGATAAGAGTGAACTTTAGTGTTTAGAGGGGTTATAA
TTTGTTGTAACTGGTTTTGGTCTTAAGTTAAAACGAACTTGTTATATTAAACACAACGGTCACTCAGG
ATACAAGAATAGGAAAGAAAAACTTTAAACTGGGGACATGTTGTCTTTATATAATTTGGCGGTTAAC
CCTTAATGCCCGTTTCCGTCTCTTCATGATAACAAAGCTGCCCATCTATGACTGAATGTGGAGAAGT
ATCGGAACAACCCTTCACTAAGGATATCTAGGCTAAACTCATTCGCGCCTTAGATTTCTCCAAGGTA
TCGGTTAAGTTTCCTCTTTCGTACTGGCTAACGATGGTGTTGCTCAACAAAGGGATGGAACGGCAG
CTAAAGGGAGTGCATGGAATGACTTTAATTGGCTGAGAAAGTGTTCTATTTGTCCGAATTTCTTTTTT
CTATTATCTGTTCGTTTGGGCGGATCTCTCCAGTGGGGGGTAAATGGAAGATTTCTGTTCATGGGG
TAAGGAAGCTGAAATCCTTCGTTTCTTATAGGGGCAAGTATACTAAATCTCGGAACATTGAATGGGG
TTTACTTTCATTGGCTACAGAAATTATTAAGTTTGTTATGGGGTGAAGTTACCAGTAATTTTCATTTTT
TCACTTCAACTTTTGGGGTATTTCTGTGGGGTAGCATAGAGCAATGATATAAACAACAATTGAGTGA
CAGGTCTACTTTGTTCTCAAAAGGCCATAACCATCTGTTTGCATCTCTTATCACCACACCATCCTCCT
CATCTGGCCTTCAATTGTGGGAACAACTAGCATCCCAACACCAGACTAACTCCACCCAGATGAAA
CCAGTTGTCGCTTACCAGTCAATGAATGTTGAGCTAACGTTCCTTGAAACTCGAATGATCCCAGCCT
TGCTGCGTATCATCCCTCCGCTATTCCGCCGCTTGCTCCAACCATGTTTCCGCCTTTTTCGAACAAG
TTCAAATACCTATCTTTGGCAGGACTTTTCCTCCTGCCTTTTTTAGCCTCAGGTCTCGGTTAGCCTCT
AGGCAAATTCTGGTCTTCATACCTATATCAACTTTTCATCAGATAGCCTTTGGGTTCAAAAAAGAACT
AAAGCAGGATGCCTGATATATAAATCCCAGATGATCTGCTTTTGAAACTATTTTCAGTATCTTGATTC
GTTTACTTACAAACAACTATTGTTGATTTTATCTGGAGAATAATCGAACAAAATGAGGTTCCCGTCTA
TCTTTACTGCTGTTTTGTTTGCCGCTTCGTCCGCTCTTGCTGCCCCGTTAATACGACTACTGAAGA
TGAGACTGCTCAAATTCCAGCTGAGGCAGTGATCGGTTATAGTGATCTAGAAGGAGACTTCGACGT
GGCCGTCTTGCCATTCTCTAATTCCACAAATAACGGCCTTTTGTTTATCAATACCACGATCGCCAGC
ATCGCTGCTAAGGAGGAGGGTGTATCACTGGAGAAGAGATTGTTTGACTATAAAGATGATGATGAT
AAAGGAGGTGGTGGTAGCCGTGTTGACATACAAATGACACAATCCCCTAGCTCCCTGTCCGCATCA
GTCGGAGATAGGGTCACTATTACATGTAGAGCATCGCAAGACGTGAATACTGCTGTAGCATGGTAC
CAGCAAAAGCCAGGTAAGGCTCCTAAACTCCTGATTTACTCAGCATCTTTTCTTTACTCCGGAGTTC
CATCGAGATTCAGTGGCAGTCGTTCTGGTACCGACTTTACTTTGACAATTTCTAGCTTACAGCCTGA

Fig. 33 continued

```
GGATTTCGCTACATACTACTGCCAACAGCATTACACCACTCCACCTACTTTTGGGCAAGGTACTAAG
GTCGAAATCAAGAGAACTGTTGCAGCTCCTTCCGTTTTCATTTTTCCACCTTCAGACGAACAGCTAA
AAAGTGGTACAGCATCAGTGGTATGTTTACTGAACAATTTCTATCCACGTGAAGCTAAGGTCCAGTG
GAAAGTTGACAATGCATTGCAATCAGGTAACTCTCAGGAAAGTGTGACAGAACAAGATTCCAAGGA
TAGCACTTACTCTTTGTCCTCTACGTTGACATTGTCCAAAGCCGACTATGAAAAACACAAAGTTTATG
CATGTGAGGTTACACATCAAGGTTTATCATCTCCCGTTACCAAATCCTTCAACAGAGGAGAATGTTA
AGCGGCCGCTCAAGAGGATGTCAGAATGCCATTTGCCTGAGAGATGCAGGCTTCATTTTTGATACT
TTTTTATTTGTAACCTATATAGTATAGGATTTTTTTTGTCATTTTGTTTCTTCTCGTACGAGCTTGCTC
CTGATCAGCCTATCTCGCAGCAGATGAATATCTTGTGGTAGGGGTTTGGGAAAATCATTCGAGTTT
GATGTTTTTCTTGGTATTTCCCACTCCTCTTCAGAGTACAGAAGATTAAGTGAGACCTTCGTTTGTG
CGGATCCTTCAGTAATGTCTTGTTTCTTTTGTTGCAGTGGTGAGCCATTTTGACTTCGTGAAAGTTTC
TTTAGAATAGTTGTTTCCAGAGGCCAAACATTCCACCCGTAGTAAAGTGCAAGCGTAGGAAGACCA
AGACTGGCATAAATCAGGTATAAGTGTCGAGCACTGGCAGGTGATCTTCTGAAAGTTTCTACTAGC
AGATAAGATCCAGTAGTCATGCATATGGCAACAATGTACCGTGTGGATCTAAGAACGCGTCCTACT
AACCTTCGCATTCGTTGGTCCAGTTTGTTGTTATCGATCAACGTGACAAGGTTGTCGATTCCGCGTA
AGCATGCATACCCAAGGACGCCTGTTGCAATTCCAAGTGAGCCAGTTCCAACAATCTTTGTAATATT
AGAGCACTTCATTGTGTTGCGCTTGAAAGTAAAATGCGAACAAATTAAGAGATAATCTCGAAACCGC
GACTTCAAACGCCAATATGATGTGCGGCACACAATAAGCGTTCATATCCGCTGGGTGACTTTCTCG
CTTTAAAAAATTATCCGAAAAAATTTTCTAGAGTGTTGTTACTTTATACTTCCGGCTCGTATAATACGA
CAAGGTGTAAGGAGGACTAAACCATGGCTAAACTCACCTCTGCTGTTCCAGTCCTGACTGCTCGTG
ATGTTGCTGGTGCTGTTGAGTTCTGGACTGATAGACTCGGTTTCTCCCGTGACTTCGTAGAGGACG
ACTTTGCCGGTGTTGTACGTGACGACGTTACCCTGTTCATCTCCGCAGTTCAGGACCAGGTTGTGC
CAGACAACACTCTGGCATGGGTATGGGTTCGTGGTCTGGACGAACTGTACGCTGAGTGGTCTGAG
GTCGTGTCTACCAACTTCCGTGATGCATCTGGTCCAGCTATGACCGAGATCGGTGAACAGCCCTGG
GGTCGTGAGTTTGCACTGCGTGATCCAGCTGGTAACTGCGTGCATTTCGTCGCAGAGGAACAGGA
CTAAGGAGTATACGTAAATATATAATTATATATAATCATATATATGAATACAATGCAATGAAAGTGAAT
ATGATAAGATTGAAATAATAACAAACAGCGATAAATATATCTCAAAATGGAGTTACACAACAAATAAT
AATAAAATATAAATTATAAATTATAAATTATAAAAGAATAAAAAATAAACCCCACTAATTTATTTTATTA
AAAGATAGATTGGTATCTTTACTTAATAACAATTCTGAAACTTTATTCACTTAATTTTATTTAACTTATT
TAATTTATTTTATCCTTAGCGAAAGCTAAGGATTTTTTTAGGTACCACTGAGCGTCAGACCCCGTAG
AAAAGATCAAAGGATCTTCTTGAGATCCTTTTTTTCTGCGCGTAATCTGCTGCTTGCAAACAAAAAA
CCACCGCTACCAGCGGTGGTTTGTTTGCCGGATCAAGAGCTACCAACTCTTTTTCCGAAGGTAACT
GGCTTCAGCAGAGCGCAGATACCAAATACTGTTCTTCTAGTGTAGCCGTAGTTAGGCCACCACTTC
AAGAACTCTGTAGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAGGCGCAGCGGTC
GGGCTGAACGGGGGGTTCGTGCACACAGCCCAGCTTGGAGCGAACGACCTACACCGAACTGAGA
TACCTACAGCGTGAGCTATGAGAAAGCGCCACGCTTCCCGAAGGGAGAAAGGCGGACAGGTATCC
GGTAAGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCCTTTTGCTGGCC
TTTTGCTCACATGTTCTTTCCTGCGGTACCC
```

Fig. 33 continued

SEQ ID NO:86
AGATCCAATTCCCGCTTTGACTGCCTGAAATCTCCATCGCCTACAATGATGACATTTGGATTTGGTT
GACTCATGTTGGTATTGTGAAATAGACGCAGATCGGGAACACTGAAAAATACACAGTTATTATTCAT
TTAAATGACCCTTGTGACTGACACTTTGGGAGTCCCTATTCTACTTAGTCTCATATCGCATGAAACTT
TTGATAAATTATTTTCTGATAGGAATTTTTCATCAGATATTATCATCGCGGCTTACGTAATAACAAAAA
AAATTGATGGAGTCTATACTAGGCTAACATAAACTAAGTTATTAATTAAACAAAACAAAACGTACTAG
CATTACTGTCATATATAAGGGCTCCTAACTAAAACTGTAAAGACTTCCCGTGCGGCCGCCTACTTAC
CTGGGGACAAGCTCAATGATTTTTGAGTATAGTGGTTGTGCAATGCTTCGTGCATAACGGAACAAG
AGAAAACGTTTCCTTGTTGCCATCTAGATTTGTCTACAGTTAGCTTAGAATACAAGAAGAATGAACC
ATCAGAATCGAGGACTGGAGGGGTGGTTTTGTAGTTATTCTCAGGTTGTCCATTAGATTCCCATTCT
ACCGCGATATCTGAAGGGTAAAAACCTTTCACCAGACATGTTAGAGAAACTTGGTTTTTAGTCAGTT
CGTCCCTCGAAGGAGGCAATGTGTACACCTGAGGTTCACGTGGCTGACCCTTAGCTTTACTAATAG
TCTTTTCAATTGGAGCAGGCAGAGCTTTGTTGGATACCTTACACTTGTACTCCTTGCCGTTCAGCCA
GTCCTGGTGGAGAACAGTCAACACGCTCACTACTCTGTAGGTTGAATTATATTGCTCCTCTCTTGGT
TTGGTTTTAGCGTTATGGACTTCAACACCATCGACATACCAATTAAATTTCACTTCAGGATCCTCGTG
TGAAACGTCAACAACAACACATGTGACCTCTGGCGTTCTGCTGATCATAAGAGTGTCTTTTGGCTTG
GGCGGGAAAAGAAAGACTGAGGGACCACCTAACAGTTCAGGTGCTGGGCAAGGTGGACAAGTATG
GGTTTTGTCGCAACTCTTCGGTTCAACCTTTTTATCGACCTTTGTATTACTTGGCTTATGGTTAACAT
TACAAATGTATGTCTGAGTACCCAAGCTGGATGATGGCACAGTGACCACGGATGATAGGGAGTACA
ATCCTGAGCTTTGCAAAACGGCGGGGAATGTATGAACACCAGAAGTTAAAGCTCCACTATTCCACG
ACACAGTGACTGGTTCTGGGAAATAGTCTTTAACTAAACAACCCAAGGCAGCCGTACCACCGGATG
TAGACTTGGAAGAAGGTGCAAGAGGAAACACCGAGGGACCCTTTGTGGAAGCGGATGAAACTGTG
ACAAGTGTTCCTTGTCCCCAATAATCCATTGCGTAGAAACCATCACCACCCCATCGAGAACAATAAT
AGACAGCAGTGTCCTCAGCCCTCAGGCTATTCATCTGCAAGTAAGCAGTGTTTTTAGATGTATCAGC
AGAAATAGTAAATCTACCTTTAACACTATCGGCATATCTAGTATATCCATTAGTGGGGTATATTCTGG
CAACCCACTCCAAACCTTTACCAGGAGCTTGTCTAACCCAATGGATGTATGTGTCCTTGATGTTAAA
TCCGGAGGCAGCGCAGGACAATCTCAGGGATCCGCCAGGCTGCACTAGACCACCACCTGATTCTA
CCAGTTGCACCTCAGCTTCAGCCTCACGCTTTTCCAAAGACACGCCCTCTTCCTTTGCAGCAATTGA
TGCTATCGTAGTATTGATGAATAACAACCCATTATTCGTCGAATTACTGAATGGCAAAACAGCAACG
TCAAAGTCTCCCTCTAAATCGGAGTATCCGATTACAGCCTCTGCTGGGATTTGTGCGGTTTCATCCT
CTGTTGTAGTATTCACAGGGGCAGCTAATGCGGACGATGCTGCAAAAAGTACAGCGGTGAAAATAC
TTGGAAAACGCATTTTAATTGTAAGTCTTGACTAGAGCAAGTGTTATGGTGAATTTCAAGTAATTGAA
GTGCTGGGTCTACAGCTTATATATGATTTTGGCCTGATGAGCAACAGAGGCTATCACCCCGCTGGG
ATAATGAAACTTACCGATTGCGGCAGGCTAAGCGAAAAGTCCAGGCCAATCGAGGGAAGTTAATTG
CTCAGCTTTCCTGACTAATCCCAACTTTGAGGGGTGCATAGTATGGATTCGGTCTCGTGCGAGAAG
CTTAAACTTTGTTCAATTCCATTAGTAGAGGGTATCATGGAACTTGCATGTGATGATTACTTCATATG
ATATCAGGTACTAGCAATCTCGATTCGAATTTATTAGGTAATGCCGACCGGAACAATAGAAAGACTT
CAAGATTGCTAAAAGACCAATAAGAACGTGTACAGATGTCAGGCCATGAGTTTATTTAAGTGATCTA
TGCTACAATTAAGGTTACAGGAGAACCGCATTCGGAGTTCGATTATTTTTGTAGAAATGTCTTGGTG
TCCTCGTCCAATCAGGTAGCCATCTCTGAAATATCTGGCTCCGTTGCAACTCCGAACGACCTGCTG
GCAACGTAAAATTCTCCGGGGTAAAACTTAAATGTGGAGTAATGGAACCAGAAACGTCTCTTCCCTT
CTCTCTCCTTCCACCGCCCGTTACCGTCCCTAGGAAATTTTACTCTGCTGGAGAGCTTCTTCTACGG
CCCCCTTGCAGCAATGCTCTTCCCAGCATTACGTTGCGGGTAAAACGGAGGTCGTGTACCCGACCT
AGCAGCCCAGGGATGGAAAAGTCCCGGCCGTCGCTGGCAATAATAGCGGGCGGACGCATGTCAT
GAGATTATTGGAAACCACCAGAATCGAATATAAAAGGCGAACACCTTTCCCAATTTTGGTTTCTCCT
GACCCAAAGACTTTAAATTTAATTTATTTGTCCCTATTTCAATCAATTGAACAACTATCAAAACACAAT
GAGGTTCCCGTCTATCTTTACTGCTGTTTTGTTTGCCGCTTCGTCCGCTCTTGCTGCCCCGTTAAT
ACGACTACTGAAGATGAGACTGCTCAAATTCCAGCTGAGGCAGTGATCGGTTATAGTGATCTAGAA
GGAGACTTCGACGTGGCCGTCTTGCCATTCTCTAATTCCACAAATAACGGCCTTTTGTTTATCAATA
CCACGATCGCCAGCATCGCTGCTAAGGAGGAGGGTGTATCACTGGAGAAGAGATTGTTTGACTATA
AAGATGATGATGATAAAGGAGGTGGTGGTAGCCGTGTTGACATACAAATGACACAATCCCCTAGCT
CCCTGTCCGCATCAGTCGGAGATAGGGTCACTATTACATGTAGAGCATCGCAAGACGTGAATACTG
CTGTAGCATGGTACCAGCAAAAGCCAGGTAAGGCTCCTAAACTCCTGATTTACTCAGCATCTTTTCT
TTACTCCGGAGTTCCATCGAGATTCAGTGGCAGTCGTTCTGGTACCGACTTTACTTTGACAATTTCT
AGCTTACAGCCTGAGGATTTCGCTACATACTACTGCCAACAGCATTACACCACTCCACCTACTTTTG
GGCAAGGTACTAAGGTCGAAATCAAGAGAACTGTTGCAGCTCCTTCCGTTTTCATTTTTCCACCTTC
AGACGAACAGCTAAAAAGTGGTACAGCATCAGTGGTATGTTTACTGAACAATTTCTATCCACGTGAA
GCTAAGGTCCAGTGGAAAGTTGACAATGCATTGCAATCAGGTAACTCTCAGGAAAGTGTGACAGAA

Fig. 33 continued

```
CAAGATTCCAAGGATAGCACTTACTCTTTGTCCTCTACGTTGACATTGTCCAAAGCCGACTATGAAA
AACACAAAGTTTATGCATGTGAGGTTACACATCAAGGTTTATCATCTCCCGTTACCAAATCCTTCAAC
AGAGGAGAATGTTAAGCGGCCGCTCAAGAGGATGTCAGAATGCCATTTGCCTGAGAGATGCAGGC
TTCATTTTTGATACTTTTTTATTTGTAACCTATATAGTATAGGATTTTTTTTGTCATTTTGTTTCTTCTC
GTACGAGCTTGCTCCTGATCAGCCTATCTCGCAGCAGATGAATATCTTGTGGTAGGGGTTTGGGAA
AATCATTCGAGTTTGATGTTTTTCTTGGTATTTCCCACTCCTCTTCAGAGTACAGAAGATTAAGTGAG
ACCTTCGTTTGTGCGGATCCTTCAGTAATGTCTTGTTTCTTTTGTTGCAGTGGTGAGCCATTTTGACT
TCGTGAAAGTTTCTTTAGAATAGTTGTTTCCAGAGGCCAAACATTCCACCCGTAGTAAAGTGCAAGC
GTAGGAAGACCAAGACTGGCATAAATCAGGTATAAGTGTCGAGCACTGGCAGGTGATCTTCTGAAA
GTTTCTACTAGCAGATAAGATCCAGTAGTCATGCATATGGCAACAATGTACCGTGTGGATCTAAGAA
CGCGTCCTACTAACCTTCGCATTCGTTGGTCCAGTTTGTTGTTATCGATCAACGTGACAAGGTTGTC
GATTCCGCGTAAGCATGCATACCCAAGGACGCCTGTTGCAATTCCAAGTGAGCCAGTTCCAACAAT
CTTTGTAATATTAGAGCACTTCATTGTGTTGCGCTTGAAAGTAAAATGCGAACAAATTAAGAGATAAT
CTCGAAACCGCGACTTCAAACGCCAATATGATGTGCGGCACACAATAAGCGTTCATATCCGCTGGG
TGACTTTCTCGCTTTAAAAAATTATCCGAAAAAATTTTCTAGAGTGTTGTTACTTTATACTTCCGGCTC
GTATAATACGACAAGGTGTAAGGAGGACTAAACCATGGCTAAACTCACCTCTGCTGTTCCAGTCCT
GACTGCTCGTGATGTTGCTGGTGCTGTTGAGTTCTGGACTGATAGACTCGGTTCTCCCGTGACTT
CGTAGAGGACGACTTTGCCGGTGTTGTACGTGACGACGTTACCCTGTTCATCTCCGCAGTTCAGGA
CCAGGTTGTGCCAGACAACACTCTGGCATGGGTATGGGTTCGTGGTCTGGACGAACTGTACGCTG
AGTGGTCTGAGGTCGTGTCTACCAACTTCCGTGATGCATCTGGTCCAGCTATGACCGAGATCGGTG
AACAGCCCTGGGGTCGTGAGTTTGCACTGCGTGATCCAGCTGGTAACTGCGTGCATTTCGTCGCA
GAGGAACAGGACTAAGGAGTATACGTAAATATATAATTATATATAATCATATATATGAATACAATGCA
ATGAAAGTGAATATGATAAGATTGAAATAATAACAAACAGCGATAAATATATCTCAAAATGGAGTTAC
ACAACAAATAATAATAAAATATAAATTATAAATTATAAATTATAAAAGAATAAAAAATAAACCCCACTA
ATTTATTTTATTAAAAGATAGATTGGTATCTTTACTTAATAACAATTCTGAAACTTTATTCACTTAATTT
TATTTAACTTATTTAATTTATTTTATCCTTAGCGAAAGCTAAGGATTTTTTTAGGTACCACTGAGCGT
CAGACCCCGTAGAAAAGATCAAAGGATCTTCTTGAGATCCTTTTTTTCTGCGCGTAATCTGCTGCTT
GCAAACAAAAAAACCACCGCTACCAGCGGTGGTTTGTTTGCCGGATCAAGAGCTACCAACTCTTTT
TCCGAAGGTAACTGGCTTCAGCAGAGCGCAGATACCAAATACTGTTCTTCTAGTGTAGCCGTAGTT
AGGCCACCACTTCAAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGATAGTTACCGGATA
AGGCGCAGCGGTCGGGCTGAACGGGGGGTTCGTGCACACAGCCCAGCTTGGAGCGAACGACCTA
CACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTTGAGCGTCGATTTTTGTG
ATGCTCGTCAGGGGGCGGAGCCTATGGAAAAACGCCAGCAACGCGGCCTTTTTACGGTTCCTGG
CCTTTTGCTGGCCTTTTGCTCACATGTTCTTTCCTGCGGTACCC
```

Fig. 33 continued

SEQ ID NO: 87
ATGAGTGTTGTCAGCAAGCAATACGACATCCACGAAGGCATTATCTTTGTAATTGAATTGACCCCGG
AGCTTCACGCGCCGGCTTCAGAAGGGAAATCTCAGCTCCAGATCATCTTAGAGAATGTCAGTGAGG
TTATTTCTGAGCTAATCATTACCTTGCCCGGTACAGGAATAGGGTGTTACCTTATTAATTACGACGG
TGGTCAAAACGACGAAATTTACCCCATTTTTGAGTTACAAGACCTGAATTTGGAAATGATGAAACAA
TTGTACCAAGTCTTGGAGGACCATGTAAGTGGGCTTAATCCTCTCGAGAAGCAATTCCCAATTGAAC
ACAGTAAACCGTTATCAGCCACTCTGTTCTTTCACTTAAGGTCTCTTTTTTACATGGCGAAGACTCAT
AAGCGTACTGGAAGACATTACAACTTGAAAAAGATTTTCTTGTTCACTAATAACGATAAACCTTACAA
TGGAAACTCTCAGCTGAGAGTTCCCTTGAAGAAAACCCTGGCTGATTACAATGACGTAGACATTACT
TTGATTCCGTTTCTTCTGAACAAGCCTTCAGGTGTCAAGTTTGACAAGACGGAATACTCAGAAATTT
TGTTCTATGATAAAGATGCTTGTTCGATGTCAATTGAGGAGATCCGCCAACGAATTTCTAGACATAA
GGAGATCAAGCGGGTTTACTTCACCTGTCCTTTGAAAATCGCAAATAACTTGTGCATTTCTGTGAAA
GGTTATTCTATGTTTTATCATGAAACTCCAAGGAAGATCAAATTTGTCGTCAATGAGGGTTCAACTTT
CAAAGATGTGGAGACAAAATCTCAGTTTGTCGATCCAACATCCGGAAAAGAGTTTTCCAGTGAACA
GCTGATCAAAGCATATCCTCTAGGTGCCGATGCTTACATTCCTTTAAACTCAGAGCAAGTCAAAACA
ATAAATCGATTTAATGATATCATCAATATCCCCTCTTTGGAAATTCTAGGTTTCAGGGATATATCTAAT
TGGTTGCCACAGTATCAGTTTGGCAAAGCATCGTTTTTATCCCCTAATAACTATGGTGATTTTACACA
TTCGCAGAGAACATTTAGTTGTCTTTTACAATCCATGACCAAAAAATCCAAGTTTGCAGTACTTTTTG
GTACTTTGAAGAACAATGCGGCTCCAAGGTTGTTTGGCATGATTCCCTCTACGTTACCTCAATACGA
AAGTTGTAATCTTCCCCAAGGGTTCTTCCTGATAAAGCTCCCGTATCTGGATGATGTACGCCAGCTG
CCACCCAAAATTGCCCCGGTCGATGCTGATTTGGATGTATTAGTTTCACTTTTCAGCAACCTGGTCG
GAAAGATCCACATCAAGAATGGATACCAACCCCAAGAGTATGAAAATCCTTCCCTACAATGGCACTT
CAAAATGTTACGTGACGATTACCTTCAATTGGAACACGATATCGACATCAGTGACCCCCTTGAGAAA
CAAAAGTACATAAACAGCCTCGATGAGACAAAAACCAAGATCATGAAACTACGGGACTATGTCAAG
GAAACTGCCGATGATGACGACCCTTCACGGCTTGCCAACACTCTCAAAGAGCTCAACCAAGAGCTG
AACAAAATTTCCAACTTTGATATCATCGCCAATAAGAAGCCAAAGACCCCCACGACAGTAGACCCTG
TTCCTACTGATGATGACATCATCAACGCCTGGAAGGCAGGAACTCTGAACGGTTTCAAGGTGGATC
AATTACGAAAATACGTAAGGTCACGAAACAACTTTCTGGAGACGGCCTCCAAAAAGGCAGATCTCA
TCGCCAACATTGACAAGTACTTTCAGCAGAAGTTCAAAGAGACTAAGGCCTGA

SEQUENCE LISTING

<160> NUMBER OF SEQ ID NOS: 87

<210> SEQ ID NO 1
<211> LENGTH: 692
<212> TYPE: DNA
<213> ORGANISM: Artificial Sequence
<220> FEATURE:
<223> OTHER INFORMATION: Promoter

<400> SEQUENCE: 1

| | | | | | |
|---|---|---|---|---|---|
| agtgtgtaat | catatatata | ataaatgagg | aataataatt | gaatagagat | ttaacgagtc | 60 |
| gaagtttctg | aaatatacgc | acagtttata | tttatgattt | tgatatctaa | ctacagtctt | 120 |
| ctccatatat | ttaactataa | ataataaagt | ataaactct  | tatgaaactg | tttcaccaca | 180 |
| ttttttttcta | cgtaatcgaa | ctccgaatgc | ggttctcctg | taaccttaat | tgtagcatag | 240 |
| atcacttaaa | taaactcatg | gcctgacatc | tgtacacgtt | cttattggtc | ttttagcaat | 300 |
| cttgaagtct | ttctattgtt | ccggtcggca | ttacctaata | aattcgaatc | gagattgcta | 360 |
| gtacctgata | tcatatgaag | taatcatcac | atgcaagttc | catgataccc | tctactaatg | 420 |
| gaattgaaca | aagtttaagc | ttctcgcacg | agaccgaatc | catactatgc | accctcaaa  | 480 |
| gttgggatta | gtcaggaaag | ctgagcaatt | aacttccctc | gattggcctg | gacttttcgc | 540 |
| ttagcctgcc | gcaatcggta | agtttcatta | tcccagcggg | gtgatagcct | ctgttgctca | 600 |
| tcaggccaaa | atcatatata | agctgtagac | ccagcacttc | aattacttga | aattcaccat | 660 |
| aacacttgct | ctagtcaaga | cttacaatta | aa | | | 692 |

<210> SEQ ID NO 2
<211> LENGTH: 264
<212> TYPE: DNA
<213> ORGANISM: Artificial Sequence
<220> FEATURE:
<223> OTHER INFORMATION: Promoter

<400> SEQUENCE: 2

| | | | | | |
|---|---|---|---|---|---|
| aaaagtgcga | ggaagaataa | aaatactgct | tcctccgcct | gggaaagagc | aaaaagacgc | 60 |
| agaggaaact | aaagtgtgta | atcatatata | taataaatga | ggaataataa | ttgaatagag | 120 |
| atttaacgag | tcgaagtttc | tgaaatatac | gcacagttta | tatttatgat | tttgatatct | 180 |
| aactacagtc | ttctccatat | atttaactat | aaataataaa | gtatataact | cttatgaaac | 240 |
| tgtttcacca | cattttttc  | tacg | | | | 264 |

<210> SEQ ID NO 3
<211> LENGTH: 192
<212> TYPE: DNA
<213> ORGANISM: Artificial Sequence
<220> FEATURE:
<223> OTHER INFORMATION: Promoter

<400> SEQUENCE: 3

| | | | | | |
|---|---|---|---|---|---|
| agtgtgtaat | catatatata | ataaatgagg | aataataatt | gaatagagat | ttaacgagtc | 60 |
| gaagtttctg | aaatatacgc | acagtttata | tttatgattt | tgatatctaa | ctacagtctt | 120 |
| ctccatatat | ttaactataa | ataataaagt | ataaactct  | tatgaaactg | tttcaccaca | 180 |
| ttttttttcta | cg | | | | | 192 |

<210> SEQ ID NO 4
<211> LENGTH: 500
<212> TYPE: DNA
<213> ORGANISM: Artificial Sequence

```
<220> FEATURE:
<223> OTHER INFORMATION: Promoter

<400> SEQUENCE: 4
taatcgaact ccgaatgcgg ttctcctgta accttaattg tagcatagat cacttaaata      60
aactcatggc ctgacatctg tacacgttct tattggtctt ttagcaatct tgaagtcttt     120
ctattgttcc ggtcggcatt acctaataaa ttcgaatcga gattgctagt acctgatatc     180
atatgaagta atcatcacat gcaagttcca tgataccctc tactaatgga attgaacaaa     240
gtttaagctt ctcgcacgag accgaatcca tactatgcac ccctcaaagt tgggattagt     300
caggaaagct gagcaattaa cttccctcga ttggcctgga cttttcgctt agcctgccgc     360
aatcggtaag tttcattatc ccagcggggt gatagcctct gttgctcatc aggccaaaat     420
catatataag ctgtagaccc agcacttcaa ttacttgaaa ttcaccataa cacttgctct     480
agtcaagact tacaattaaa                                                 500

<210> SEQ ID NO 5
<211> LENGTH: 1652
<212> TYPE: DNA
<213> ORGANISM: Artificial Sequence
<220> FEATURE:
<223> OTHER INFORMATION: Promoter

<400> SEQUENCE: 5
ggagtatacg taaatatata attatatata atcatatata tgaatacaat gcaatgaaag      60
tgaatatgat aagattgaaa taataacaaa cagcgataaa tatatctcaa aatggagtta    120
cacaacaaat aataataaaa tataaattat aaattataaa ttataaaaga ataaaaaata    180
aaccccacta atttatttta ttaaaagata gattggtatc tttacttaat aacaattctg    240
aaactttatt cacttaattt tatttaactt atttaattta tttttacccc agttttttcag   300 tacaatgcag ctccgaaact ttatttggct gtgatttggc tgtgatttgg ctgtgatttg    360
gcttggcttg gctggctgga attgtctcct gcaggaattg ctcggggtcc ggttctcccg    420
ctggctggct atttggcggg ctggctattt ggcgggctgg ctggctggct gctctgccat    480
ctgctgtggc caccccgcat ctctggatgc acgccgtgca gctggacgtg cgtctaccct    540
gcagccgtgt gccttatttc ccaatctccc aatctctcaa tctgccagtc agccaaaaca    600
ccggccaggc aggcaggcag gcaggcaggc aggcagtgaa gccttccccac gccccactcc    660 gcataaacat ccccagcagt ttccccagca gtttccccag cttttcaatt taataaaata    720
gcctgtttct gtttctgttt tatattatac aattttttat cctaataatt actctttcgg    780
gaattaaata ataattatat catatacccca tatcacattt tactatattt actatctata    840
aataaattca tattataata ttaatttata ttcgcttaat taaaatgctc ttttccatca    900
tcatcatcat catcatcatc acgagttttc ggttatcaat actcttttca ttaatttcta    960
gaatttcatt atttattttt tattgactgg aaattttcaa tcaattttat ttattttttat   1020 ttatttattt tcatattctt agatttaaac ttttttagatg accgctattt tacttactta   1080
cttactgttg ttttatatta tgataagaat taattttcat atttatgatg atgatgatgt    1140
aaatttaacc tagtatacta ttttaaagtt atcactatct tttagtgctg gcatttttta    1200
ttctattttc atatatgtat atacgtaaat taagtatcat cacgctgctt actgtacgtt    1260
taaaatgtgg agatggaaat agagatgggg atgaagatga agatgatgag aattataaac    1320
cattcattca ttaatcaatc aatataactt ataaaaaaat ttatatttaa atgaattaat    1380
```

```
ttcctttatt ttaataatat cgttaattct tttaaattct attttatttt aattctttct    1440
ttatcatagt tatcatataa caattatata acatagatac acaattatta tttcattatc    1500
atattatttt ttaaaatatt gattatttt  aaaataatat cttaattaat taattttac    1560 gaatatacaa attttaacga cttactttt  ttaacgaatt ttaacgaact tttaaaaaaa    1620 caaaaaaaa  aaaacaaaat tatttttcaa ta                                  1652

<210> SEQ ID NO 6
<211> LENGTH: 284
<212> TYPE: DNA
<213> ORGANISM: Artificial Sequence
<220> FEATURE:
<223> OTHER INFORMATION: Promoter

<400> SEQUENCE: 6
ggagtatacg taaatatata attatatata atcatatata tgaatacaat gcaatgaaag      60
tgaatatgat aagattgaaa taataacaaa cagcgataaa tatatctcaa aatggagtta    120
cacaacaaat aataataaaa tataaattat aaattataaa ttataaaaga ataaaaaata    180
aaccccacta atttatttta ttaaaagata gattggtatc tttacttaat aacaattctg    240
aaactttatt cacttaattt tatttaactt atttaattta tttt                     284

<210> SEQ ID NO 7
<211> LENGTH: 379
<212> TYPE: DNA
<213> ORGANISM: Artificial Sequence
<220> FEATURE:
<223> OTHER INFORMATION: Promoter

<400> SEQUENCE: 7 tacccccagtt tttcagtaca atgcagctcc gaaactttat ttggctgtga tttggctgtg     60
atttggctgt gatttggctt ggcttggctg gctggaattg tctcctgcag gaattgctcg    120
gggtccggtt ctcccgctgg ctggctattt ggcgggctgg ctatttggcg ggctggctgg    180
ctggctgctc tgccatctgc tgtggccacc ccgcatctct ggatgcacgc cgtgcagctg    240
gacgtgcgtc taccctgcag ccgtgtgcct tatttcccaa tctcccaatc tctcaatctg    300
ccagtcagcc aaaacaccgg ccaggcaggc aggcaggcag gcaggcaggc agtgaagcct    360
tcccacgccc cactccgca                                                 379

<210> SEQ ID NO 8
<211> LENGTH: 223
<212> TYPE: DNA
<213> ORGANISM: Artificial Sequence
<220> FEATURE:
<223> OTHER INFORMATION: Promoter

<400> SEQUENCE: 8
taaacatccc cagcagtttc cccagcagtt tccccagctt ttcaatttaa taaaatagcc      60
tgtttctgtt tctgttttat attatacaat tttttatcct aataattact ctttcgggaa    120
ttaaataata attatatcat atacccatat cacattttac tatatttact atctataaat    180
aaattcatat tataatatta atttatattc gcttaattaa aat                      223

<210> SEQ ID NO 9
<211> LENGTH: 356
<212> TYPE: DNA
<213> ORGANISM: Artificial Sequence
<220> FEATURE:
<223> OTHER INFORMATION: Promoter
```

<400> SEQUENCE: 9

```
gctctttcc atcatcatca tcatcatcat catcacgagt tttcggttat caatactctt    60
ttcattaatt tctagaattt cattatttat tttttattga ctggaaattt tcaatcaatt   120
ttatttattt ttatttattt atttttcatat tcttagattt aaactttta gatgaccgct   180
attttactta cttacttact gttgttttat attatgataa gaattaattt tcatatttat   240
gatgatgatg atgtaaattt aacctagtat actattttaa agttatcact atctttagt    300
gctggcattt tttattctat tttcatatat gtatatacgt aaattaagta tcatca       356
```

<210> SEQ ID NO 10
<211> LENGTH: 410
<212> TYPE: DNA
<213> ORGANISM: Artificial Sequence
<220> FEATURE:
<223> OTHER INFORMATION: Promoter

<400> SEQUENCE: 10

```
cgctgcttac tgtacgttta aaatgtggag atggaaatag agatggggat gaagatgaag    60
atgatgagaa ttataaacca ttcattcatt aatcaatcaa taaacttat aaaaaaattt    120
atatttaaat gaattaattt cctttatttt aataatatcg ttaattcttt taaattctat   180
tttatttaa ttctttcttt atcatagtta tcatataaca attatataac atagatacac    240
aattattatt tcattatcat attattttt aaaatattga ttattttaa aataatatct    300
taattaatta attttacga atatacaaat tttaacgact tacttttttt aacgaatttt    360
aacgaacttt taaaaaaca aaaaaaaaa aacaaaatta tttttcaata                410
```

<210> SEQ ID NO 11
<211> LENGTH: 989
<212> TYPE: DNA
<213> ORGANISM: Artificial Sequence
<220> FEATURE:
<223> OTHER INFORMATION: Promoter

<400> SEQUENCE: 11

```
taaacatccc cagcagtttc cccagcagtt tccccagctt ttcaatttaa taaaatagcc    60
tgtttctgtt tctgttttat attatacaat tttttatcct aataattact ctttcgggaa   120
ttaaataata attatatcat atacccatat cacattttac tatatttact atctataaat   180
aaattcatat tataatatta atttatattc gcttaattaa aatgctcttt tccatcatca   240
tcatcatcat catcatcacg agtttcggt tatcaatact cttttcatta atttctagaa    300
tttcattatt tattttttat tgactggaaa ttttcaatca atttattta ttttattta     360
tttatttca tattcttaga tttaaacttt ttagatgacc gctattttac ttacttactt    420
actgttgttt tatattatga taagaattaa ttttcatatt tatgatgatg atgatgtaaa   480
tttaacctag tatactattt taaagttatc actatctttt agtgctggca ttttttattc   540
tattttcata tatgtatata cgtaaattaa gtatcatcac gctgcttact gtacgtttaa   600
aatgtggaga tggaaataga gatggggatg aagatgaaga tgatgagaat tataaaccat   660
tcattcatta atcaatcaat ataacttata aaaaaattta tatttaaatg aattaatttc   720
ctttatttta ataatatcgt taattctttt aaattctatt ttatttaat tctttcttta   780
tcatagttat catataacaa ttatataaca tagatacaca attattattt cattatcata   840
ttattttta aaatattgat tattttaaa ataatatctt aattaattaa ttttacgaa     900
```

```
tatacaaatt ttaacgactt acttttttta acgaatttta acgaactttt aaaaaaacaa    960
aaaaaaaaaa acaaaattat ttttcaata                                      989

<210> SEQ ID NO 12
<211> LENGTH: 614
<212> TYPE: DNA
<213> ORGANISM: Artificial Sequence
<220> FEATURE:
<223> OTHER INFORMATION: Promoter

<400> SEQUENCE: 12
agtgtgtaat catatatata ataaatgagg aataataatt gaatagagat ttaacgagtc     60
gaagtttctg aaatatacgc acagtttata tttatgattt tgatatctaa ctacagtctt    120
ctccatatat ttaactataa ataataaagt ataaactct tatgaaactg tttcaccaca     180 ttttttttcta cgtaatcgaa ctccgaatgc ggttctcctg taaccttaat tgtagcatag   240
atcacttaaa taaactcatg gcctgacatc tgtacacgtt cttattggtc ttttagcaat    300
cttgaagtct ttctattgtt ccggtcggca ttacctaata aattcgaatc gagattgcta    360
gtacctgata tcatatgaag taatcatcac atgcaagttc catgataccc tctactaatg    420
gaattgaaca aagtttaagc ttctcgcacg agaccgaatc catactatgc accctcaaa     480 gttgggatta gtcaggaaag ctgagcaatt aacttccctc gattggcctg gacttttcgc    540
ttagcctgcc gcaatcggta agtttcatta tcccagcggg gtgatagcct ctgttgctca    600
tcaggccaaa atca                                                      614

<210> SEQ ID NO 13
<211> LENGTH: 436
<212> TYPE: DNA
<213> ORGANISM: Artificial Sequence
<220> FEATURE:
<223> OTHER INFORMATION: Promoter

<400> SEQUENCE: 13
atgagaagag cgaattcggc gcgccggtaa gatccaaatc gatgaattga ccaagcacta     60
cggtatgaag ccagaagact acactgctgt cagatgtggt atgaatgtcg ccaagtacat    120
catcgaagat aagattgatg ctggtattgg tatcgaatgt atgcaacaag tcgaattgga    180
agagtacttg gccaagcaag gcagaccagc ttctgatgct aaaatgttga gaattgacaa    240
gttggcttgc ttgggttgct gttgtttctg taccgttctt tacatctgca acgatgaatt    300
tttgaagaaa aaccctgaaa aggtcagaaa gttcttgaaa gccatcaaga aggcaaccga    360
ctacgttcta gccgaccctg tgaaggcttg gaaagaatac atcgacttca gcctcaatt    420 gaacagctct tcataa                                                    436

<210> SEQ ID NO 14
<211> LENGTH: 69
<212> TYPE: DNA
<213> ORGANISM: Artificial Sequence
<220> FEATURE:
<223> OTHER INFORMATION: Primer

<400> SEQUENCE: 14
gttagtagat atttatacca ttctgcgaga aggtcctaaa agtgcgagga agaataaaaa     60
tactgcttc                                                             69

<210> SEQ ID NO 15
<211> LENGTH: 74
```

```
<212> TYPE: DNA
<213> ORGANISM: Artificial Sequence
<220> FEATURE:
<223> OTHER INFORMATION: Primer

<400> SEQUENCE: 15
agtgaaaagt tcttctcctt tgctagccat cgtagaaaaa aatgtggtga aacagtttca    60
taagagttat atac                                                     74

<210> SEQ ID NO 16
<211> LENGTH: 66
<212> TYPE: DNA
<213> ORGANISM: Artificial Sequence
<220> FEATURE:
<223> OTHER INFORMATION: Primer

<400> SEQUENCE: 16
cagaagatta agtgagacct tcgtttgtgc ggatccttca gtaatgtctt gtttcttttg    60
ttgcag                                                              66

<210> SEQ ID NO 17
<211> LENGTH: 63
<212> TYPE: DNA
<213> ORGANISM: Artificial Sequence
<220> FEATURE:
<223> OTHER INFORMATION: Primer

<400> SEQUENCE: 17
ctacggggtc tgacgctcag tggtacctgc agctaaggta atcagatcca agtttcccca    60
atc                                                                 63

<210> SEQ ID NO 18
<211> LENGTH: 67
<212> TYPE: DNA
<213> ORGANISM: Artificial Sequence
<220> FEATURE:
<223> OTHER INFORMATION: Primer

<400> SEQUENCE: 18
cagaagatta agtgagacct tcgtttgtgc ggatccatac cgaaaggtaa acaacttcgg    60
ggaattg                                                             67

<210> SEQ ID NO 19
<211> LENGTH: 57
<212> TYPE: DNA
<213> ORGANISM: Artificial Sequence
<220> FEATURE:
<223> OTHER INFORMATION: Primer

<400> SEQUENCE: 19
ggcgtatcac gaggcccttt cgtctgccag agctgtcaca tacttgaaat agggttg       57

<210> SEQ ID NO 20
<211> LENGTH: 57
<212> TYPE: DNA
<213> ORGANISM: Artificial Sequence
<220> FEATURE:
<223> OTHER INFORMATION: Primer

<400> SEQUENCE: 20
caaccctatt tcaagtatgt gacagctctg gcagacgaaa gggcctcgtg atacgcc       57

<210> SEQ ID NO 21
```

<211> LENGTH: 59
<212> TYPE: DNA
<213> ORGANISM: Artificial Sequence
<220> FEATURE:
<223> OTHER INFORMATION: Primer

<400> SEQUENCE: 21 gatctttct acggggtctg acgctcagta acgaaaactc acgttaaggg attttggtc    59

<210> SEQ ID NO 22
<211> LENGTH: 65
<212> TYPE: DNA
<213> ORGANISM: Artificial Sequence
<220> FEATURE:
<223> OTHER INFORMATION: Primer

<400> SEQUENCE: 22
gaagattggg gaaacttgga tctgattacc ttagctgcag tcgagataag ctgggggaac    60
attcg    65

<210> SEQ ID NO 23
<211> LENGTH: 68
<212> TYPE: DNA
<213> ORGANISM: Artificial Sequence
<220> FEATURE:
<223> OTHER INFORMATION: Primer

<400> SEQUENCE: 23
ctacggggtc tgacgctcag tggtacctcg acaattaata tttacttatt ttggtcaacc    60
ccaaatag    68

<210> SEQ ID NO 24
<211> LENGTH: 95
<212> TYPE: DNA
<213> ORGANISM: Artificial Sequence
<220> FEATURE:
<223> OTHER INFORMATION: Primer

<400> SEQUENCE: 24
gaagattggg gaaacttgga tctgattacc ttagctgcag agtgtgtaat catatatata    60
ataaatgagg aataataatt gaatagagat ttaac    95

<210> SEQ ID NO 25
<211> LENGTH: 63
<212> TYPE: DNA
<213> ORGANISM: Artificial Sequence
<220> FEATURE:
<223> OTHER INFORMATION: Primer

<400> SEQUENCE: 25
ctacggggtc tgacgctcag tggtacccgt agaaaaaaat gtggtgaaac agtttcataa    60
gag    63

<210> SEQ ID NO 26
<211> LENGTH: 96
<212> TYPE: DNA
<213> ORGANISM: Artificial Sequence
<220> FEATURE:
<223> OTHER INFORMATION: Primer

<400> SEQUENCE: 26
gaagattggg gaaacttgga tctgattacc ttagctgcag ggagtatacg taaatatata    60
attatatata atcatatata tgaatacaat gcaatg    96

<210> SEQ ID NO 27
<211> LENGTH: 87
<212> TYPE: DNA
<213> ORGANISM: Artificial Sequence
<220> FEATURE:
<223> OTHER INFORMATION: Primer

<400> SEQUENCE: 27
ctacggggtc tgacgctcag tggtaccaaa ataaattaaa taagttaaat aaaattaagt    60
gaataaagtt tcagaattgt tattaag                                       87

<210> SEQ ID NO 28
<211> LENGTH: 67
<212> TYPE: DNA
<213> ORGANISM: Artificial Sequence
<220> FEATURE:
<223> OTHER INFORMATION: Primer

<400> SEQUENCE: 28
gaagattggg gaaacttgga tctgattacc ttagctgcag tacccagtt tttcagtaca     60 atgcagc                                                             67

<210> SEQ ID NO 29
<211> LENGTH: 43
<212> TYPE: DNA
<213> ORGANISM: Artificial Sequence
<220> FEATURE:
<223> OTHER INFORMATION: Primer

<400> SEQUENCE: 29
ctacggggtc tgacgctcag tggtacctgc ggagtggggc gtg                     43

<210> SEQ ID NO 30
<211> LENGTH: 65
<212> TYPE: DNA
<213> ORGANISM: Artificial Sequence
<220> FEATURE:
<223> OTHER INFORMATION: Primer

<400> SEQUENCE: 30
gaagattggg gaaacttgga tctgattacc ttagctgcag taaacatccc cagcagtttc    60
cccag                                                               65

<210> SEQ ID NO 31
<211> LENGTH: 91
<212> TYPE: DNA
<213> ORGANISM: Artificial Sequence
<220> FEATURE:
<223> OTHER INFORMATION: Primer

<400> SEQUENCE: 31
ctacggggtc tgacgctcag tggtaccatt ttaattaagc gaatataaat taatattata    60
atatgaattt atttatagat agtaaatata g                                  91

<210> SEQ ID NO 32
<211> LENGTH: 74
<212> TYPE: DNA
<213> ORGANISM: Artificial Sequence
<220> FEATURE:
<223> OTHER INFORMATION: Primer

<400> SEQUENCE: 32
gaagattggg gaaacttgga tctgattacc ttagctgcag gctctttcc atcatcatca    60 tcatcatcat catc    74

<210> SEQ ID NO 33
<211> LENGTH: 79
<212> TYPE: DNA
<213> ORGANISM: Artificial Sequence
<220> FEATURE:
<223> OTHER INFORMATION: Primer

<400> SEQUENCE: 33
ctacggggtc tgacgctcag tggtacctga tgatacttaa tttacgtata tacatatatg    60
aaaatagaat aaaaaatgc    79

<210> SEQ ID NO 34
<211> LENGTH: 68
<212> TYPE: DNA
<213> ORGANISM: Artificial Sequence
<220> FEATURE:
<223> OTHER INFORMATION: Primer

<400> SEQUENCE: 34
gaagattggg gaaacttgga tctgattacc ttagctgcag cgctgcttac tgtacgttta    60
aaatgtgg    68

<210> SEQ ID NO 35
<211> LENGTH: 84
<212> TYPE: DNA
<213> ORGANISM: Artificial Sequence
<220> FEATURE:
<223> OTHER INFORMATION: Primer

<400> SEQUENCE: 35
ctacggggtc tgacgctcag tggtacctat tgaaaaataa ttttgttttt ttttttttgt    60 tttttaaaa gttcgttaaa attc    84

<210> SEQ ID NO 36
<211> LENGTH: 60
<212> TYPE: DNA
<213> ORGANISM: Artificial Sequence
<220> FEATURE:
<223> OTHER INFORMATION: Primer

<400> SEQUENCE: 36
acacatggca tggatgaatt gtacaagtaa gcggccgcga cctctgttgc ctctttgttg    60

<210> SEQ ID NO 37
<211> LENGTH: 59
<212> TYPE: DNA
<213> ORGANISM: Artificial Sequence
<220> FEATURE:
<223> OTHER INFORMATION: Primer

<400> SEQUENCE: 37
caaaagaaac aagacattac tgaaggatcc ttaagctgga agagccaatc tcttgaaag    59

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38

```
gatggttccg ttcaactagc agac                                            24
```

<210> SEQ ID NO 39
<211> LENGTH: 60
<212> TYPE: DNA
<213> ORGANISM: Artificial Sequence
<220> FEATURE:
<223> OTHER INFORMATION: Primer

<400> SEQUENCE: 39

```
caaaagaaac aagacattac tgaaggatcc gcttattttc tgccgaattt tcatgaagtt     60
```

<210> SEQ ID NO 40
<211> LENGTH: 58
<212> TYPE: DNA
<213> ORGANISM: Artificial Sequence
<220> FEATURE:
<223> OTHER INFORMATION: Primer

<400> SEQUENCE: 40

```
acacatggca tggatgaatt gtacaagtaa caaagacgtt gtttcatcgc gctattac      58
```

<210> SEQ ID NO 41
<211> LENGTH: 60
<212> TYPE: DNA
<213> ORGANISM: Artificial Sequence
<220> FEATURE:
<223> OTHER INFORMATION: Primer

<400> SEQUENCE: 41

```
caaaagaaac aagacattac tgaaggatcc gcttattttc tgccgaattt tcatgaagtt     60
```

<210> SEQ ID NO 42
<211> LENGTH: 282
<212> TYPE: DNA
<213> ORGANISM: Artificial Sequence
<220> FEATURE:
<223> OTHER INFORMATION: Primer

<400> SEQUENCE: 42

```
gtttgtaact gctgctggga ttacacatgg catggatgaa ttgtacaagt aaagtgtgta     60
atcatatata taataaatga ggaataataa ttgaatagag atttaacgag tcgaagtttc    120
tgaaatatac gcacagttta tatttatgat tttgatatct aactacagtc ttctccatat    180
atttaactat aaataataaa gtatataact cttatgaaac tgtttcacca cattttttc     240 tacgggatcc ttcagtaatg tcttgtttct tttgttgcag tg                       282
```

<210> SEQ ID NO 43
<211> LENGTH: 53
<212> TYPE: DNA
<213> ORGANISM: Artificial Sequence
<220> FEATURE:
<223> OTHER INFORMATION: Primer

<400> SEQUENCE: 43

```
cacatggcat ggatgaattg tacaagtaat cgagataagc tgggggaaca ttc            53
```

<210> SEQ ID NO 44
<211> LENGTH: 79
<212> TYPE: DNA
<213> ORGANISM: Artificial Sequence
<220> FEATURE:
<223> OTHER INFORMATION: Primer

<400> SEQUENCE: 44
cactgcaaca aaagaaacaa gacattactg aaggatcctc gacaattaat atttacttat    60
tttggtcaac cccaaatag                                                  79

<210> SEQ ID NO 45
<211> LENGTH: 67
<212> TYPE: DNA
<213> ORGANISM: Artificial Sequence
<220> FEATURE:
<223> OTHER INFORMATION: Primer

<400> SEQUENCE: 45
cacatggcat ggatgaattg tacaagtaaa attgacacct tacgattatt tagagagtat    60
ttattag                                                               67

<210> SEQ ID NO 46
<211> LENGTH: 63
<212> TYPE: DNA
<213> ORGANISM: Artificial Sequence
<220> FEATURE:
<223> OTHER INFORMATION: Primer

<400> SEQUENCE: 46
cactgcaaca aaagaaacaa gacattactg aaggatcctg cagctaaggt aatcagatcc    60
aag                                                                   63

<210> SEQ ID NO 47
<211> LENGTH: 60
<212> TYPE: DNA
<213> ORGANISM: Artificial Sequence
<220> FEATURE:
<223> OTHER INFORMATION: Primer

<400> SEQUENCE: 47
catggcatgg atgaattgta caagtaagaa gagcagctgt aattatatta tcatgttagg    60

<210> SEQ ID NO 48
<211> LENGTH: 60
<212> TYPE: DNA
<213> ORGANISM: Artificial Sequence
<220> FEATURE:
<223> OTHER INFORMATION: Primer

<400> SEQUENCE: 48
cactgcaaca aaagaaacaa gacattactg aaggatcctg ccagagctgt cacatacttg    60

<210> SEQ ID NO 49
<211> LENGTH: 85
<212> TYPE: DNA
<213> ORGANISM: Artificial Sequence
<220> FEATURE:
<223> OTHER INFORMATION: Primer

<400> SEQUENCE: 49
cacatggcat ggatgaattg tacaagtaag gagtatacgt aaatatataa ttatatataa    60
tcatatatat gaatacaatg caatg                                           85

<210> SEQ ID NO 50
<211> LENGTH: 90
<212> TYPE: DNA
<213> ORGANISM: Artificial Sequence
<220> FEATURE:
<223> OTHER INFORMATION: Primer

```
<400> SEQUENCE: 50
cactgcaaca aaagaaacaa gacattactg aaggatccaa aataaattaa ataagttaaa      60
taaaattaag tgaataaagt ttcagaattg                                       90

<210> SEQ ID NO 51
<211> LENGTH: 53
<212> TYPE: DNA
<213> ORGANISM: Artificial Sequence
<220> FEATURE:
<223> OTHER INFORMATION: Primer

<400> SEQUENCE: 51
gcatggatga attgtacaag taaagtgtgt aatcatatat ataataaatg agg             53

<210> SEQ ID NO 52
<211> LENGTH: 55
<212> TYPE: DNA
<213> ORGANISM: Artificial Sequence
<220> FEATURE:
<223> OTHER INFORMATION: Primer

<400> SEQUENCE: 52
caaaagaaac aagacattac tgaaggatcc tttaattgta agtcttgact agagc           55

<210> SEQ ID NO 53
<211> LENGTH: 48
<212> TYPE: DNA
<213> ORGANISM: Artificial Sequence
<220> FEATURE:
<223> OTHER INFORMATION: Primer

<400> SEQUENCE: 53
caaaagaaac aagacattac tgaaggatcc tgattttggc ctgatgag                   48

<210> SEQ ID NO 54
<211> LENGTH: 90
<212> TYPE: DNA
<213> ORGANISM: Artificial Sequence
<220> FEATURE:
<223> OTHER INFORMATION: Primer

<400> SEQUENCE: 54
cataacactt gctctagtca agacttacaa ttaaaatgag aagagcgaat tcggcgcgcc      60
ggtaagatcc aaatcgatga attgaccaag                                       90

<210> SEQ ID NO 55
<211> LENGTH: 72
<212> TYPE: DNA
<213> ORGANISM: Artificial Sequence
<220> FEATURE:
<223> OTHER INFORMATION: Primer

<400> SEQUENCE: 55
gcaaatggca ttctgacatc ctcttgagcg gccgcttatg aagagctgtt caattgaggc      60
ttgaagtcga tg                                                          72

<210> SEQ ID NO 56
<211> LENGTH: 58
<212> TYPE: DNA
<213> ORGANISM: Artificial Sequence
<220> FEATURE:
<223> OTHER INFORMATION: Primer
```

```
<400> SEQUENCE: 56
tacacgtact tagtcgctga agctcttcta tggctagcaa aggagaagaa cttttcac        58

<210> SEQ ID NO 57
<211> LENGTH: 57
<212> TYPE: DNA
<213> ORGANISM: Artificial Sequence
<220> FEATURE:
<223> OTHER INFORMATION: Primer

<400> SEQUENCE: 57
aggtacgaac tcgattgacg gctcttcttt acttgtacaa ttcatccatg ccatgtg         57

<210> SEQ ID NO 58
<211> LENGTH: 67
<212> TYPE: DNA
<213> ORGANISM: Artificial Sequence
<220> FEATURE:
<223> OTHER INFORMATION: Primer

<400> SEQUENCE: 58
gctggtaact gcgtgcattt cgtcgcagag gaacaggact aatcgagata agctggggga     60
acattcg                                                                67

<210> SEQ ID NO 59
<211> LENGTH: 98
<212> TYPE: DNA
<213> ORGANISM: Artificial Sequence
<220> FEATURE:
<223> OTHER INFORMATION: Primer

<400> SEQUENCE: 59
ctacggggtc tgacgctcag tggtacctaa aaaaaatcct tagctttcgc taaggattcg     60
acaattaata tttacttatt ttggtcaacc ccaaatag                              98

<210> SEQ ID NO 60
<211> LENGTH: 98
<212> TYPE: DNA
<213> ORGANISM: Artificial Sequence
<220> FEATURE:
<223> OTHER INFORMATION: Primer

<400> SEQUENCE: 60
gctggtaact gcgtgcattt cgtcgcagag gaacaggact aaggagtata cgtaaatata     60
taattatata taatcatata tatgaataca atgcaatg                              98

<210> SEQ ID NO 61
<211> LENGTH: 109
<212> TYPE: DNA
<213> ORGANISM: Artificial Sequence
<220> FEATURE:
<223> OTHER INFORMATION: Primer

<400> SEQUENCE: 61
ctacggggtc tgacgctcag tggtacctaa aaaaaatcct tagctttcgc taaggataaa     60
ataaattaaa taagttaaat aaaattaagt gaataaagtt tcagaattg                 109

<210> SEQ ID NO 62
<211> LENGTH: 51
<212> TYPE: DNA
<213> ORGANISM: Artificial Sequence
<220> FEATURE:
<223> OTHER INFORMATION: Primer
```

<400> SEQUENCE: 62
ccttttgctc acatgtattt aaattttttg tagaaatgtc ttggtgtcct c    51

<210> SEQ ID NO 63
<211> LENGTH: 68
<212> TYPE: DNA
<213> ORGANISM: Artificial Sequence
<220> FEATURE:
<223> OTHER INFORMATION: Primer

<400> SEQUENCE: 63
gatttggatc ttaccggcgc gccgaattcg ctcttctcat tgtgttttga tagttgttca    60
attgattg    68

<210> SEQ ID NO 64
<211> LENGTH: 27
<212> TYPE: DNA
<213> ORGANISM: Artificial Sequence
<220> FEATURE:
<223> OTHER INFORMATION: Primer

<400> SEQUENCE: 64
tttaatttat ttgtccctat ttcaatc    27

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
aaaatgaagc ctgcatctct c    21

<210> SEQ ID NO 66
<211> LENGTH: 17
<212> TYPE: DNA
<213> ORGANISM: Artificial Sequence
<220> FEATURE:
<223> OTHER INFORMATION: Primer

<400> SEQUENCE: 66
aggcgaacac ctttccc    17

<210> SEQ ID NO 67
<211> LENGTH: 34
<212> TYPE: DNA
<213> ORGANISM: Artificial Sequence
<220> FEATURE:
<223> OTHER INFORMATION: Primer

<400> SEQUENCE: 67
aatgacaaaa aaaatcctat actatatagg ttac    34

<210> SEQ ID NO 68
<211> LENGTH: 19
<212> TYPE: DNA
<213> ORGANISM: Artificial Sequence
<220> FEATURE:
<223> OTHER INFORMATION: Primer

<400> SEQUENCE: 68
tgttcttccc agcattacg    19

<210> SEQ ID NO 69
<211> LENGTH: 27
<212> TYPE: DNA
<213> ORGANISM: Artificial Sequence
<220> FEATURE:
<223> OTHER INFORMATION: Primer

<400> SEQUENCE: 69
aggtctcact taatcttctg tactctg                                        27

<210> SEQ ID NO 70
<211> LENGTH: 30
<212> TYPE: DNA
<213> ORGANISM: Artificial Sequence
<220> FEATURE:
<223> OTHER INFORMATION: Primer

<400> SEQUENCE: 70
acatgtattt aaattttttg tagaaatgtc                                     30

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
cggtacattg ttgccatatg                                                20

<210> SEQ ID NO 72
<211> LENGTH: 3207
<212> TYPE: DNA
<213> ORGANISM: Artificial Sequence
<220> FEATURE:
<223> OTHER INFORMATION: Vector

<400> SEQUENCE: 72
atttaaattt tttgtagaaa tgtcttggtg tcctcgtcca atcaggtagc catctctgaa      60
atatctggct ccgttgcaac tccgaacgac ctgctggcaa cgtaaaattc tccggggtaa     120
aacttaaatg tggagtaatg gaaccagaaa cgtctcttcc cttctctctc cttccaccgc     180
ccgttaccgt ccctaggaaa ttttactctg ctggagagct tcttctacgg cccccttgca     240
gcaatgttct tcccagcatt acgttgcggg taaaacggag gtcgtgtacc cgacctagca     300
gcccagggat ggaaaagtcc cggccgtcgc tggcaataat agcgggcgga cgcatgtcat     360
gagattattg gaaaccacca gaatcgaata taaaaggcga acacctttcc caattttggt     420
ttctcctgac ccaaagactt taaatttaat ttatttgtcc ctatttcaat caattgaaca     480
actatcaaaa cacaatgaga gagcgaattc ggcgcgccg gtaagatcca aatcgatgaa     540
ttgaccaagc actacggtat gaagccagaa gactacactg ctgtcagatg tggtatgaat     600
gtcgccaagt acatcatcga agataagatt gatgctggta ttggtatcga atgtatgcaa     660
caagtcgaat ggaagagtta cttggccaag caaggcagac cagcttctga tgctaaaatg     720
ttgagaattg acaagttggc ttgctttggt tgctgttgtt tctgtaccgt tctttacatc     780
tgcaacgatg aattttgaa gaaaaccct gaaaaggtca gaagttcttg gaaagccatc      840
aagaaggcaa ccgactacgt tctagccgac cctgtgaagg cttggaaaga atacatcgac     900
ttcaagcctc aattgaacag ctcttcataa gcggccgctc aagaggatgt cagaatgcca     960
tttgcctgag agatgcaggc ttcatttttg atactttttt atttgtaacc tatatagtat    1020

```
aggattttttt ttgtcattttt gtttcttctc gtacgagctt gctcctgatc agcctatctc    1080
gcagcagatg aatatcttgt ggtaggggtt tgggaaaatc attcgagttt gatgttttc       1140 ttggtatttc ccactcctct tcagagtaca aagattaag tgagaccttc gtttgtgcgg       1200
atccttcagt aatgtcttgt ttcttttgtt gcagtggtga gccatttga cttcgtgaaa       1260 gtttctttag aatagttgtt tccagaggcc aaacattcca cccgtagtaa agtgcaagcg      1320
taggaagacc aagactggca taaatcaggt ataagtgtcg agcactggca ggtgatcttc      1380
tgaaagtttc tactagcaga taagatccag tagtcatgca tatggcaaca atgtaccgtg      1440
tggatctaag aacgcgtcct actaaccttc gcattcgttg gtccagtttg ttgttatcga      1500
tcaacgtgac aaggttgtcg attccgcgta agcatgcata cccaaggacg cctgttgcaa      1560
ttccaagtga gccagttcca acaatctttg taatattaga gcacttcatt gtgttgcgct      1620
tgaaagtaaa atgcgaacaa attaagagat aatctcgaaa ccgcgacttc aaacgccaat     1680
atgatgtgcg gcacacaata agcgttcata tccgctgggt gactttctcg ctttaaaaaa      1740
ttatccgaaa aaattttcta gagtgttgtt actttatact tccggctcgt ataatacgac      1800
aaggtgtaag gaggactaaa ccatggctaa actcacctct gctgttccag tcctgactgc      1860
tcgtgatgtt gctggtgctg ttgagttctg gactgataga ctcggttctct cccgtgactt     1920 cgtagaggac gactttgccg gtgttgtacg tgacgacgtt accctgttca tctccgcagt      1980
tcaggaccag gttgtgccag acaacactct ggcatgggta tgggttcgtg gtctggacga     2040
actgtacgct gagtggtctg aggtcgtgtc taccaacttc cgtgatgcat ctggtccagc      2100
tatgaccgag atcggtgaac agccctgggg tcgtgagttt gcactgcgtg atccagctgg      2160
taactgcgtg catttcgtcg cagaggaaca ggactaagga gtatacgtaa atatataatt      2220
atatataatc atatatatga atacaatgca atgaaagtga atatgataag attgaaataa      2280
taacaaacag cgataaatat atctcaaaat ggagttacac aacaaataat aataaaatat      2340
aaattataaa ttataaatta taaaagaata aaaaataaac cccactaatt tattttatta      2400
aaagatagat tggtatcttt acttaataac aattctgaaa ctttattcac ttaatttat      2460 ttaacttatt taatttattt tatccttagc gaaagctaag gattttttttt aggtaccact     2520 gagcgtcaga ccccgtagaa aagatcaaag gatcttcttg agatcctttt tttctgcgcg      2580
taatctgctg cttgcaaaca aaaaaaccac cgctaccagc ggtggtttgt ttgccggatc      2640
aagagctacc aactctttt ccgaaggtaa ctggcttcag cagagcgcag ataccaaata      2700
ctgttcttct agtgtagccg tagttaggcc accacttcaa gaactctgta gcaccgccta      2760
catacctcgc tctgctaatc ctgttaccag tggctgctgc cagtggcgat aagtcgtgtc      2820
ttaccgggtt ggactcaaga cgatagttac cggataaggc gcagcggtcg ggctgaacgg      2880
ggggttcgtg cacacagccc agcttggagc gaacgaccta caccgaactg agatacctac      2940
agcgtgagct atgagaaagc gccacgcttc ccgaagggag aaaggcggac aggtatccgg      3000
taagcggcag ggtcggaaca ggagagcgca cgagggagct tccaggggga aacgcctggt      3060
atctttatag tcctgtcggg tttcgccacc tctgacttga gcgtcgattt ttgtgatgct      3120
cgtcaggggg gcggagccta tggaaaaacg ccagcaacgc ggcctttta cggttcctgg      3180 ccttttgctg gccttttgct cacatgt                                           3207
```

<210> SEQ ID NO 73
<211> LENGTH: 22
<212> TYPE: DNA

<213> ORGANISM: Artificial Sequence
<220> FEATURE:
<223> OTHER INFORMATION: Primer

<400> SEQUENCE: 73
gacccttgtg actgacactt tg                                         22

<210> SEQ ID NO 74
<211> LENGTH: 30
<212> TYPE: DNA
<213> ORGANISM: Artificial Sequence
<220> FEATURE:
<223> OTHER INFORMATION: Primer

<400> SEQUENCE: 74
aggtctcact taatcttctg tactctgaag                                 30

<210> SEQ ID NO 75
<211> LENGTH: 21
<212> TYPE: DNA
<213> ORGANISM: Artificial Sequence
<220> FEATURE:
<223> OTHER INFORMATION: Primer

<400> SEQUENCE: 75 tcgattttg tgatgctcgt c                                           21

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
cggtacattg ttgccatatg c                                          21

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
taccagcggt ggtttgtttg                                            20

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
gcaaagtcgt cctctacgaa g                                          21

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
tcaagaggat gtcagaatgc                                            20

<210> SEQ ID NO 80
<211> LENGTH: 27
<212> TYPE: DNA
<213> ORGANISM: Artificial Sequence
<220> FEATURE:
<223> OTHER INFORMATION: Primer

<400> SEQUENCE: 80
acgggaagtc tttacagttt tagttag                                27

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
agaactgttg cagctccttc                                        20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
aacacggcta ccaccacctc                                        20

<210> SEQ ID NO 83
<211> LENGTH: 21
<212> TYPE: DNA
<213> ORGANISM: Artificial Sequence
<220> FEATURE:
<223> OTHER INFORMATION: Primer

<400> SEQUENCE: 83
tgcccccgtt aatacgacta c                                      21

<210> SEQ ID NO 84
<211> LENGTH: 26
<212> TYPE: DNA
<213> ORGANISM: Artificial Sequence
<220> FEATURE:
<223> OTHER INFORMATION: Primer

<400> SEQUENCE: 84
ctttgtgttt ttcatagtcg gctttg                                 26

<210> SEQ ID NO 85
<211> LENGTH: 6514
<212> TYPE: DNA
<213> ORGANISM: Artificial Sequence
<220> FEATURE:
<223> OTHER INFORMATION: Vector

<400> SEQUENCE: 85
agatccaatt cccgctttga ctgcctgaaa tctccatcgc ctacaatgat gacatttgga    60
tttggttgac tcatgttggt attgtgaaat agacgcagat cgggaacact gaaaaataca   120
cagttattat tcatttaaat gacccttgtg actgacactt tgggagtccc tattctactt   180
agtctcatat cgcatgaaac ttttgataaa ttatttctg ataggaattt ttcatcagat    240

-continued

```
attatcatcg cggcttacgt aataacaaaa aaaattgatg gagtctatac taggctaaca    300
taaactaagt tattaattaa acaaaacaaa acgtactagc attactgtca tatataaggg    360
ctcctaacta aaactgtaaa gacttcccgt gcggccgcct acttacctgg ggacaagctc    420
aatgattttt gagtatagtg gttgtgcaat gcttcgtgca taacggaaca agagaaaacg    480
tttccttgtt gccatctaga tttgtctaca gttagcttag aatacaagaa gaatgaacca    540
tcagaatcga ggactggagg ggtggttttg tagttattct caggttgtcc attagattcc    600
cattctaccg cgatatctga agggtaaaaa cctttcacca gacatgttag agaaacttgg    660
tttttagtca gttcgtccct cgaaggaggc aatgtgtaca cctgaggttc acgtggctga    720
cccttagctt tactaatagt cttttcaatt ggagcaggca gagctttgtt ggataccttc    780
cacttgtact ccttgccgtt cagccagtcc tggtggagaa cagtcaacac gctcactact    840
ctgtaggttg aattatattg ctcctctctt ggtttggttt tagcgttatg gacttcaaca    900
ccatcgacat accaattaaa tttcacttca ggatcctcgt gtgaaacgtc aacaacaaca    960
catgtgacct ctggcgttct gctgatcata agagtgtctt ttggcttggg cgggaaaaga   1020
aagactgagg gaccacctaa cagttcaggt gctgggcaag gtggacaagt atgggttttg   1080
tcgcaactct tcggttcaac ctttttatcg acctttgtat tacttggctt atggttaaca   1140
ttacaaatgt atgtctgagt acccaagctg gatgatggca cagtgaccac ggatgatagg   1200
gagtacaatc ctgagctttg caaaacggcg gggaatgtat gaacaccaga agttaaagct   1260
ccactattcc acgacacagt gactggttct gggaaatagt ctttaactaa acaacccaag   1320
gcagccgtac caccggatgt agacttggaa gaaggtgcaa gaggaaacac cgagggaccc   1380
tttgtggaag cggatgaaac tgtgacaagt gttccttgtc cccaataatc cattgcgtag   1440
aaaccatcac caccccatcg agaacaataa tagacagcag tgtcctcagc cctcaggcta   1500
ttcatctgca agtaagcagt gttttttagat gtatcagcag aaatagtaaa tctacccttta  1560 acactatcgg catatctagt atatccatta gtggggtata ttctggcaac ccactccaaa   1620
cctttaccag gagcttgtct aacccaatgg atgtatgtgt ccttgatgtt aaatccggag   1680
gcagcgcagg acaatctcag ggatccgcca ggctgcacta gaccaccacc tgattctacc   1740
agttgcacct cagcttcagc ctcacgcttt tccaaagaca cgccctcttc cttttgcagca   1800 attgatgcta tcgtagtatt gatgaataac aacccattat tcgtcgaatt actgaatggc   1860
aaaacagcaa cgtcaaagtc tccctctaaa tcggagtatc cgattacagc ctctgctggg   1920
atttgtgcgg tttcatcctc tgttgtagta ttcacagggg cagctaatgc ggacgatgct   1980
gcaaaaagta cagcggtgaa aatacttgga aaacgcattt ttgatgtttg atagtttgat   2040
aagagtgaac tttagtgttt agaggggtta aatttgttg taactggttt tggtcttaag    2100
ttaaaacgaa cttgttatat taaacacaac ggtcactcag gatacaagaa taggaaagaa   2160
aaactttaaa ctggggacat gttgtcttta tataatttgg cggttaaccc ttaatgcccg   2220
tttccgtctc ttcatgataa caaagctgcc catctatgac tgaatgtgga gaagtatcgg   2280
aacaaccctt cactaaggat atctaggcta aactcattcg cgccttagat ttctccaagg   2340
tatcggttaa gttcctcttt tcgtactggc taacgatggt gttgctcaac aaagggatgg   2400
aacggcagct aaagggagtg catggaatga ctttaattgg ctgagaaagt gttctatttg   2460
tccgaatttc ttttttctat tatctgttcg tttgggcgga tctctccagt ggggggtaaa   2520
tggaagattt ctgttcatgg ggtaaggaag ctgaaatcct tcgttttctta tagggggcaag   2580 tatactaaat ctcggaacat tgaatgtggt ttacttccat tggctacaga aattattaag   2640
```

| | |
|---|---|
| tttgttatgg ggtgaagtta ccagtaattt tcattttttc acttcaactt ttggggtatt | 2700 |
| tctgtggggt agcatagagc aatgatataa acaacaattg agtgacaggt ctactttgtt | 2760 |
| ctcaaaaggc cataaccatc tgtttgcatc tcttatcacc acaccatcct cctcatctgg | 2820 |
| ccttcaattg tggggaacaa ctagcatccc aacaccagac taactccacc cagatgaaac | 2880 |
| cagttgtcgc ttaccagtca atgaatgttg agctaacgtt ccttgaaact cgaatgatcc | 2940 |
| cagccttgct gcgtatcatc cctccgctat tccgccgctt gctccaacca tgtttccgcc | 3000 |
| ttttcgaac aagttcaaat acctatcttt ggcaggactt ttcctcctgc cttttttagc | 3060 |
| ctcaggtctc ggttagcctc taggcaaatt ctggtcttca tacctatatc aacttttcat | 3120 |
| cagatagcct ttgggttcaa aaagaacta agcaggatg cctgatatat aaatcccaga | 3180 |
| tgatctgctt ttgaaactat tttcagtatc ttgattcgtt tacttacaaa caactattgt | 3240 |
| tgatttatc tggagaataa tcgaacaaaa tgaggttccc gtctatcttt actgctgttt | 3300 |
| tgtttgccgc ttcgtccgct cttgctgccc ccgttaatac gactactgaa gatgagactg | 3360 |
| ctcaaattcc agctgaggca gtgatcggtt atagtgatct agaaggagac ttcgacgtgg | 3420 |
| ccgtcttgcc attctctaat tccacaaata acggcctttt gtttatcaat accacgatcg | 3480 |
| ccagcatcgc tgctaaggag gagggtgtat cactggagaa gagattgttt gactataaag | 3540 |
| atgatgatga taaaggaggt ggtggtagcc gtgttgacat acaaatgaca caatccccta | 3600 |
| gctccctgtc cgcatcagtc ggagataggg tcactattac atgtagagca tcgcaagacg | 3660 |
| tgaatactgc tgtagcatgg taccagcaaa agccaggtaa ggctcctaaa ctcctgattt | 3720 |
| actcagcatc ttttctttac tccggagttc catcgagatt cagtggcagt cgttctggta | 3780 |
| ccgactttac tttgacaatt tctagcttac agcctgagga tttcgctaca tactactgcc | 3840 |
| aacagcatta caccactcca cctactttg ggcaaggtac taaggtcgaa atcaagagaa | 3900 |
| ctgttgcagc tccttccgtt ttcattttc caccttcaga cgaacagcta aaaagtggta | 3960 |
| cagcatcagt ggtatgttta ctgaacaatt tctatccacg tgaagctaag gtccagtgga | 4020 |
| aagttgacaa tgcattgcaa tcaggtaact ctcaggaaag tgtgacagaa caagattcca | 4080 |
| aggatagcac ttactctttg tcctctacgt tgacattgtc caaagccgac tatgaaaaac | 4140 |
| acaaagttta tgcatgtgag gttacacatc aaggtttatc atctcccgtt accaaatcct | 4200 |
| tcaacagagg agaatgttaa gcggccgctc aagaggatgt cagaatgcca tttgcctgag | 4260 |
| agatgcaggc ttcattttg atactttttt atttgtaacc tatatagtat aggattttt | 4320 |
| ttgtcatttt gtttcttctc gtacgagctt gctcctgatc agcctatctc gcagcagatg | 4380 |
| aatatcttgt ggtaggggtt tgggaaaatc attcgagttt gatgttttc ttggtatttc | 4440 |
| ccactcctct tcagagtaca gaagattaag tgagaccttc gtttgtgcgg atccttcagt | 4500 |
| aatgtcttgt ttcttttgtt gcagtggtga gccattttga cttcgtgaaa gtttctttag | 4560 |
| aatagttgtt tccagaggcc aaacattcca cccgtagtaa agtgcaagcg taggaagacc | 4620 |
| aagactggca taaatcaggt ataagtgtcg agcactggca ggtgatcttc tgaaagtttc | 4680 |
| tactagcaga taagatccag tagtcatgca tatggcaaca atgtaccgtg tggatctaag | 4740 |
| aacgcgtcct actaaccttc gcattcgttg gtccagtttg ttgttatcga tcaacgtgac | 4800 |
| aaggttgtcg attccgcgta agcatgcata cccaaggacg cctgttgcaa ttccaagtga | 4860 |
| gccagttcca acaatctttg taatattaga gcacttcatt gtgttgcgct tgaaagtaaa | 4920 |
| atgcgaacaa attaagagat aatctcgaaa ccgcgacttc aaacgccaat atgatgtgcg | 4980 |

```
gcacacaata agcgttcata tccgctgggt gactttctcg ctttaaaaaa ttatccgaaa    5040
aaattttcta gagtgttgtt acttatact tccggctcgt ataatacgac aaggtgtaag    5100
gaggactaaa ccatggctaa actcacctct gctgttccag tcctgactgc tcgtgatgtt    5160
gctggtgctg ttgagttctg gactgataga ctccggtttct cccgtgactt cgtagaggac    5220
gactttgccg gtgttgtacg tgacgacgtt accctgttca tctccgcagt tcaggaccag    5280
gttgtgccag acaacactct ggcatgggta tgggttcgtg gtctggacga actgtacgct    5340
gagtggtctg aggtcgtgtc taccaacttc cgtgatgcat ctggtccagc tatgaccgag    5400
atcggtgaac agccctgggg tcgtgagttt gcactgcgtg atccagctgg taactgcgtg    5460
catttcgtcg cagaggaaca ggactaagga gtatacgtaa atatataatt atatataatc    5520
atatatatga atacaatgca atgaaagtga atatgataag attgaaataa taacaaacag    5580
cgataaatat atctcaaaat ggagttacac aacaaataat aataaaatat aaattataaa    5640
ttataaatta taaagaata aaaaataaac cccactaatt tatttttatta aaagatagat    5700 tggtatcttt acttaataac aattctgaaa ctttattcac ttaattttat ttaacttatt    5760
taatttattt tatccttagc gaaagctaag gattttttt aggtaccact gagcgtcaga    5820
ccccgtagaa aagatcaaag gatcttcttg agatcctttt tttctgcgcg taatctgctg    5880
cttgcaaaca aaaaaaccac cgctaccagc ggtggtttgt tgccggatc aagagctacc    5940 aactctttttt ccgaaggtaa ctggcttcag cagagcgcag ataccaaata ctgttcttct    6000
agtgtagccg tagttaggcc accacttcaa gaactctgta gcaccgccta catacctcgc    6060
tctgctaatc ctgttaccag tggctgctgc cagtggcgat aagtcgtgtc ttaccgggtt    6120
ggactcaaga cgatagttac cggataaggc gcagcggtcg ggctgaacgg ggggttcgtg    6180
cacacagccc agcttggagc gaacgaccta caccgaactg agatacctac agcgtgagct    6240
atgagaaagc gccacgcttc ccgaagggag aaaggcggac aggtatccgg taagcggcag    6300
ggtcggaaca ggagagcgca cgagggagct tccaggggga aacgcctggt atctttatag    6360
tcctgtcggg tttcgccacc tctgacttga gcgtcgattt ttgtgatgct cgtcaggggg    6420
gcggagccta tggaaaaacg ccagcaacgc ggcctttttta cggttcctgg ccttttgctg    6480
gccttttgct cacatgttct ttcctgcggt accc                                6514
```

<210> SEQ ID NO 86
<211> LENGTH: 6249
<212> TYPE: DNA
<213> ORGANISM: Artificial Sequence
<220> FEATURE:
<223> OTHER INFORMATION: Vector

<400> SEQUENCE: 86

```
agatccaatt cccgctttga ctgcctgaaa tctccatcgc ctacaatgat gacatttgga     60
tttggttgac tcatgttggt attgtgaaat agacgcagat cgggaacact gaaaaataca    120
cagttattat tcatttaaat gacccttgtg actgacactt tgggagtccc tattctactt    180
agtctcatat cgcatgaaac ttttgataaa ttattttctg ataggaattt ttcatcagat    240
attatcatcg cggcttacgt aataacaaaa aaaattgatg gagtctatac taggctaaca    300
taaactaagt tattaattaa acaaaacaaa acgtactagc attactgtca tatataaggg    360
ctcctaacta aaactgtaaa gacttcccgt gcggccgcct acttacctgg ggacaagctc    420
aatgattttt gagtatagtg gttgtgcaat gcttcgtgca taacgaaaca agagaaaacg    480
tttccttgtt gccatctaga tttgtctaca gttagcttag aatacaagaa gaatgaacca    540
```

```
tcagaatcga ggactggagg ggtggttttg tagttattct caggttgtcc attagattcc    600
cattctaccg cgatatctga agggtaaaaa cctttcacca gacatgttag agaaacttgg    660
tttttagtca gttcgtccct cgaaggaggc aatgtgtaca cctgaggttc acgtggctga    720
cccttagctt tactaatagt cttttcaatt ggagcaggca gagctttgtt ggatacctta    780
cacttgtact ccttgccgtt cagccagtcc tggtggagaa cagtcaacac gctcactact    840
ctgtaggttg aattatattg ctcctctctt ggtttggttt tagcgttatg gacttcaaca    900
ccatcgacat accaattaaa tttcacttca ggatcctcgt gtgaaacgtc aacaacaaca    960
catgtgacct ctggcgttct gctgatcata agagtgtctt ttggcttggg cgggaaaaga   1020
aagactgagg gaccacctaa cagttcaggt gctgggcaag gtggacaagt atgggttttg   1080
tcgcaactct tcggttcaac cttttttatcg acctttgtat tacttggctt atggttaaca   1140
ttacaaatgt atgtctgagt acccaagctg atgatggca cagtgaccac ggatgatagg    1200
gagtacaatc ctgagctttg caaaacggcg ggaatgtat aacaccaga agttaaagct    1260 ccactattcc acgacacagt gactggttct gggaaatagt ctttaactaa caacccaag    1320 gcagccgtac caccggatgt agacttggaa gaaggtgcaa gaggaaacac cgagggaccc   1380
tttgtggaag cggatgaaac tgtgacaagt gttccttgtc cccaataatc cattgcgtag   1440
aaaccatcac caccccatcg agaacaataa tagacagcag tgtcctcagc cctcaggcta   1500
ttcatctgca agtaagcagt gtttttagat gtatcagcag aaatagtaaa tctaccctta   1560
acactatcgg catatctagt atatccatta gtggggtata ttctggcaac ccactccaaa   1620
cctttaccag gagcttgtct aacccaatgg atgtatgtgt ccttgatgtt aaatccggag   1680
gcagcgcagg acaatctcag ggatccgcca ggctgcacta gaccaccacc tgattctacc   1740
agttgcacct cagcttcagc ctcacgcttt tccaaagaca cgccctcttc ctttgcagca   1800
attgatgcta tcgtagtatt gatgaataac aacccattat tcgtcgaatt actgaatggc   1860
aaaacagcaa cgtcaaagtc tccctctaaa tcggagtatc cgattacagc ctctgctggg   1920
atttgtgcgg tttcatcctc tgttgtagta ttcacagggg cagctaatgc ggacgatgct   1980
gcaaaaagta cagcggtgaa aatacttgga aaacgcattt taattgtaag tcttgactag   2040
agcaagtgtt atggtgaatt tcaagtaatt gaagtgctgg gtctacagct tatatatgat   2100
tttggcctga tgagcaacag aggctatcac cccgctggga taatgaaact taccgattgc   2160
ggcaggctaa gcgaaaagtc caggccaatc gagggaagtt aattgctcag ctttcctgac   2220
taatcccaac tttgaggggt gcatagtatg gattcggtct cgtgcgagaa gcttaaactt   2280
tgttcaattc cattagtaga gggtatcatg gaacttgcat gtgatgatta cttcatatga   2340
tatcaggtac tagcaatctc gattcgaatt tattaggtaa tgccgaccgg aacaatagaa   2400
agacttcaag attgctaaaa gaccaataag aacgtgtaca gatgtcaggc catgagttta   2460
tttaagtgat ctatgctaca attaaggtta caggagaacc gcattcggag ttcgattatt   2520
tttgtagaaa tgtcttggtg tcctcgtcca atcaggtagc catctctgaa atatctggct   2580
ccgttgcaac tccgaacgac ctgctggcaa cgtaaaattc tccggggtaa aacttaaatg   2640
tggagtaatg gaaccagaaa cgtctcttcc cttctctctc cttccaccgc ccgttaccgt   2700
ccctaggaaa ttttactctg ctggagagct tcttctacgg ccccctttgca gcaatgctct   2760 tcccagcatt acgttgcggg taaaacggag gtcgtgtacc cgacctagca gcccagggat   2820
ggaaaagtcc cggccgtcgc tggcaataat agcgggcgga cgcatgtcat gagattattg   2880
```

```
gaaaccacca gaatcgaata taaaaggcga acacctttcc caattttggt ttctcctgac    2940
ccaaagactt taaatttaat ttatttgtcc ctatttcaat caattgaaca actatcaaaa    3000
cacaatgagg ttcccgtcta tctttactgc tgttttgttt gccgcttcgt ccgctcttgc    3060 tgccccgtt aatacgacta ctgaagatga gactgctcaa attccagctg aggcagtgat    3120
cggttatagt gatctagaag gagacttcga cgtggccgtc ttgccattct ctaattccac    3180
aaataacggc cttttgttta tcaataccac gatcgccagc atcgctgcta aggaggaggg    3240
tgtatcactg gagaagagat tgtttgacta taaagatgat gatgataaag gaggtggtgg    3300
tagccgtgtt gacatacaaa tgacacaatc ccctagctcc ctgtccgcat cagtcggaga    3360
tagggtcact attacatgta gagcatcgca agacgtgaat actgctgtag catggtacca    3420
gcaaaagcca ggtaaggctc ctaaactcct gatttactca gcatctttc tttactccgg    3480 agttccatcg agattcagtg gcagtcgttc tggtaccgac tttactttga caatttctag    3540
cttacagcct gaggatttcg ctacatacta ctgccaacag cattacacca ctccacctac    3600
ttttgggcaa ggtactaagg tcgaaatcaa gagaactgtt gcagctcctt ccgttttcat    3660
ttttccacct tcagacgaac agctaaaaag tggtacagca tcagtggtat gtttactgaa    3720
caatttctat ccacgtgaag ctaaggtcca gtggaaagtt gacaatgcat tgcaatcagg    3780
taactctcag gaaagtgtga cagaacaaga ttccaaggat agcacttact ctttgtcctc    3840
tacgttgaca ttgtccaaag ccgactatga aaaacacaaa gtttatgcat gtgaggttac    3900
acatcaaggt ttatcatctc ccgttaccaa atccttcaac agaggagaat gttaagcggc    3960
cgctcaagag gatgtcagaa tgccatttgc ctgagagatg caggcttcat ttttgatact    4020 ttttatttg taacctatat agtataggat ttttttgtc attttgtttc ttctcgtacg    4080
agcttgctcc tgatcagcct atctcgcagc agatgaatat cttgtggtag gggtttggga    4140
aaatcattcg agtttgatgt ttttcttggt atttcccact cctcttcaga gtacagaaga    4200
ttaagtgaga cctttgttg tgcggatcct tcagtaatgt cttgtttctt ttgttgcagt    4260
ggtgagccat tttgacttcg tgaaagtttc tttagaatag ttgtttccag aggccaaaca    4320
ttccacccgt agtaaagtgc aagcgtagga agaccaagac tggcataaat caggtataag    4380
tgtcgagcac tggcaggtga tcttctgaaa gtttctacta gcagataaga tccagtagtc    4440
atgcatatgg caacaatgta ccgtgtggat ctaagaacgc gtcctactaa ccttcgcatt    4500
cgttggtcca gtttgttgtt atcgatcaac gtgacaaggt tgtcgattcc gcgtaagcat    4560
gcatacccaa ggacgcctgt tgcaattcca agtgagccag ttccaacaat ctttgtaata    4620
ttagagcact tcattgtgtt gcgcttgaaa gtaaaatgcg aacaaattaa gagataatct    4680
cgaaaccgcg acttcaaacg ccaatatgat gtgcggcaca caataagcgt tcatatccgc    4740
tgggtgactt tctcgcttta aaaaattatc cgaaaaaatt ttctagagtg ttgttacttt    4800
atacttccgg ctcgtataat acgacaaggt gtaaggagga ctaaaccatg gctaaactca    4860
cctctgctgt tccagtcctg actgctcgtg atgttgctgg tgctgttgag ttctggactg    4920
atagactcgg tttctcccgt gacttcgtag aggacgactt tgccggtgtt gtacgtgacg    4980
acgttaccct gttcatctcc gcagttcagg accaggttgt gccagacaac actctggcat    5040
gggtatgggt tcgtggtctg gacgaactgt acgctgagtg gtctgaggtc gtgtctacca    5100
acttccgtga tgcatctggt ccagctatga ccgagatcgg tgaacagccc tggggtcgtg    5160
agtttgcact gcgtgatcca gctggtaact gcgtgcattt cgtcgcagag gaacaggact    5220
aaggagtata cgtaaatata taattatata taatcatata tatgaataca atgcaatgaa    5280
```

-continued

```
agtgaatatg ataagattga aataataaca aacagcgata aatatatctc aaaatggagt    5340
tacacaacaa ataataataa aatataaatt ataaattata aattataaaa gaataaaaaa    5400
taaaccccac taatttattt tattaaaaga tagattggta tctttactta ataacaattc    5460
tgaaacttta ttcacttaat tttatttaac ttatttaatt tattttatcc ttagcgaaag    5520
ctaaggattt tttttaggta ccactgagcg tcagaccccg tagaaaagat caaaggatct    5580
tcttgagatc cttttttct  gcgcgtaatc tgctgcttgc aaacaaaaaa accaccgcta    5640
ccagcggtgg tttgtttgcc ggatcaagag ctaccaactc ttttccgaa  ggtaactggc    5700 ttcagcagag cgcagatacc aaatactgtt cttctagtgt agccgtagtt aggccaccac    5760
ttcaagaact ctgtagcacc gcctacatac ctcgctctgc taatcctgtt accagtggct    5820
gctgccagtg gcgataagtc gtgtcttacc gggttggact caagacgata gttaccggat    5880
aaggcgcagc ggtcgggctg aacggggggt tcgtgcacac agcccagctt ggagcgaacg    5940
acctacaccg aactgagata cctacagcgt gagctatgag aaagcgccac gcttcccgaa    6000
gggagaaagg cggacaggta tccggtaagc ggcagggtcg aacaggaga  gcgcacgagg    6060 gagcttccag ggggaaacgc ctggtatctt tatagtcctg tcgggtttcg ccacctctga    6120
cttgagcgtc gatttttgtg atgctcgtca gggggcgga  gcctatggaa aaacgccagc    6180
aacgcggcct ttttacggtt cctggccttt tgctggcctt ttgctcacat gttctttcct    6240
gcggtaccc                                                            6249
```

<210> SEQ ID NO 87
<211> LENGTH: 1863
<212> TYPE: DNA
<213> ORGANISM: Pichia pastoris

<400> SEQUENCE: 87

```
atgagtgttg tcagcaagca atacgacatc cacgaaggca ttatctttgt aattgaattg      60
accccggagc ttcacgcgcc ggcttcagaa gggaaatctc agctccagat catcttagag     120
aatgtcagtg aggttatttc tgagctaatc attaccttgc ccggtacagg aatagggtgt     180
taccttatta attacgacgg tggtcaaaac gacgaaattc accccatttt tgagttacaa     240
gacctgaatt tggaaatgat gaaacaattg taccaagtct tggaggacca tgtaagtggg     300
cttaatcctc tcgagaagca attcccaatt gaacacagta aaccgttatc agccactctg     360
ttctttcact taaggtctct ttttttacatg gcgaagactc ataagcgtac tggaagacat     420
tacaacttga aaaagatttt cttgttcact aataacgata aaccttacaa tggaaactct     480
cagctgagag ttcccttgaa gaaaaccctg gctgattaca atgacgtaga cattactttg     540
attccgtttc ttctgaacaa gccttcaggt gtcaagtttg acaagacgga atactcagaa     600
attttgttct atgataaaga tgcttgttcg atgtcaattg aggagatccg ccaacgaatt     660
tctagacata aggagatcaa gcgggtttac ttcacctgtc ctttgaaaat cgcaaataac     720
ttgtgcattt ctgtgaaagg ttattctatg ttttatcatg aaactccaag gaagatcaaa     780
tttgtcgtca atgagggttc aactttcaaa gatgtggaga caaatctcca gtttgtcgat     840
ccaacatccg gaaagagtt  ttccagtgaa cagctgatca agcatatcc  tctaggtgcc     900 gatgcttaca ttcctttaaa ctcagagcaa gtcaaaacaa taaatcgatt taatgatatc     960
atcaatatcc cctctttgga aattctaggt ttcaggata  tatctaattg gttgccacag    1020
tatcagtttg gcaaagcatc gttttatcc  cctaataact atggtgattt tacacattcg    1080
```

```
cagagaacat ttagttgtct tttacaatcc atgaccaaaa aatccaagtt tgcagtactt  1140
tttggtactt tgaagaacaa tgcggctcca aggttgtttg gcatgattcc ctctacgtta  1200
cctcaatacg aaagttgtaa tcttccccaa gggttcttcc tgataaagct cccgtatctg  1260
gatgatgtac gccagctgcc acccaaaatt gccccggtcg atgctgattt ggatgtatta  1320
gtttcacttt tcagcaacct ggtcggaaag atccacatca agaatggata ccaaccccaa  1380
gagtatgaaa atccttccct acaatggcac ttcaaaatgt tacgtgacga ttaccttcaa  1440
ttggaacacg atatcgacat cagtgacccc cttgagaaac aaaagtacat aaacagcctc  1500
gatgagacaa aaaccaagat catgaaacta cgggactatg tcaaggaaac tgccgatgat  1560
gacgaccctt cacggcttgc caacactctc aaagagctca accaagagct gaacaaaatt  1620
tccaactttg atatcatcgc caataagaag ccaaagaccc ccacgacagt agaccctgtt  1680
cctactgatg atgacatcat caacgcctgg aaggcaggaa ctctgaacgg tttcaaggtg  1740
gatcaattac gaaaatacgt aaggtcacga aacaactttc tggagacggc ctccaaaaag  1800
gcagatctca tcgccaacat tgacaagtac tttcagcaga agttcaaaga gactaaggcc  1860
tga                                                                1863
```

EPISOMAL PLASMID VECTORS

CROSS-REFERENCE TO RELATED APPLICATIONS

This application is the U.S. national stage of International Patent Application No. PCT/EP2016/073240, filed on Sep. 29, 2016 and entitled NOVEL EPISOMAL PLASMID VECTORS, which claims the benefit of priority under 35 U.S.C. § 119 from European Patent Application No. 15187431.0, filed Sep. 29, 2015. The disclosures of the foregoing applications are incorporated herein by reference in their entirety.

SEQUENCE LISTING

The entire content of a Sequence Listing titled "Sequence Listing.txt," created on Mar. 22, 2018 and having a size of 49 kilobytes, which has been submitted in electronic form in connection with the present application, is hereby incorporated by reference herein in its entirety.

FIELD OF THE INVENTION

The invention relates to episomal plasmid vectors comprising a gene of interest and an autonomously replicating sequence (ARS), and optionally further comprising a promoter and a selection marker, and methods of using said plasmid vectors for expression of proteins of interest and/or protein, promoter and metabolic pathway engineering.

BACKGROUND

Many industrially relevant proteins such as biocatalysts and also biopharmaceuticals are produced by heterologous gene expression. The yeast *Pichia pastoris* has emerged as one of the most commonly used microbial host systems for heterologous protein production due to its feasibility for high cell density bioreactor cultivations, high secretory capacities and strong promoters (Ahmad, et al. 2014; Gasser et al. 2013). Recent taxonomy studies lead to the conclusion, that the commonly named *Pichia pastoris* includes several different species such as *Komagataella pastoris* and the most commonly used *Komagataella phaffii* strains NRLL Y-11430, CBS7435, BG10, and mutants thereof such as for example BG11, and GS115, X33 and KM71. Most commonly the methanol inducible promoter of the alcohol oxidase 1 gene ($P_{AOX1}$) is used to drive expression of heterologous genes (Vogl and Glieder, 2013). $P_{AOX1}$ is tightly repressed on carbon sources such as glucose and glycerol and approximately 1000-fold induced by methanol. This tight regulation allows to separate cell growth from heterologous protein production: At first *P. pastoris* is typically cultivated on glycerol to obtain a high cell density and subsequently induced with methanol to initiate expression of the gene of interest (GOI). Thereby even detrimental or toxic proteins can be produced. However, methanol is toxic and flammable making its use especially in large scale bioreactors undesirable.

Recently it was shown that the promoter of the catalase 1 gene ($P_{CAT1}$) provides a distinct regulatory profile. $P_{CAT1}$ is similar to $P_{AOX1}$ tightly repressed on glucose or glycerol, but does not require methanol induction. Expression starts once the carbon source in the medium is used up ('derepression' (Hartner et al. 2008)) reaching approximately 30 to 40% of the space time yields (depending on the GOI) of methanol induced $P_{AOX1}$ in small scale cultivations. This catalase gene was also described as the gene of the peroxisomal catalase cta1. $P_{CAT1}$ can also be induced with methanol and oleic acid reaching similar expression levels as $P_{AOX1}$. The derepressed regulatory profile allows methanol-free production, as the derepression phase can be maintained by feeding limiting amounts of glycerol or glucose in bioreactors as demonstrated with synthetic $P_{AOX1}$ variants (Hartner et al. 2008). EP2862933A2 discloses a library of bidirectional expression cassettes and described several promoter sequences of *Pichia pastoris*, including the sequence for the promoter sequence of the peroxisomal catalase gene CAT1.

Expression cassettes are typically integrated into the genome of methylotrophic yeasts, resulting in strains stable even under non-selective conditions. For example, Yurimoto et al. (Yurimoto et al. 2001) describe D-amino acid oxidase expression under the control of the promoter of the AOD1 gene integrated at the ura3 locus in *C. boidinii*. Episomal plasmids are lost upon growth under non-selective conditions. In yeasts, the autonomously replicating sequence (ARS) is necessary for stable maintenance of episomal plasmids. Structure and position of yeast origins of replication were studied (Chen et al. 1996, Peng Chong et al. 2015) and various ARS sequences were identified (Liachko et al. 2014A, Liachko et al. 2014B, Sohn et al. 1996). Episomal plasmids have been very rarely used for heterologous protein expression in *P. pastoris* and other methylotrophic yeasts, due to low stability and low expression rates. A few applications of episomal expression have recently been reported and these constructs are capable of expressing detectable amounts of protein. For example, Lee et al. (Lee et al. 2001) report an episomal vector comprising an ARS, namely PARS 1, and the promoter pGAP driving a gene of interest and a selection marker. The vector is used in *P. pastoris* to screen a library of gene of interest mutants. However, there remains a need for episomal plasmid vectors with high transformation efficiency, which are stably maintained in transformed cells and enable high protein yields. In addition reliable expression giving highly reproducible product yields with low clonal variation is a desirable feature for engineering strategies including screening of variant libraries. Furthermore such episomal plasmids should be small in order to facilitate cloning and to obtain high transformation rates.

Furthermore, transformation methods typically applied in *Pichia pastoris*, namely transformation with linear DNA for integration into the genome or with supercoiled, circular ARS plasmids for episomal replication, are generally not very suitable for the screening of libraries, since the libraries need to be cloned into the expression vectors prior transformation and an efficient cloning method needs to be used to ensure that the diversity is not lost.

In vivo recombination of co-transformed fragments, i.e. homologous recombination cloning (HR cloning) can be used to build the final expression vector within a cell. This method was not used in *Pichia pastoris* until recently, since the stability of plasmids in *P. pastoris* and homologous recombination in vivo was inefficient. It was recently reported that ARS plasmids offer an alternative strategy exploiting the yeast's recombination machinery for cloning. It was shown that HR cloning was successful by employing a panARS-based episomal vectors in *Pichia pastoris* (Camattari et al. 2016) and a split marker gene to avoid a high background from inefficient homologous recombination. Although this method and vectors allow the cloning of DNA fragments, the efficiency and flexibility in molecular design is quite limited.

In contrast, *S. cerevisiae* is known as an efficient host for cloning by in vivo recombination and HR cloning has been used in *Saccharomyces* to clone genes of interest into expression vectors (Oldenburg et al. 1997) and also for cloning of multiple fragments or assembly of whole vectors from multiple PCR products (van Leeuwen et al. 2015, Joska et al. 2014). Due to its high efficiency and easy application it has also been used for the creation of libraries (Vina-Gonzalez et al. 2016) or creation of chimeric DNA (Arenhart et al. 2016).

SUMMARY OF THE INVENTION

Autonomously replicating sequences (ARS) with unprecedented technological features were identified. Surprisingly the identified ARS were found as parts of DNA elements which were tested as putative promoter sequences. Episomal plasmid vectors comprising said ARSs, a gene of interest operably linked to a promoter and a selection marker were more efficiently transformed compared to linear expression cassettes comprising said gene of interest, promoter and selection marker. If used under selective conditions, the plasmid vectors described herein resulted several-fold increased expression compared to genomic integration. Furthermore transformation rates were increased and the transformants showed more uniform expression and the employed ARS showed additional functionality as transcription terminators. Surprisingly a heterologous sequence from *Candida boidinii* showed the best technological features—better than any previously known endogenous ARS. The plasmid vectors described herein may be used in methods of protein expression as well as for screening large libraries required for protein or promoter engineering and discovery.

It was surprising that highly efficient library generation can be achieved by in vivo homologous recombination in *Pichia pastoris* using efficient CbARS based vector backbones (i.e. vector backbones comprising an ARS sequence of *Candida boidinii*) in combination with a KU70 *Pichia pastoris* deletion strain and relatively high amounts of DNA with a certain molar ratio (insert:vector backbone) without observing significant background when employing the CbARS-based vector backbone alone. Surprisingly no split selection marker was needed for such highly efficient approach for library construction with maximal flexibility in molecular design, allowing to design homologous recombination sites in any region of the vector backbone.

Specifically, the invention provides for an episomal plasmid comprising a gene of interest (GOI) and an autonomously replicating sequence (ARS) which is not operably linked to the GOI, which ARS comprises or consists of a nucleotide sequence identified as any of SEQ ID NO:2, SEQ ID NO:3, SEQ ID NO:5, or SEQ ID NO:6-11, or a functionally active variant of any of the foregoing which is characterized by at least 60% sequence identity thereto, specifically at least any of 70%, 80%, 90%, or 95% sequence identity. The episomal plasmid is also referred to as plasmid which is defined by the structural features as claimed or further described herein, which is characterized by its function of being episomally replicable in a host cell, e.g. in *Pichia*.

Specifically, the ARS is not natively associated with the GOI.

Specifically, the ARS and/or the GOI is a nucleotide sequence which is heterologous to the plasmid. Specifically, both, the ARS and the GOI are heterologous sequences, more specifically from different sources, strains or species.

According to a specific aspect, the ARS and/or the GOI are also heterologous to a host cell, which has been engineered to synthesize the episomal plasmid in the host cell, or to introduce the episomal plasmid into the host cell, or which comprises the episomal plasmid and is cultivated in a host cell culture expressing or otherwise displaying the GOI.

The ARS consisting of the nucleotide sequence identified as SEQ ID NO:3 is a functionally active fragment of SEQ ID NO:2. Therefore, the functional variants of SEQ ID NO:2 shall also include fragments of SEQ ID NO:2 which are at least comprising SEQ ID NO:3.

The ARS consisting of the nucleotide sequence identified as any of SEQ ID NO:6-11 is an exemplary functionally active variant of SEQ ID NO:5. Further functionally active variants are feasible which are characterized by the specified sequence identity to SEQ ID NO:5.

Specifically, the episomal plasmid further comprises a selection marker and optionally one or more regulatory sequences. Specifically a selection marker is used, which indicates or regulates the expression of the GOI. Regulatory sequences are particularly preferred which are suitable for expressing the GOI.

Specific regulatory sequences confer termination of transcription of the GOI. Specifically, the ARS confers termination of transcription of the GOI.

Specifically, the episomal plasmid comprises the ARS sequence, a promoter sequence separate from the ARS, and a transcriptional terminator sequence, which are arranged overlappingly over less than 700 base pairs, preferably over less than 500 base pairs, more preferably over less than 300 base pairs.

Specifically, the episomal plasmid comprises an expression cassette comprising the GOI and regulatory sequences required for expressing said GOI.

Specifically, the episomal plasmid comprises a promoter which is operably linked to the GOI. Specifically, the promoter is not adjacent to the ARS and/or in an expression cassette separate from the ARS.

Specifically, the promoter is a regulatable or constitutive promoter, preferably a promoter selected from the group consisting of AOX1, GAP, AOD, AOX2, DAS1, DAS2, ENO1, FLD1, FMD, GPM1, HSP82, ICL1, ILV5, KAR2, KEX2, PET9, PEX8, PGK1, PHO89/NSP, SSA4, TEF1, THI11, TPI1, YPT1, GTH1, GCW14, and GUT1, which promoter is preferably of a yeast, in particular of a *Pichia pastoris* strain, or a functional variant of any of the foregoing which is characterized by at least 60% sequence identity, specifically at least any of 70%, 80%, 90%, or 95% sequence identity, and functional as a promoter in a *P. pastoris* strain. Specifically, the promoter is an analogue of the *P. pastoris* promoter naturally occurring in another yeast or species, or a fully synthetic promoter.

Specifically, the episomal plasmid comprises the ARS consisting of SEQ ID NO:6 and a promoter selected from the group consisting of CAT1, AOX, histone promoters, GAP and DAS promoters, and a heterologous GOI.

Specifically, the promoter is a carbon source regulatable promoter, preferably a promoter derepressed upon glucose depletion, or inducible upon feeding a cell culture with an inducer, such as a carbon source. Specifically, the promoter is inducible with oleic acid.

Specifically, the promoter is a CAT1 or AOD promoter.

Specifically, the promoter comprises the nucleotide sequence of any of SEQ ID NO:4, or SEQ ID NO:5, or a functional variant characterized by a sequence identity of at least 60% of any of SEQ ID NO:4, or SEQ ID NO:5, specifically at least any of 70%, 80%, 90%, or 95% sequence identity.

Specifically, the episomal plasmid comprises a selection marker that is based on auxotrophy or chemical resistance, preferably wherein the selection marker is based on glycerol utilization, sucrose utilization, inulin utilization, cellobiose utilization, amino acid auxotrophy, thymidine auxotrophy, nitrogen source utilization, resistance to fluoracetamide, resistance to deoxyglucose, resistance to Zeocin or other antibiotics, resistance to a gene encoding a toxin. The selection marker provides for cultivating a host cell that comprises the episomal plasmid described herein, under selective pressure or under selective conditions, e.g., to select those host cells or plasmid comprising the GOI.

Specifically, the selection marker confers resistance to zeocin, geneticin or glycerol utilization.

According to a specific aspect, a eukaryotic host cell is provided which comprises the episomal plasmid described herein.

Specifically, the host cell is a yeast cell, preferably of the *Pichia* genus, preferably of *Pichia pastoris*, which is a wild-type strain or any mutated strain capable of being cultivated in a cell culture. Specifically, the mutated strain is a ku70 deletion strain of *P. pastoris*, wherein the ku70 gene (SEQ ID NO:87, identified in FIG. 33) or an analogous ku70 gene is inactivated or inhibited. Specifically, mutated *P. pastoris* strains which are deficient in the ku70 gene expression are preferred for biosynthesis and production of episomal plasmids and libraries of episomal plasmids as described herein.

Specifically, the host cell is provided in a cell culture wherein the host cells are characterized by a genomic stability regarding the content of the episomal plasmid during at least 20 generations. Therefore, according to a specific aspect, the cell culture of the host cell described herein is provided in a fermenter and device, suitably used for batch, fed-batch, or continuous cultivation.

According to a further aspect, the invention provides for a method of producing a protein of interest (POI) that is encoded by a GOI by cultivating the host cell described herein under conditions to express said GOI. Specifically, the host cell is cultivated under selective conditions. Specifically, in the cell culture, protein expression is regulatable by the carbon source and/or the feed rate thereof.

Specifically, the POI expression is increased at least 1.5 fold, preferably at least 3 fold, more preferably at least 5 fold or at least 10 fold, compared to the POI expression employing genomic integration of the comparable expression cassette expressing said GOI, which does not contain a functional ARS, such as comprised in the episomal plasmid described herein.

Specifically, the transformation efficiency of the episomal plasmid is increased at least 20 fold or at least 50 fold, preferably at least 100 fold, at least 200 fold, or at least 300 fold, more preferably at least 500 fold compared to transformation employing genomic integration of the comparable expression cassette expressing said GOI, which does not contain a functional ARS, such as comprised in the episomal plasmid described herein.

According to a further aspect, the invention provides for a library of episomal plasmids described herein, which comprises a repertoire of promoter variants and/or a repertoire of GOI variants, which are optionally coexpressed in a host cell culture.

Specifically, the promoter library may be used to discover variants of a parent promoter sequences with desired or improved properties.

Specifically a GOI library may be used to discover gene variants or a parent GOI sequence encoding variants of proteins or polypeptides with desired or improved properties.

The library may be provided as an in vitro library, or as a library of (ex vivo) host cells comprising the repertoire of episomal plasmids, which host cells may be of any eukaryotic or prokaryotic species.

According to a further aspect, the invention provides for a method of selecting a host cell for a desired yield of a GOI expression, the method comprising:

i. contacting a plurality of host cells comprising the library of episomal plasmids described herein, wherein the library comprises a repertoire of promoter variants and wherein the expression level of said GOI is a function of said promoter variants;

ii. determining the expression level in individual host cells of said plurality; and iii. selecting a host cell which is characterized by the desired expression level of said GOI.

Specifically, the method further comprises cultivating the selected host cell and producing a POI encoded by said GOI.

According to a further aspect, the invention provides for a method of screening promoter variants from a repertoire of promoter variants, and selecting a promoter, the method comprising:

i. contacting a plurality of host cells comprising the library of episomal plasmids described herein, wherein the library comprises a repertoire of promoter variants and a reporter protein wherein any of the expression level of said reporter protein, transformation efficiency or clonal uniformity is a function of said promoter variants;

ii. determining changes in any of the expression level, transformation efficiency or clonal uniformity in individual host cells of said plurality;

iii. selecting a host cell which is characterized by the desired expression level, transformation efficiency or clonal uniformity; and iv. identifying the promoter variant from the selected host cell.

According to a further aspect, the invention provides for a method of screening variants of a POI encoded by a repertoire of GOI variants, the method comprising i. contacting a plurality of host cells comprising the library of episomal plasmids described herein, wherein the library comprises a repertoire of GOI variants and wherein any of the GOI expression level, transformation efficiency or clonal uniformity is a function of GOI variants;

ii. determining changes in any of the expression level, transformation efficiency or clonal uniformity in individual host cells of said plurality;

iii. selecting a host cell which is characterized by the desired expression level, transformation efficiency or clonal uniformity; and iv. identifying the GOI variant from the selected host cell.

According to a further aspect, the invention provides for a method of biosynthesis of an episomal plasmid in a host cell which is of a KU70 deletion strain of *Pichia pastoris*, comprising i. providing a linear vector backbone comprising recombination sites at its 5' and 3' ends, an ARS, and optionally further regulatory sequences;

ii. providing a vector insert comprising a GOI and 5' and 3' homologous sequences which are homologous to said recombination sites;

iii. introducing said linear vector backbone and said insert into said host cell and recombining said vector insert with said recombination sites by homologous recombination, thereby producing the episomal plasmid comprising said GOI.

Specifically, said linear vector backbone and said insert are introduced into said host cell at a molar ratio between 1:1 and 1:10.

Specifically, the ARS comprises or consists of a nucleotide sequence identified as any of SEQ ID NO:2, SEQ ID NO:3, SEQ ID NO:5, or SEQ ID NO:6-11, or a functionally active variant of any of the foregoing which is characterized by at least 60% sequence identity thereto, specifically at least any of 70%, 80%, 90%, or 95% sequence identity.

Specifically, the vector backbone further comprises a selection marker, which is based on auxotrophy or chemical resistance, preferably wherein the selection marker is based on glycerol utilization, sucrose utilization, inulin utilization, cellobiose utilization, amino acid auxotrophy, thymidine auxotrophy, nitrogen source utilization, resistance to fluoracetamide, resistance to deoxyglucose, resistance to Zeocin or other antibiotics, resistance to a gene encoding a toxin.

Specifically, the 5' and 3' homologous sequences each comprise or consist of at least any one of 30, 50, 70, 100, 300 base pairs.

Specifically, the 5' and 3' homologous sequences are flanking the GOI or adjacent to the 5' and 3' end of the GOI.

Specifically, the 5' and 3' homologous sequences are located at both ends of the insert, or fused to the 5' and 3' end of the insert core sequence (which is without the 5' and 3' homologous sequences).

According to a further aspect, the invention provides for the use of the biosynthesis method described herein for producing an episomal plasmid described herein.

According to a further aspect, the invention provides for a episomal plasmid obtained by any one of the biosynthesis methods described herein.

According to a further aspect, the invention provides for a method of producing a library of episomal plasmids using the biosynthesis method described herein, wherein the library comprises a repertoire of plasmid variants which differ in at least one point mutation in a predefined region of the GOI. The predefined region is typically a region which is varied by a suitable mutagenesis method (also referred to as region of mutagenesis).

Specifically, the variants are produced by mutagenesis of the vector inserts, in particular mutagenesis of the region of mutagenesis.

According to a further aspect, the invention provides for a library of episomal plasmids obtained by the method described herein, which is characterized by a diversity of at least any of 10E2, 10E3, 10E4, 10E5, or 10E6 different variants. In certain embodiments, even a higher diversity can be produced, e.g. at least any of 10E7, 10E8, 10E9, 10E10, or 10E11 different variants.

Specifically, the library is incorporated into at least 10E6 transformed cells, preferably at least 10E7, 10E8, or 10E9 transformants. In certain embodiments, even a higher number of transformants can be produced, such as to cover the repertoire of episomal plasmid variants.

Specifically, the transformed cells are of the *Pichia* genus, preferably *P. pastoris*, or a KU70 deletion strain of *P. pastoris*.

According to a specific aspect, the GOI is encoding an antibody, an antibody fragment or antigen-binding sequence thereof, such as a scFv, Fab, VH and/or VL, a single CDR sequence or a set of CDR sequences, e.g. 3 CDR sequences. Specifically, GOI variants are produced by mutagenesis of one or more variable regions or antigen-binding sequences, such as to produce a repertoire of antigen-binding molecules which differ in at least one of epitope specificity or affinity of binding. Alternatively, GOI variants are produced by mutagenesis of one or more constant or framework sequences, such as to improve the stability or Fc function of the antigen-binding molecules.

Specifically, an antibody library is provided, which is characterized by the repertoire of GOI variants, each encoding an antibody or antigen-binding sequence thereof.

Specifically, the library is expressing a repertoire of POI variants, each representing an antibody or antigen-binding sequence thereof. The library is suitably expressed by in vitro, ex vivo or in vivo expression systems, e.g. in a suitable host cell culture. Upon expression, the POI variants can be screened for selecting a POI variant with desired binding or other features.

FIGURES

FIG. 1: The upstream region of the CAT1 gene contains an AT-rich ARS which does not affect regulation or expression strength. (A) The genomic locus of the *P. pastoris* CAT1 gene is shown with gene annotations based on the sequencing of the CBS7435 strain (Küberl et al. 2011). An ARS identified by high throughput deep sequencing (ARS-seq) by Liachko et al. (Liachko et al. 2014) is shown. The AT content was calculated with a sliding window of 50 bp using BitGene (WorldWideWeb: bitgene.com/cgi/gene_analysis.cgi). The promoter sequences ($P_{CAT1-1000}$, $P_{CAT1-692}$ and $P_{CAT1-500}$) and the putative ARS of $P_{CAT1}$ (putARS-$P_{CAT1}$, selected based on AT content) used in this study are indicated. (B) The promoter lengths indicated were cloned upstream of an eGFP reporter gene, and stable genomic *P. pastoris* transformants were cultivated in shake flasks. Reporter protein fluorescence, $OD_{600}$ and glucose concentrations were measured at the time points indicated. Mean values and standard deviations of biological triplicates are shown. Cultures were induced with methanol after 48 h. At 0 h the flasks were inoculated to an $OD_{600}$ of 0.05 and first measurements performed when the exponential growth phase was reached. The x-axis is broken between 1 and 14 h.

FIG. 2: The ARS of $P_{CAT1}$ causes background growth and is unstable under non-selective conditions. (A) Picture of agar plates after transformation of *P. pastoris* cells with circular or linearized plasmids containing the indicated lengths of $P_{CAT1}$. The empty vector control is the unmodified pPpT4_S vector (Näätsaari et al. 2012) not containing $P_{CAT1}$. The circular plasmids showed higher transformation rates, therefore only 10 ng were transformed and the whole transformation reaction plated. For linear plasmids, 1 μg was transformed and one fifth of the transformation reaction plated. (B) Evaluating plasmid stability by determining growth on selective (YPD+Zeo) and non-selective (YPD) media from liquid culture. Four colonies of transformants (T1-T4) of the indicated plasmids and colony sizes were inoculated in liquid culture under selective (YPD+Zeo) and non-selective (YPD) conditions for 60 h and subsequently stamped (diluted 1:1000) on selective and non-selective agar plates. The empty pPpT4_S vector is included as control for stable genomic integration, the wildtype strain to test Zeocin selection. (C) Stability of single colony separated transformants under selective and non-selective conditions. Single colonies from four transformants (T1-T4) of $P_{CAT1-692}$ (as a representative ARS containing plasmid) and $P_{CAT1-500}$ (ARS free control) were re-streaked on selective (YPD+Zeocin) and non-selective conditions (YPD). Subsequently single colonies were streaked adjacently on selective media to monitor plasmid loss by growth (picture after 48 h incubation at 28° C.). In case of $P_{CAT1-692}$ transformants of linearized vector (big and small colonies) and circular plasmid were used.

FIG. 3: Episomal replicating plasmids containing the ARS of $P_{CAT1}$ show increased expression under selective pressure compared to genomic integration. Reporter protein fluorescence of the indicated plasmids and colony sizes was measured with the selection markers (A) Zeocin (B) Geneticin and (C) GUT1 complementation. The strains were grown in selective (YPD+Zeo/Gen; BMG (buffered minimal glycerol) and non-selective (YPD, BMD (buffered minimal dextrose)) media for 60 h (see also FIG. 2B). The empty vector controls are: for Zeocin pPpT4_S, for Geneticin pPpKan_S, and for glycerol auxotrophy pPpGUT1 (Näätsaari et al. 2012). For GUT1 complementation selection, also the auxotrophic parental strain was included. Mean values and standard deviations of seven different transformants are shown. In case of Geneticin selection, barely any growth differences were noticeable between colonies (see picture in FIG. S3), therefore the big and small colonies indicated are only putative. Due to the high standard deviation, for putative big colonies of $P_{CAT1-692}$ on Geneticin, also the fluorescence value of each single transformant is shown as an inlet.

FIG. 4: The combination of the CAT1-692 promoter and its endogenous ARS gives up to 4.9-fold higher yields for the biocatalysts MeHNL and LuHNL and the transformants show up 3.5-fold more uniform expression. MeHNL (A,B) and LuHNL (C,D) were expressed from a circular plasmid bearing the $P_{CAT1-692}$ (A,C) or a linearized plasmid bearing $P_{CAT1-500}$ (B,D). MeHNL and LuHNL activity were measured after growth under selective conditions (glycerol) for 60 h. LuHNL cultivation were supplemented with zinc sulfate required for folding. Forty-two transformants were compared per construct after growth in 96 well deep well plates on glycerol for 60 h. The mean value (MV) and standard deviation (SD) of all transformants per construct are shown on the left side of each panel. The SD is also provided as percent of the MV.

Figures 5, 6A:
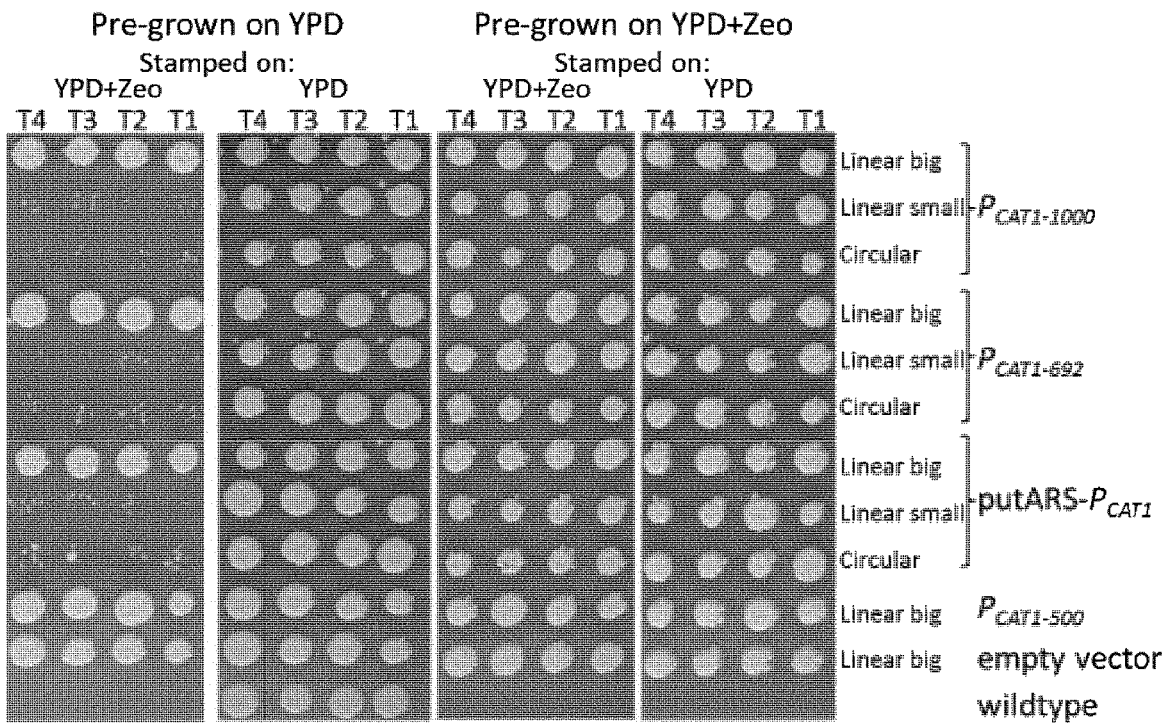

FIG. 5: $P_{CAT1}$-692 episomal plasmid vectors in P. pastoris show approximately 108 fold higher transformation efficiencies than linear cassettes targeting genomic integration. Ten ng of the circular ARS plasmids $P_{CAT1-692}$ and approximately 1 μg of the $P_{CAT1-500}$ plasmids (linearized to target genomic integration) were transformed. Transformation efficiencies were calculated as colony forming units (cfu) per μg DNA. Mean value and standard deviations of quadruplicates for ARS plasmids and genomic integration were calculated (single values of the transformation of MeHNL and LuHNL constructs are shown as well).

FIG. 6: Effects of plasmid loss are even more severe when inoculated from glycerol stock. (A) The same experiment as shown in FIG. 2B was repeated with inoculation from 96 well glycerol stocks. Glycerol stocks in 96 well microtiter plates of the YPD cultivations shown in FIG. 2B and FIG. 3A were used to inoculate selective (YPD+Zeo) and non-selective (YPD) media. Therefore the same transformants (T1-T4) shown in FIG. 2B of the indicated plasmids and colony sizes were used. After cultivation for 60 h the cultivations were diluted 1:1000 and stamped on selective and non-selective agar plates. The empty pPpT4_S vector is included as control for stable genomic integration, the wildtype strain to test Zeocin selection. (B) Fluorescence measurements of the cultivations described in panel A, identical FIG. 3A except being inoculated from glycerol stocks.

Figure 7A:
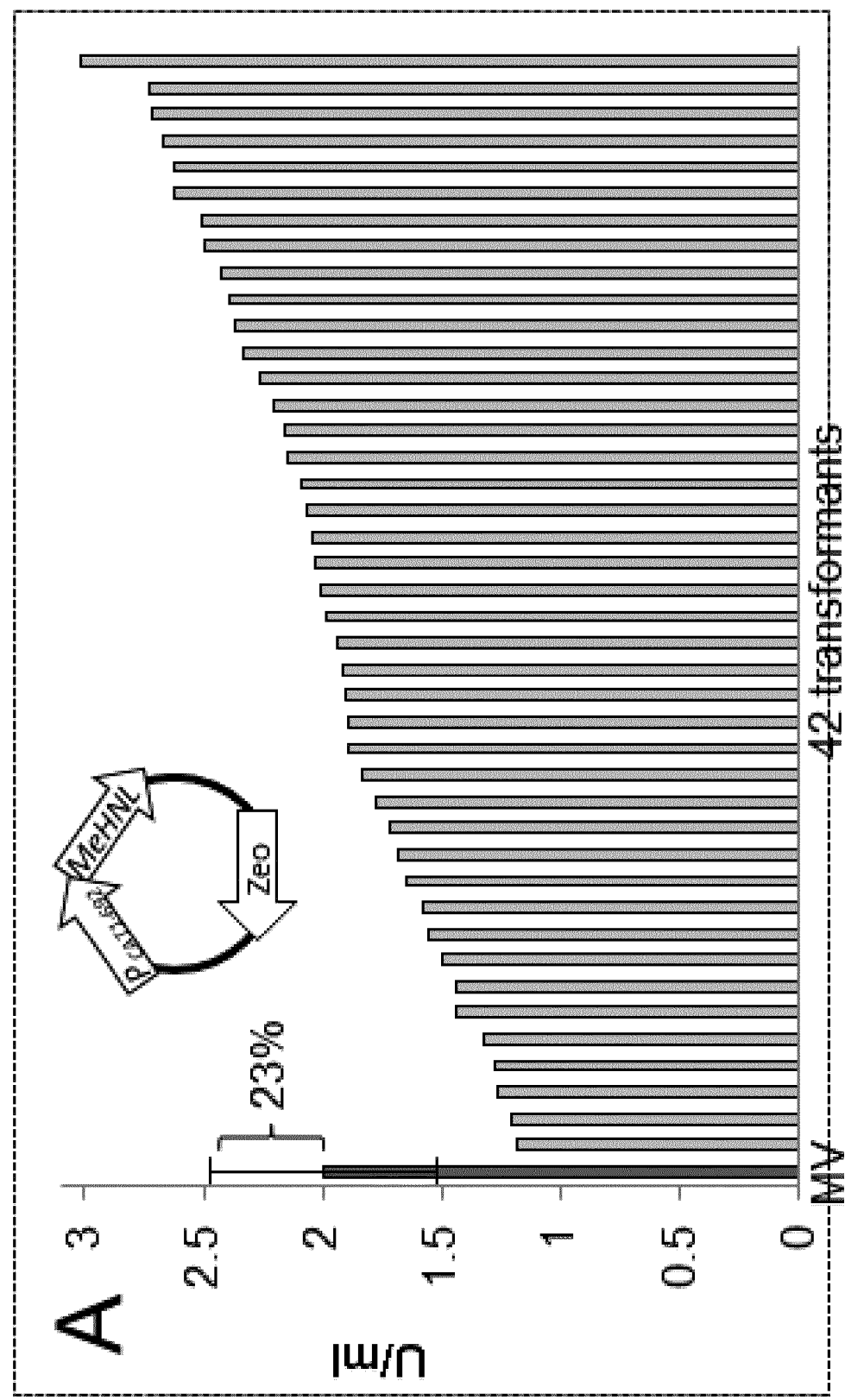
Figure 7B:
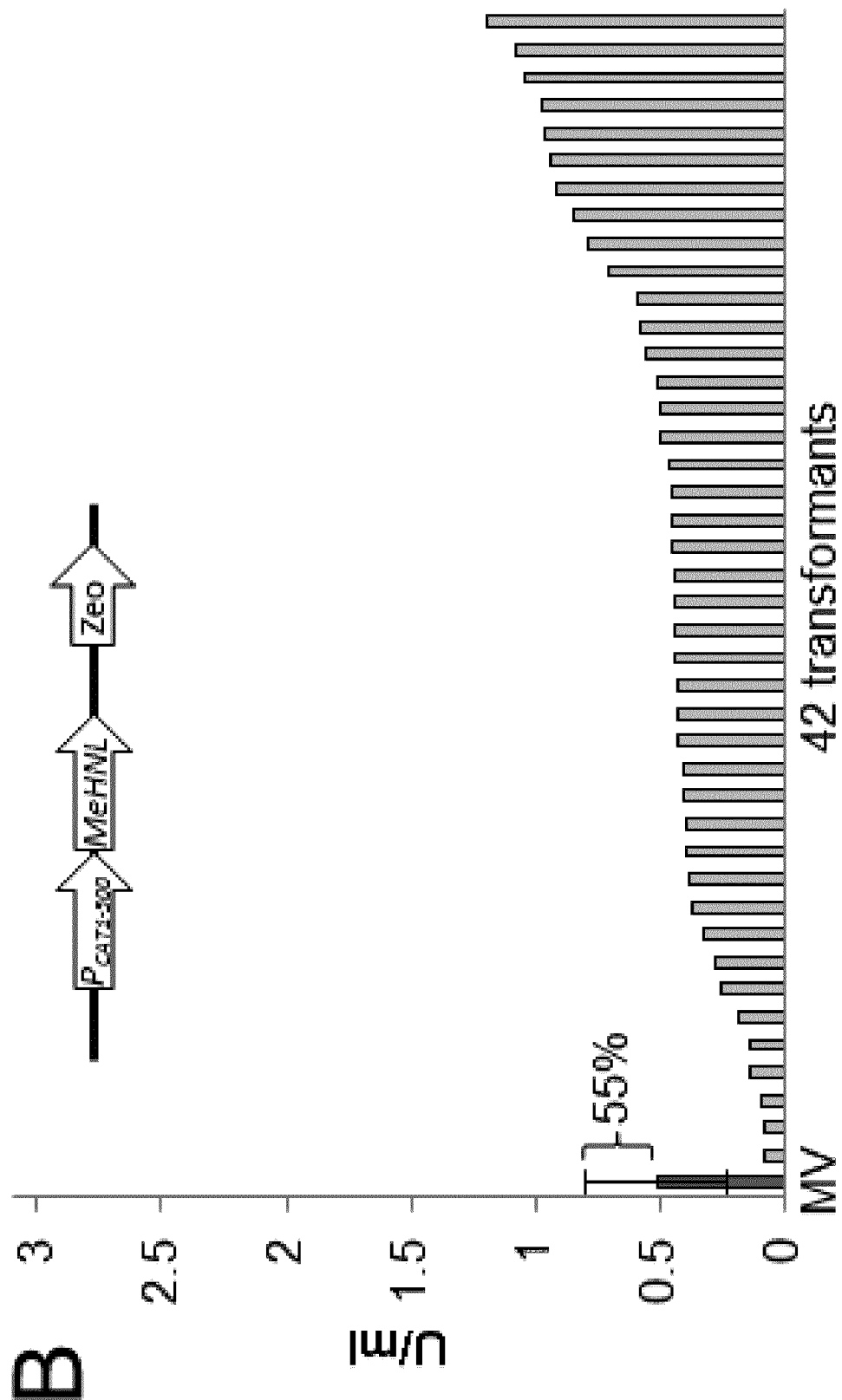

FIG. 7: MeHNL expression from a circular plasmid bearing $P_{CAT1-692}$ and from a linearized plasmid bearing $P_{CAT1-500}$ tested with Zeocin selection shows similar results as obtained with of GUT1 selection (see FIG. 4). Mean value of activity with ARS is about 3.9 times higher than genomic integration. Same experiment as FIG. 4, except the plasmids contained a Zeocin resistance gene and the cultivation was performed in YPD-Zeo full media.

FIG. 8: Reducing the DNA amount of linearized $P_{CAT1-500}$ plasmids to approximately 1000 ng improved landscape uniformity for MeHNL (A) and LuHNL (B) activity (compared to FIG. 4B,D). Same experiment as in FIG. 4 except only amounts equivalent to 1000 ng of the pPpT4S vector (Näätsaari et al. 2012) were transformed. Landscape uniformities are changed for MeHNL from 88% standard deviation (FIG. 4B) to 57% (A) and for LuHNL from 69% (FIG. 4D) to 76% (B). Further reducing the DNA amounts transformed may lead to uniformity improvements at the cost of reduced numbers of transformants.

FIG. 9: Sequence of $P_{CAT1-692}$ (SEQ ID NO:1)

FIG. 10: Sequence of putARS-$P_{CAT}$ (SEQ ID NO:2)

FIG. 11: Sequence of $P_{CAT500-692}$ (SEQ ID NO:3)

FIG. 12: Sequence of CAT1-500 promoter without ARS sequence (SEQ ID NO:4)

FIG. 13: Sequence of CbAOD1 Promoter ARS (SEQ ID NO:5)

FIG. 14: Sequence of AOD-F1 (SEQ ID NO:6)

FIG. 15: Sequence of AOD-F2 (SEQ ID NO:7)

FIG. 16: Sequence of AOD-F3 (SEQ ID NO:8)

FIG. 17: Sequence of AOD-F4 (SEQ ID NO:9)

FIG. 18: Sequence of AOD-F5 (SEQ ID NO:10)

FIG. 19: Sequence of AOD-F6 (SEQ ID NO:11)

FIG. 20: Sequence of pCAT1noCore (SEQ ID NO:12)

FIG. 21: Sequence of SapI cloning stuffer (SEQ ID NO:13)

Figure 22:
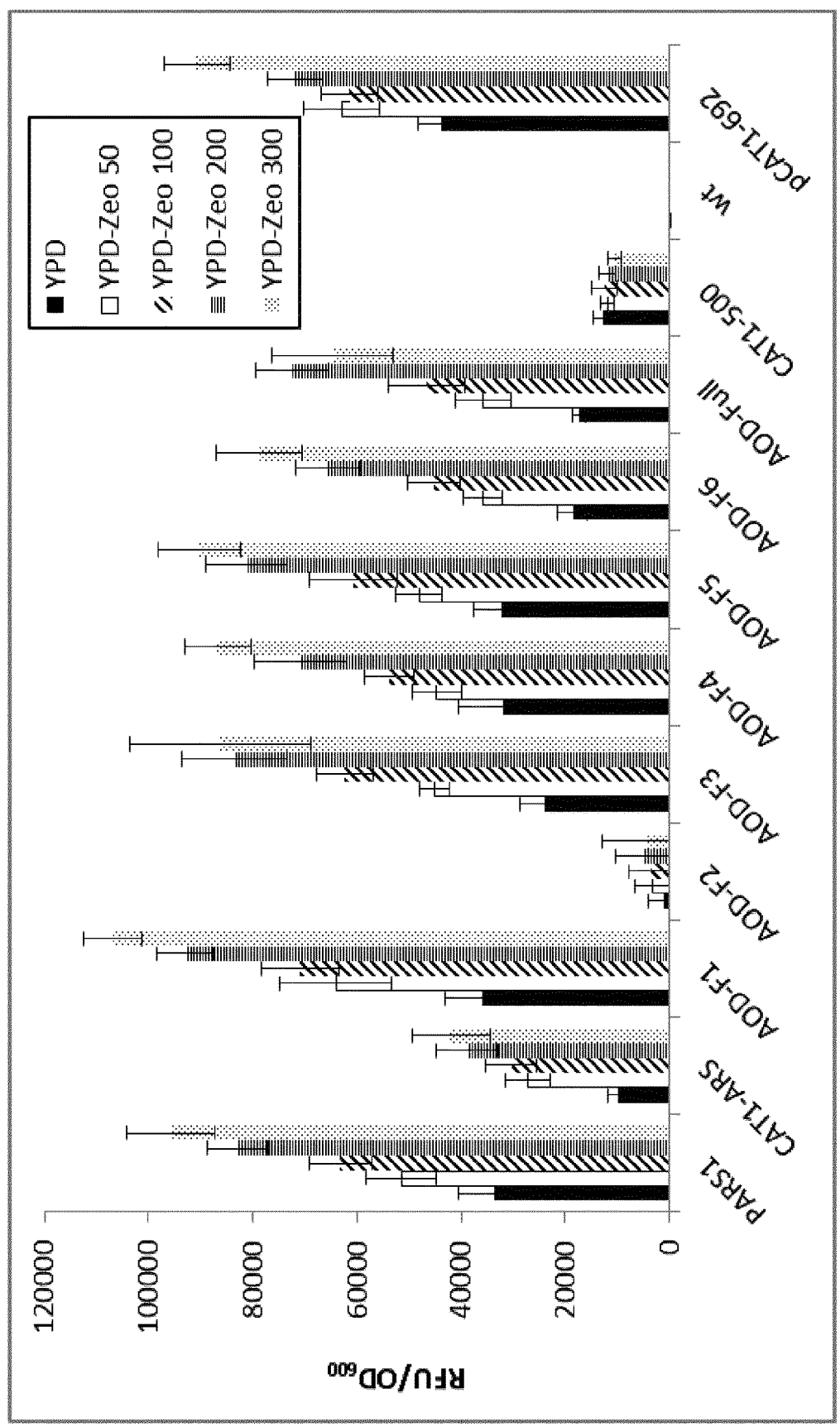

FIG. 22 shows the eGFP expression values after 60 h of cultivation. AOD-Full stands for C. boidinii $P_{AOD1}$ (SEQ ID NO:5) including an ARS/terminator element and the F for the different fragments thereof (SEQ ID 6-11). CAT1-500=SEQ ID 4, pCAT1-692=SEQ ID1, CAT1-ARS=SEQ ID 3.

Figure 23:
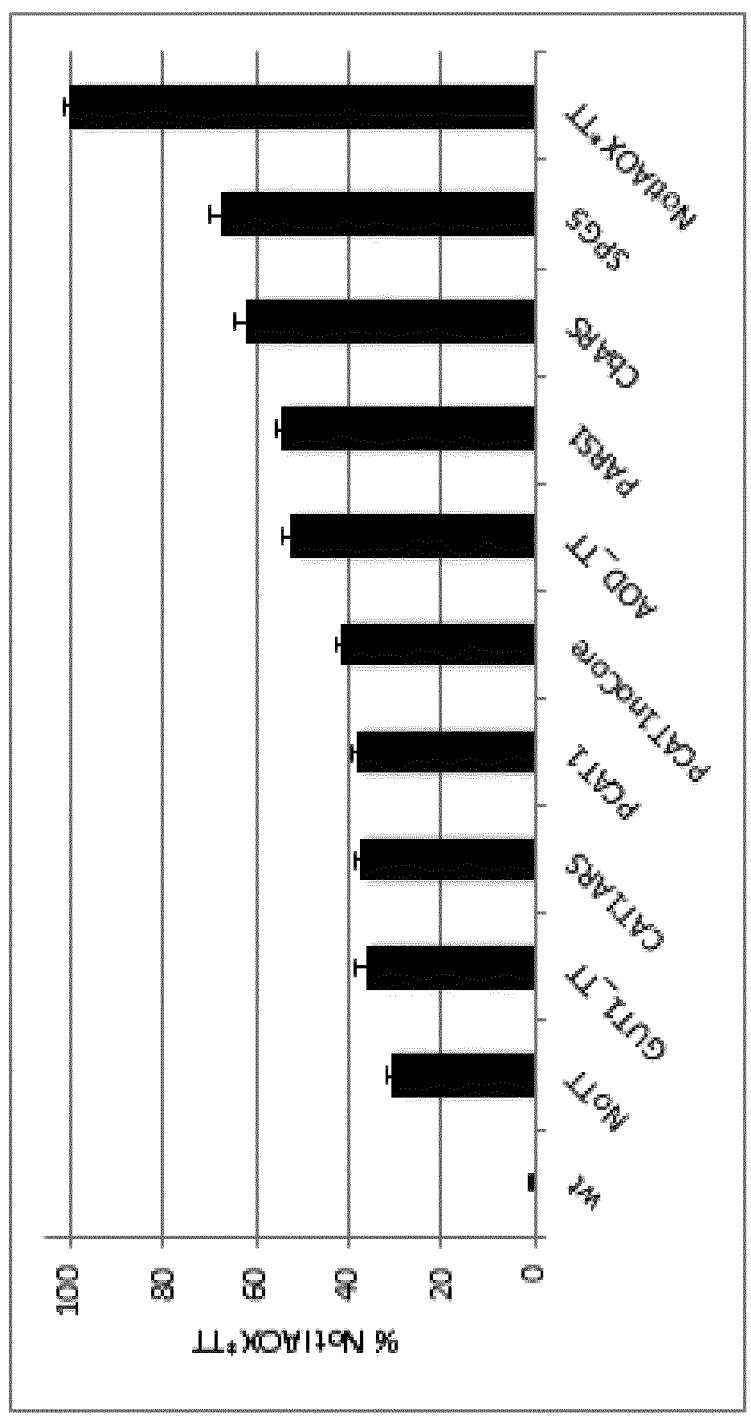

FIG. 23 shows the transcription terminator efficiency of ARS fragments compared to the best known P. pastoris terminator sequences (TT). eGFP expression values after 60+48 h of cultivation. 60 h cultivation in BMD and 48 h induction with MeOH in 96 well plate experiment. The terminator of the P. pastoris AOD1 gene AOD_TT (present in JQ519690 bp 2360-2835) is a standard element of selection marker cassettes in typical Pichia integration vectors (Näätsaari et al 2012) and used as a benchmark in these experiments. The 2 new ARS sequences both are functional as transcription terminators. Surprisingly the heterologous ARS sequence from C. boidinii showed an even stronger effect as the previously known ARS 1 sequence and also than the frequently used terminator of the P. pastoris AOD1 gene.

Figure 24:
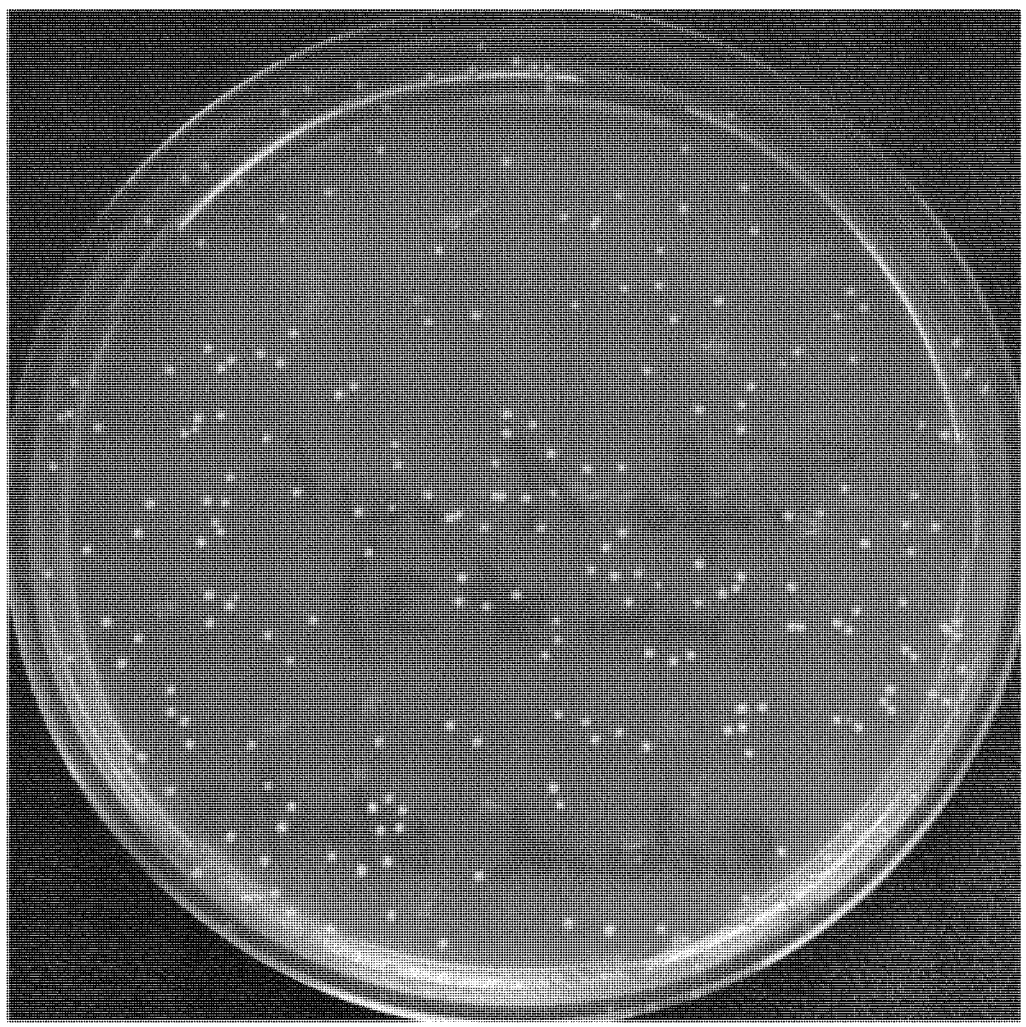

FIG. 24 shows transformants from direct transformation with plasmid DNA isolated from P. pastoris without prior amplification and isolation from E. coli.

Figure 25:
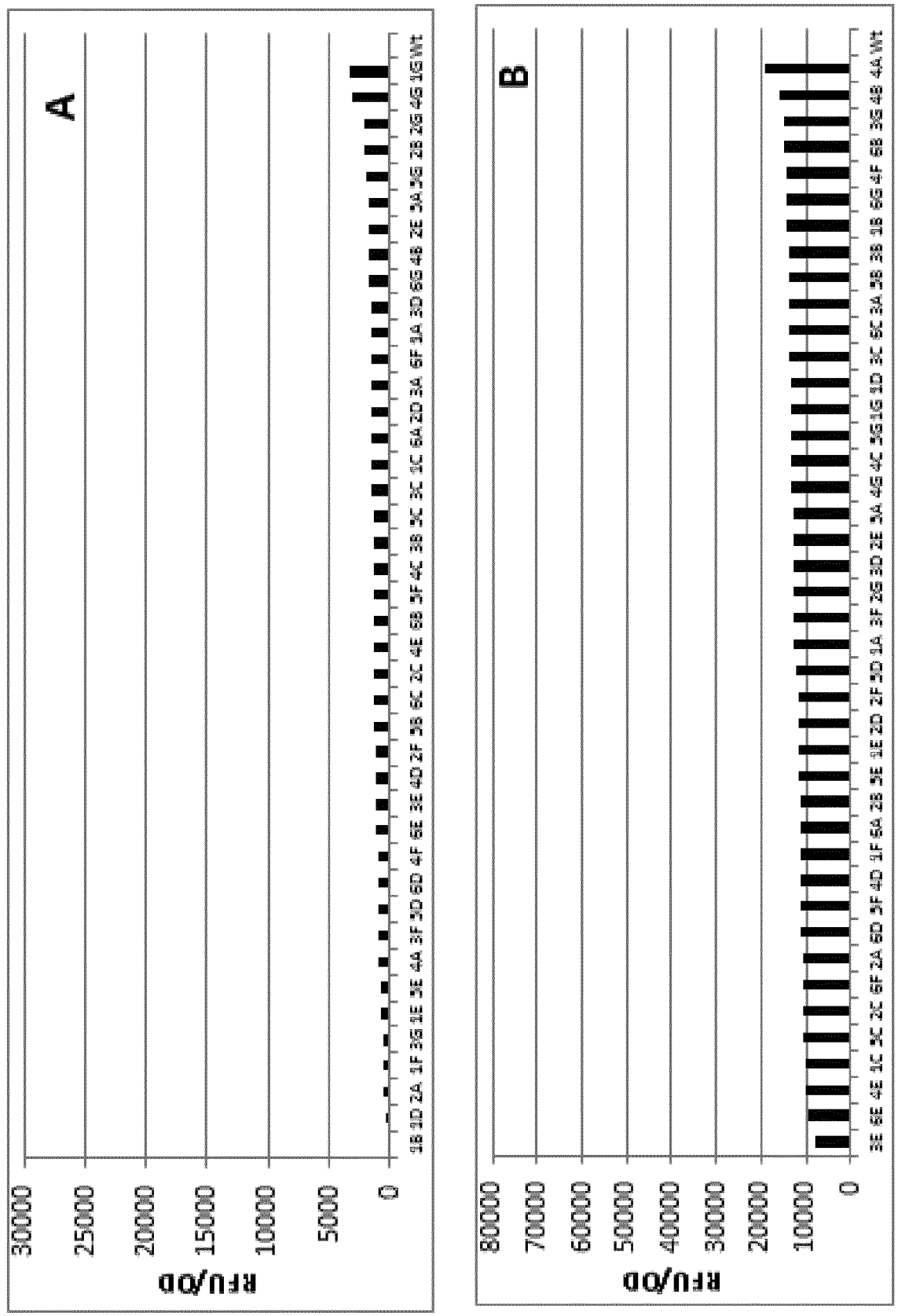
Figure 25:
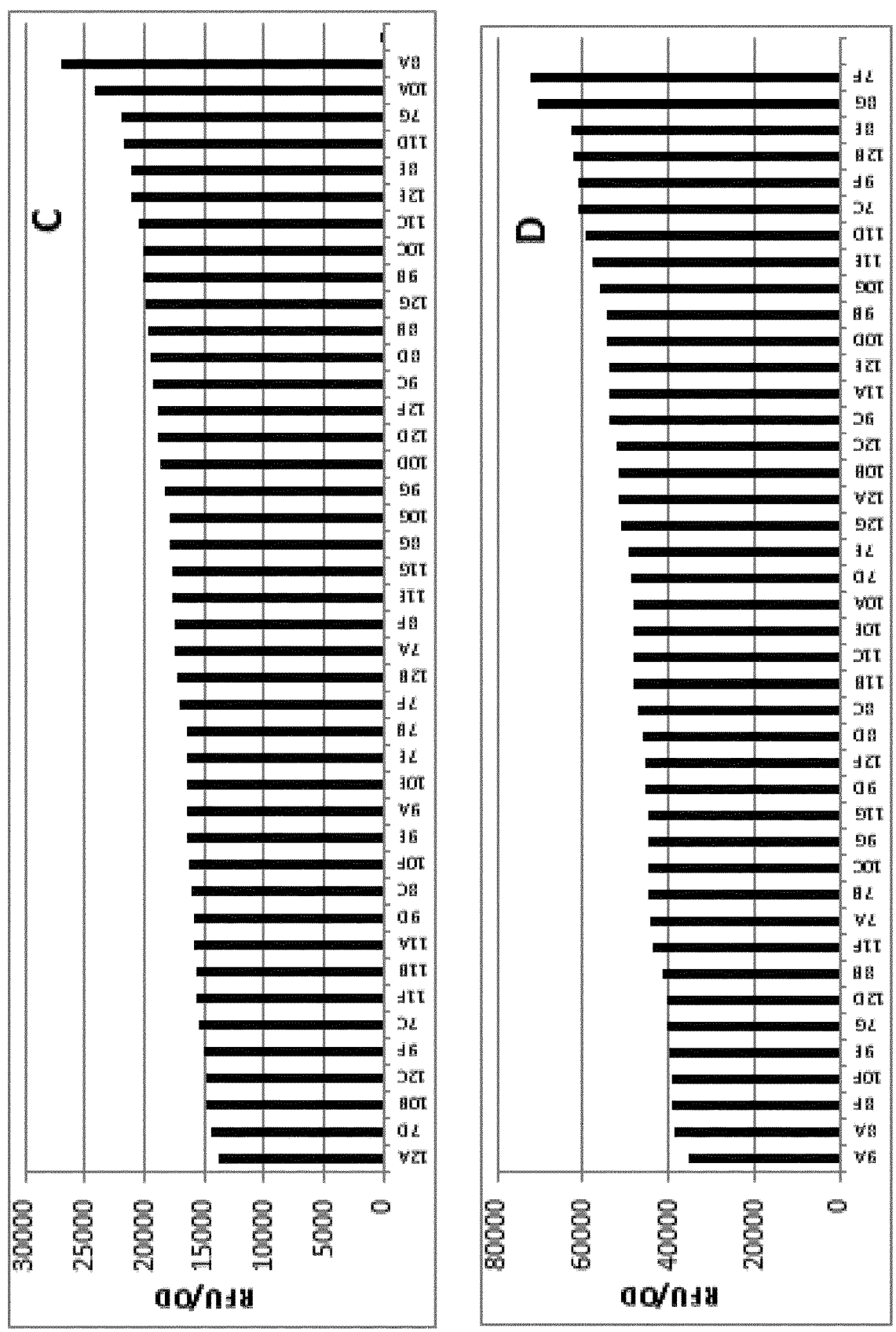

FIG. 25 shows eGFP expression of individual transformants under the control of PCAT1 promoter, using episomal plasmids with different sequence parts (A,B with PARS1, C&D with CbARS (the ARS consisting of the polynucleotide SEQ ID NO:6 was used) used as bifunctional ARS and terminator sequences for the selection marker (with and without selective pressure) and autonomous plasmid replication. FIG. 25A, PARS1 YPD; FIG. 25B, PARS1 YPD-Zeo; FIG. 25C, CbARS YPD; FIG. 25D, CbARS-Zeo; eGFP expression values were measured after 60 h cultivation time. In contrast to the new heterologous ARS, the *P. pastoris* PARS1 was not stable when used as bifunctional ARS and TT DNA part (very low expression without selective pressure and also lower expression levels with Zeocin compared to the CbARS).

Figure 26:
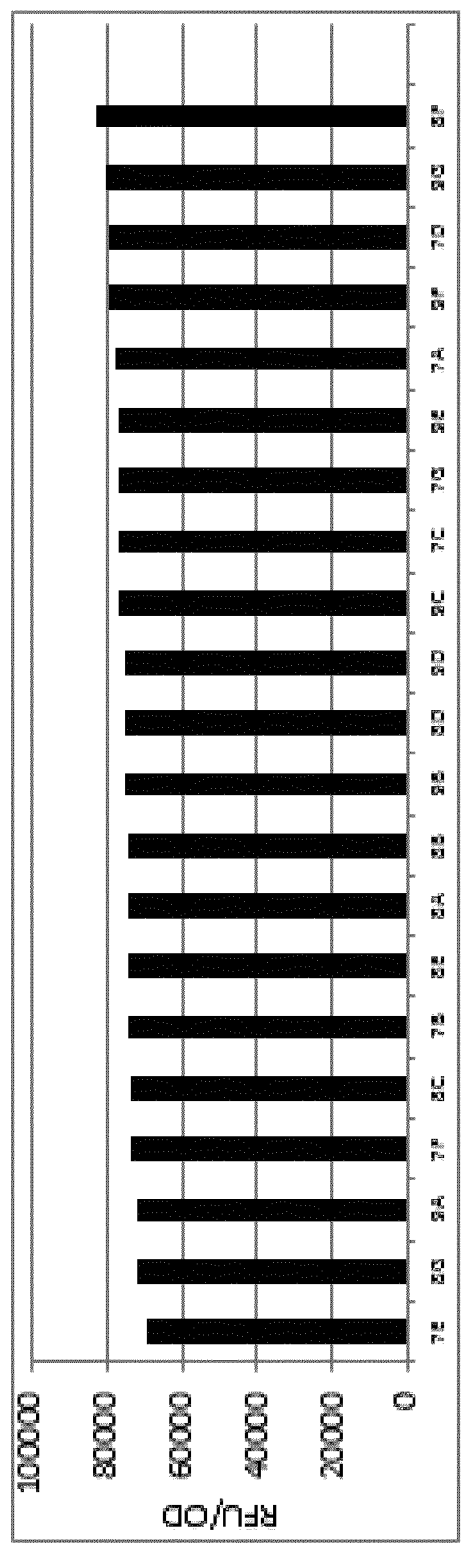

FIG. 26 shows the GAP promoter driven eGFP expression of 21 individual transformants.

Figure 27:
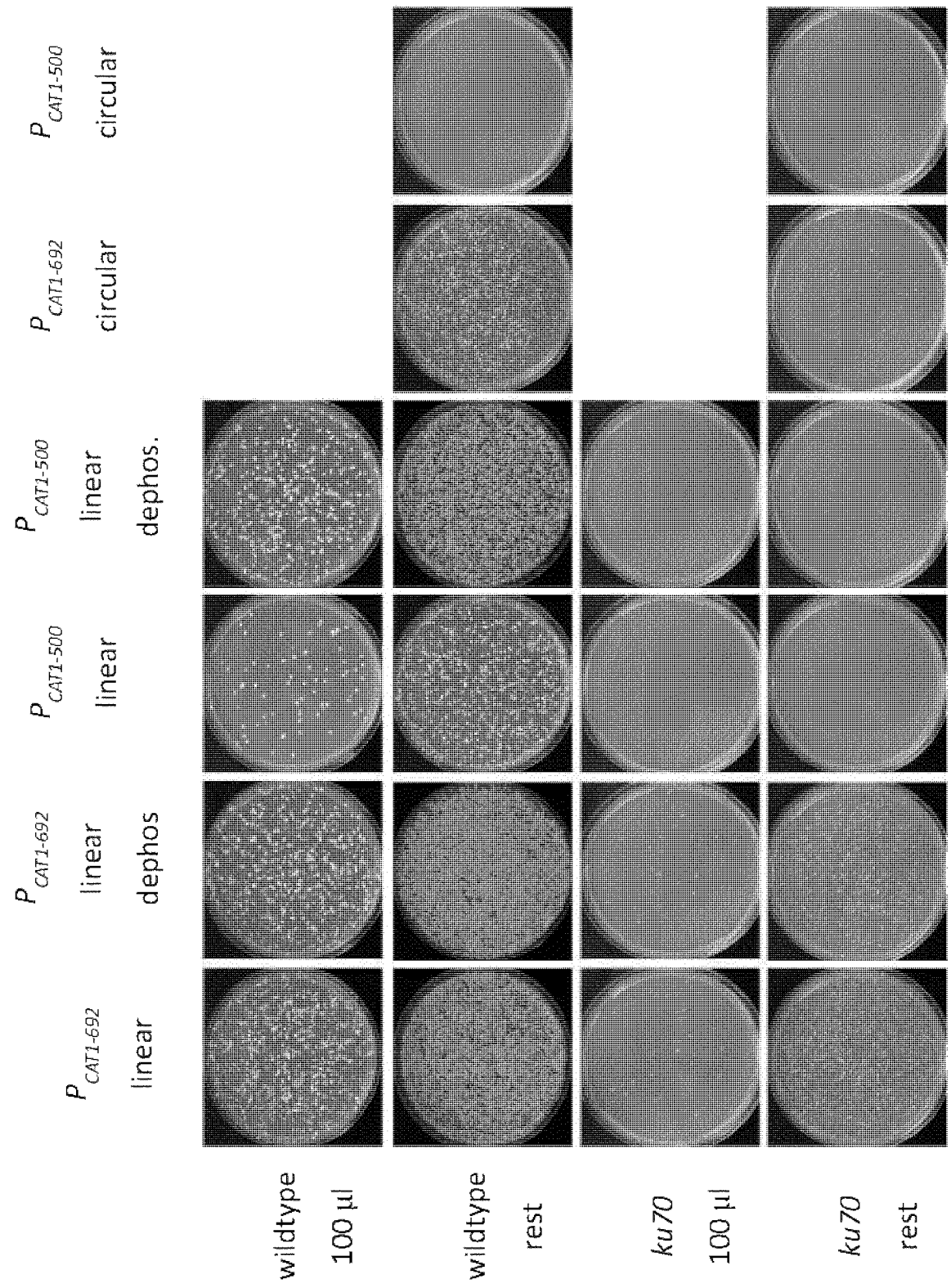

FIG. 27 shows the transformation efficiency of *K. phaffii* strain BSYBG11 (indicated as wild type) and the KU70 deletion variant BSY11dKU70 with linearized (with and without dephosphorylation) and circular plasmids containing the CAT1-500 promoter (without ARS element) and the CAT1_692 element (with ARS sequence). The KU70 deletion strain showed significantly lower numbers of transformants and smaller colonies due to slower growth compared to the wt strain.

Figure 28:
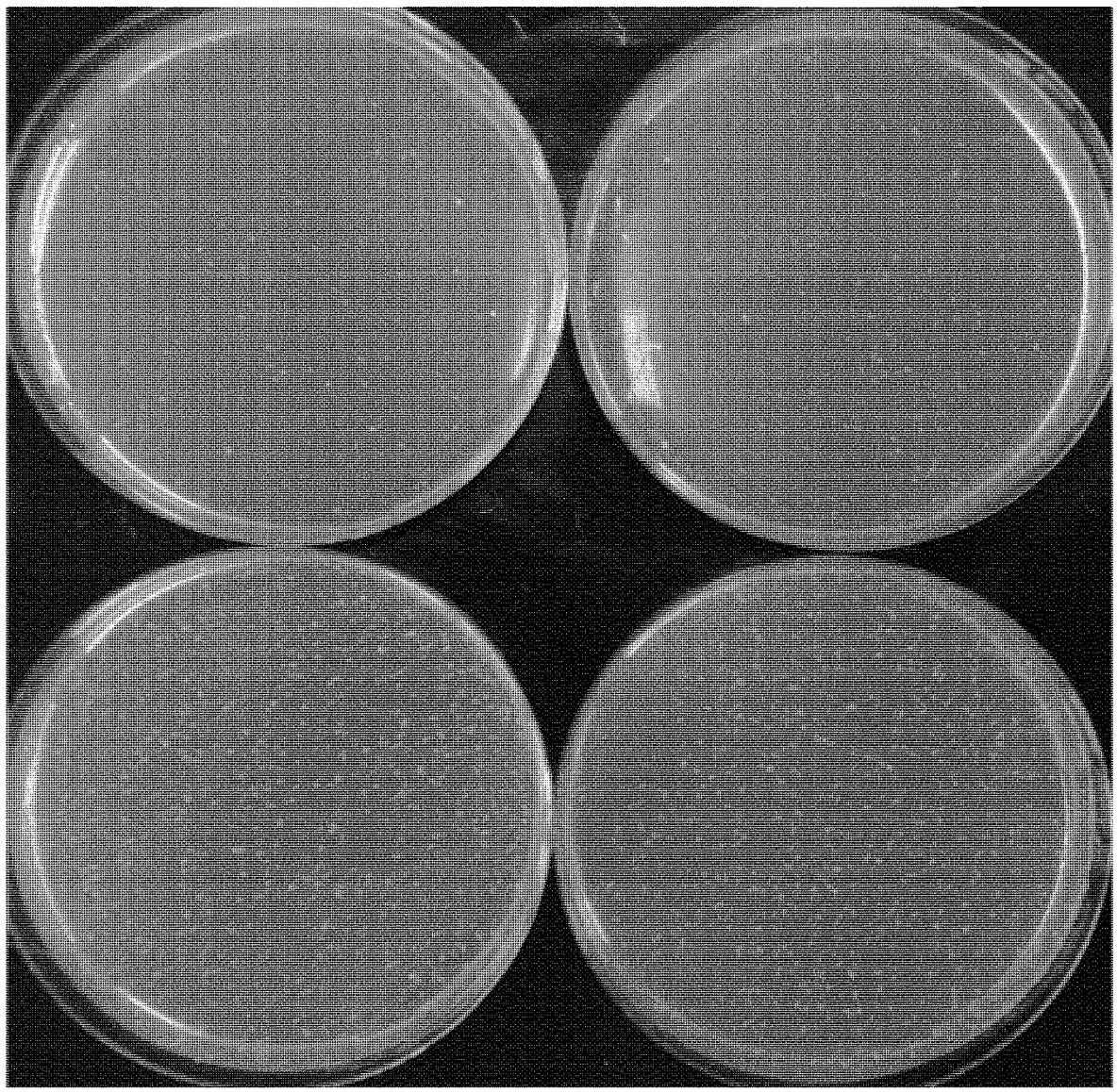

FIG. 28: HR cloning with different lengths of overlapping regions. Fifty ng of vector backbone and a 3:1 molar ratio insert:vector were used for transformation and 100 µl of the regenerated transformants were plated onto selective media. A: 50 bp, B: 100 bp, C: 250 bp, D: 500 bp.

Figure 29:
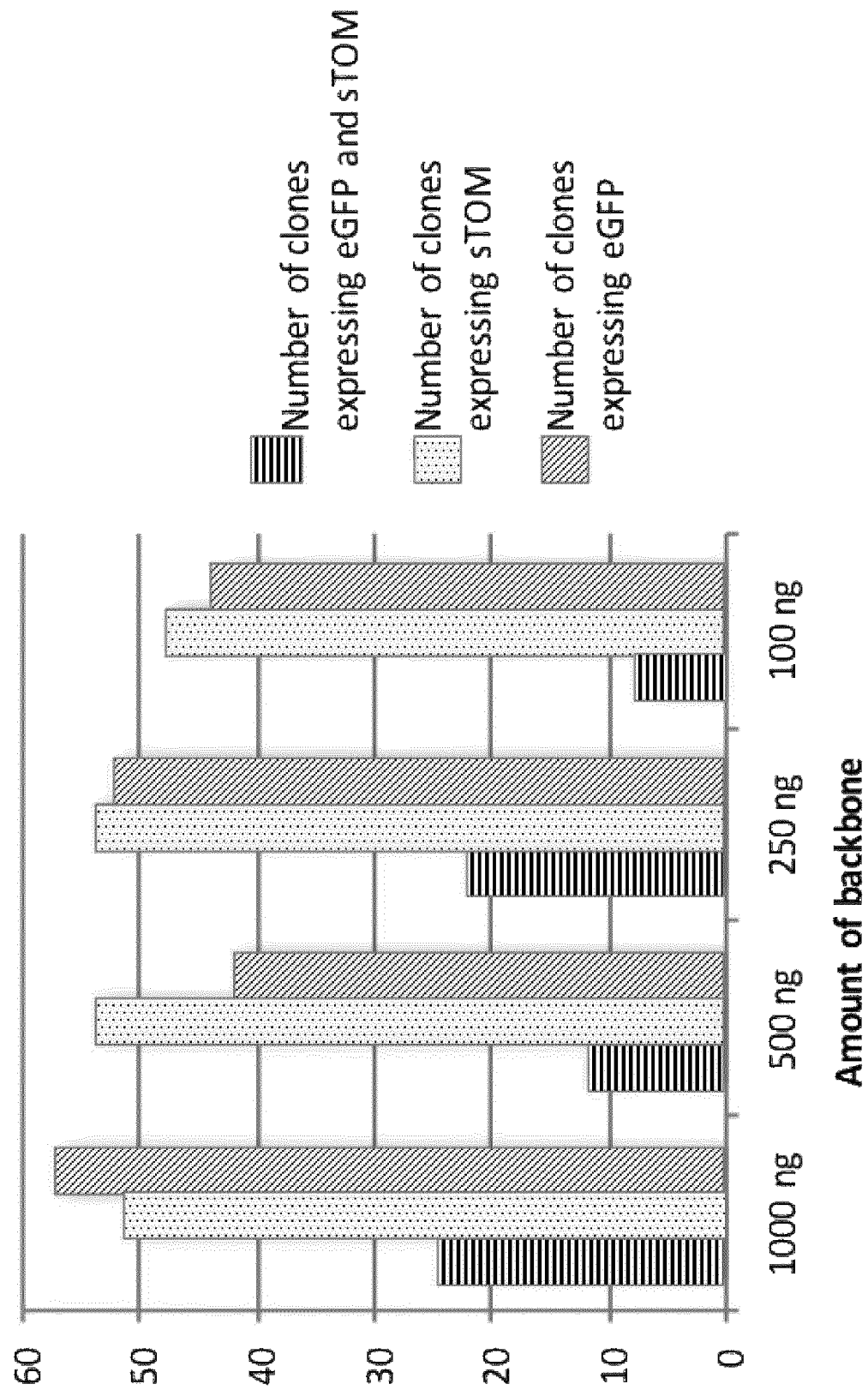

FIG. 29: Uptake of multiple inserts per cell. Different amounts of vector backbone and twice as much insert (1:1 mix of eGFP and sTomato with 250 bp overlapping regions) were used for transformation and tested for the uptake of multiple variants.

Figure 30:
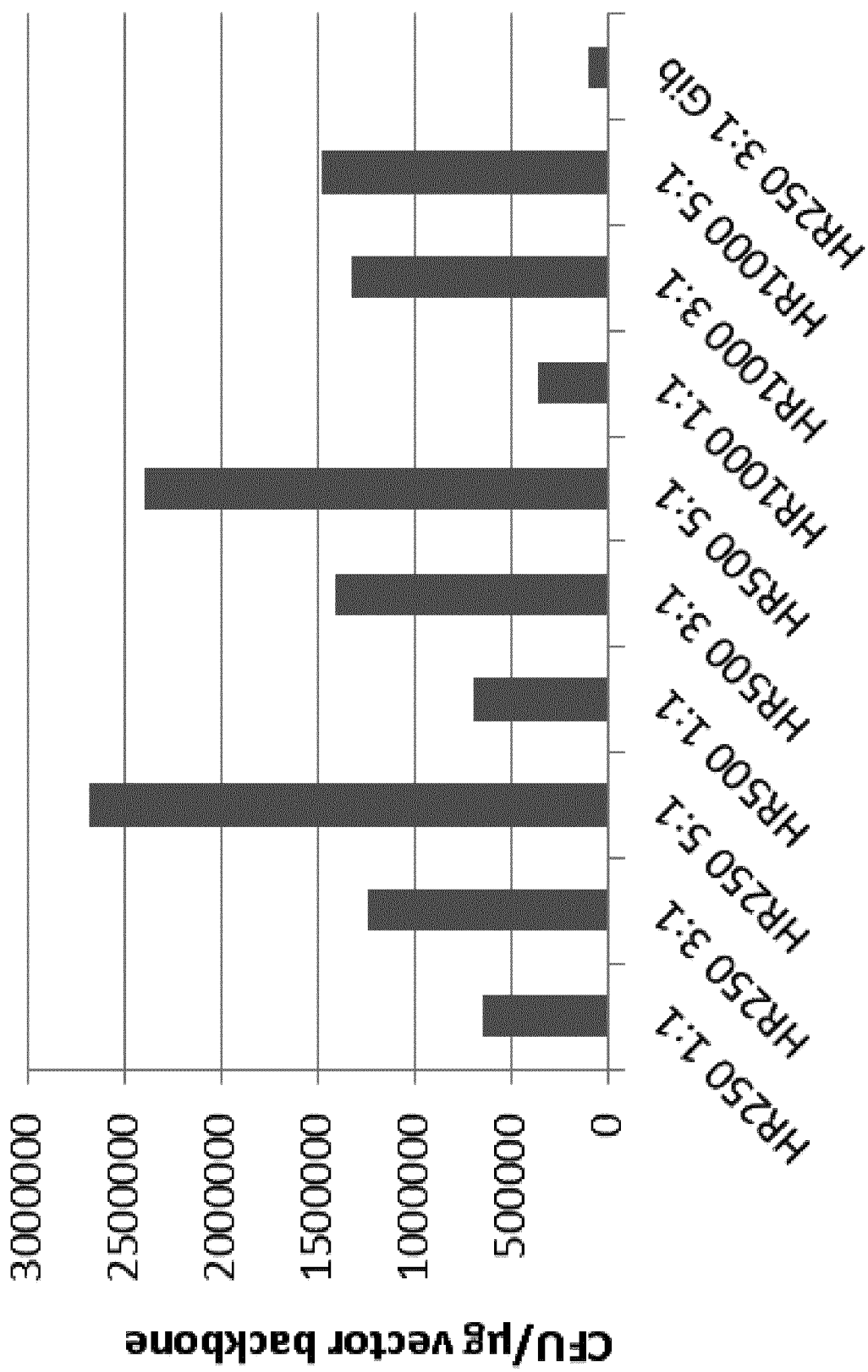

FIG. 30: HR cloning transformation efficiency tests with Herceptin CDSs including signal sequences and promoters (construct 1c) as insert. Different lengths of homologous regions (HR250=250 bp) and molar ratios (5:1=ratio insert:vector backbone) were used with 50 ng of vector backbone. The numbers after HR indicate the overlap length.

Figure 31:
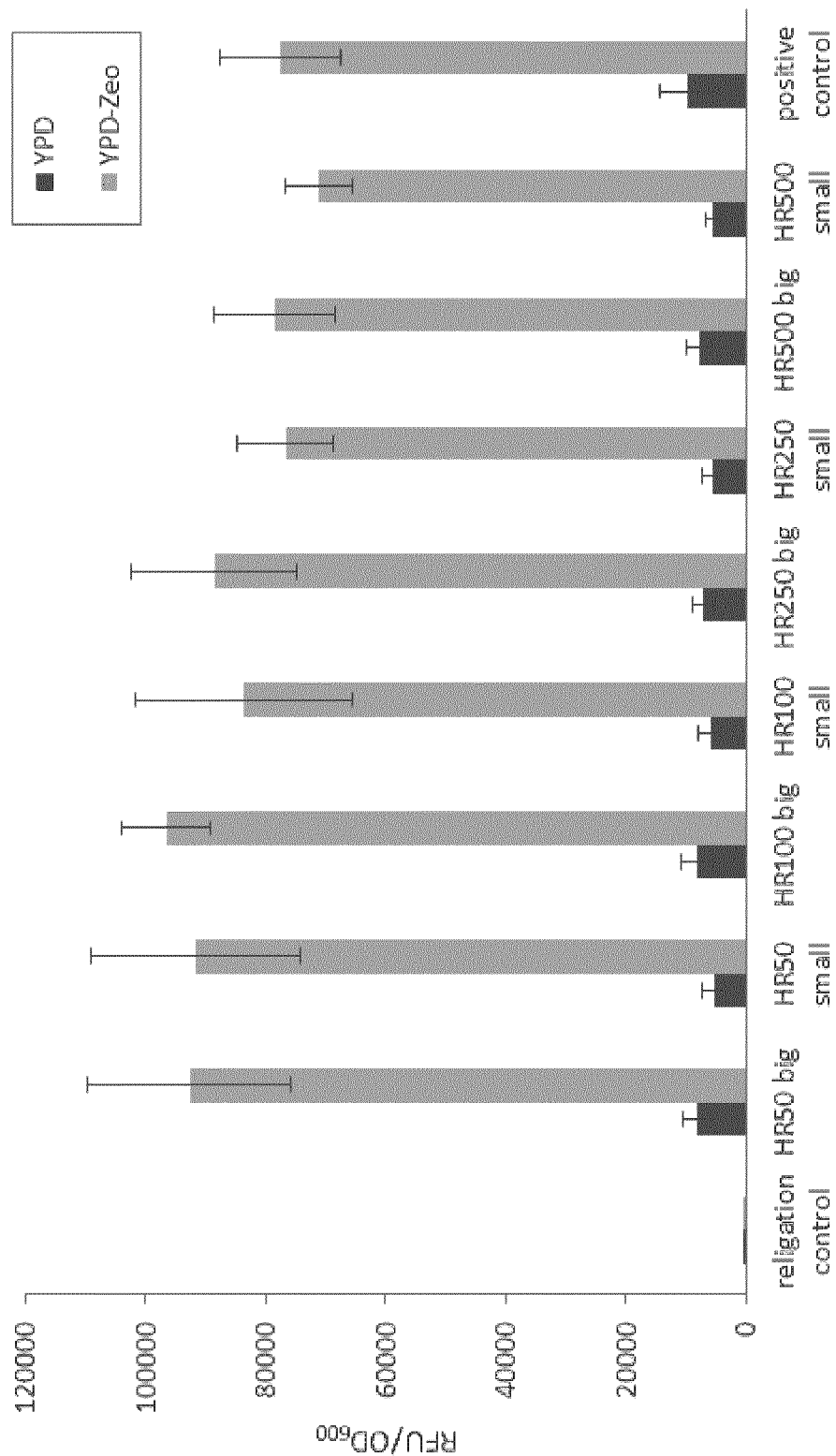

FIG. 31: Cultivation of transformants generated by HR cloning in non-selective and selective media. The number after HR indicates the length of the homologous regions to the vector backbone. Small and big colonies were chosen for cultivation. A fully assembled circular CbARS based expression vector served as positive control. Twenty-one transformants per size and overlap length were tested, 168 in total.

Figure 32:
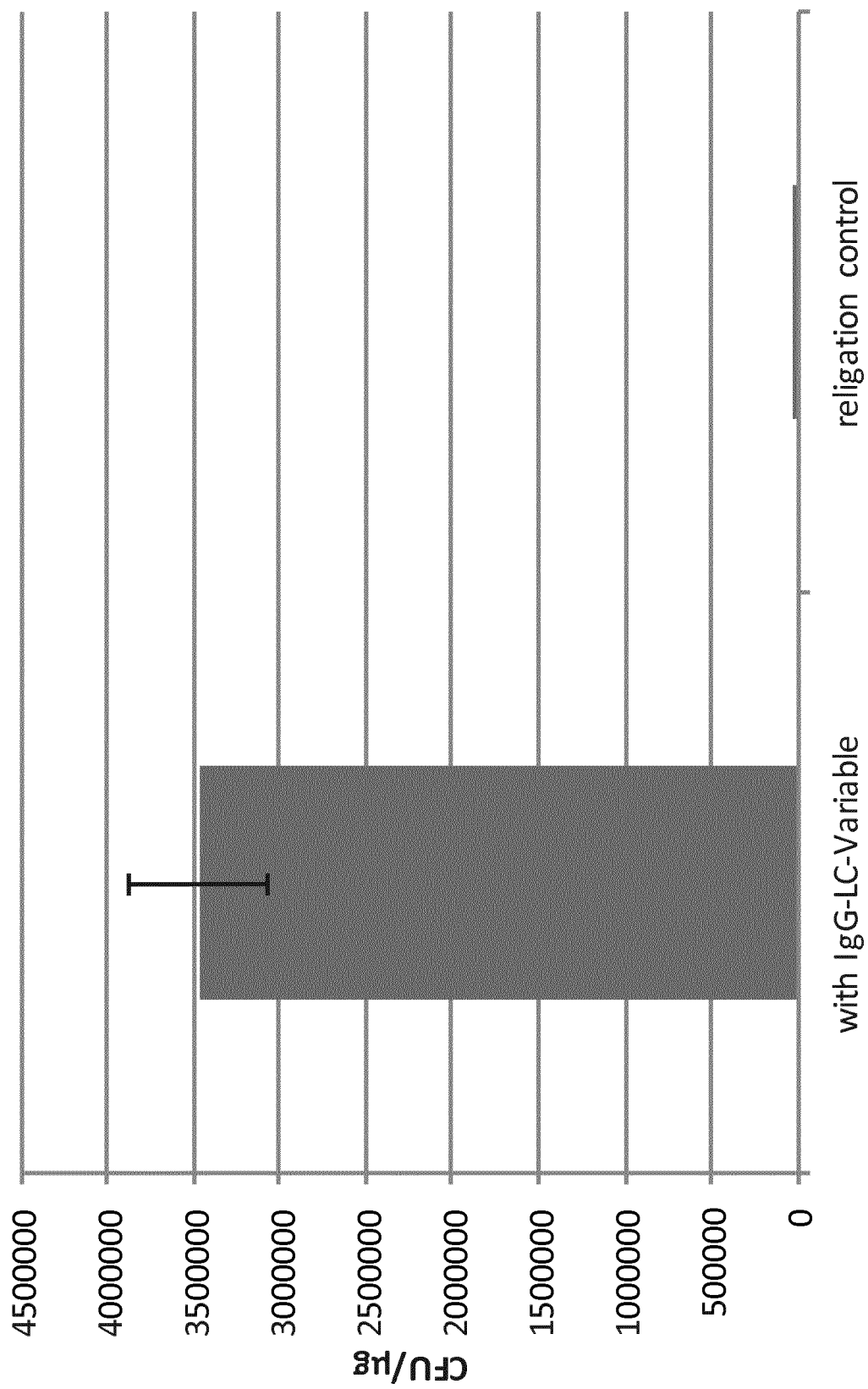

FIG. 32: HR cloning using the variable region of an IgG light chain as insert. One µg vector backbone and 2 µg insert were used for the transformation of *P. pastoris* BSY11dKU70. The regenerated transformants from three individual transformations were plated onto selective media after proper dilution and the CFUs counted and normalized to 1 µg of vector backbone.

FIG. 33:
SEQ ID NO:72: vector sequence used in the examples
SEQ ID NO:85: vector sequence used in the examples
SEQ ID NO:86: vector sequence used in the examples
SEQ ID NO:87: ku70 gene of *P. pastoris*, >gi|328352576: 1598101-1599963 *Pichia pastoris* CBS 7435 chromosome 3, complete replicon sequence;

DETAILED DESCRIPTION OF THE INVENTION

The present invention specifically relates to an episomal plasmid vector comprising a gene of interest and an autonomously replicating sequence (ARS), and optionally further comprising a promoter and a selection marker, wherein the gene of interest is under transcriptional control of said promoter and wherein said ARS comprises the nucleotide sequence of SEQ ID NO:2, SEQ ID NO:3, SEQ ID NO:5, or SEQ ID NO:6-11, or a functionally active variant of any of the foregoing.

Furthermore, described herein are methods of producing episomal plasmid vectors using homologous recombination in *P. pastoris*.

Specific terms as used throughout the specification have the following meaning.

The term "gene of interest" (GOI) as used herein shall refer to any non-coding and coding gene or partial coding gene, e.g., encoding a protein of interest (POI) or fragment thereof, which is desired to be expressed in a host cell, or a non-coding RNA, optionally at high levels. Genes of interest include but are not limited to genes encoding enzymes (e.g. process enzymes), biocatalysts, antibodies and fragments thereof, antigen binding peptides, immunogenic proteins, regulatory proteins, cell signaling and ligand binding proteins, cytokines, hormones, protein antibiotics, peptide hormones, inhibitor peptides, peptide containing biosurfactants, structural proteins, serum albumin, gelatin or collagen, human growth factors, tissue plasminogen activator, toxins/toxin, fusion proteins, or any other proteins or peptides having potential commercial use, e.g. being of proteins or polypeptides of therapeutic, diagnostic or pharmaceutical importance including enzymes catalyzing partial or whole metabolic pathways. Particular examples of a GOI are encoding antibodies, immunoglobulins, or antigen-binding regions or fragments thereof, in particular scFv, or Fabs, enzymes such as hydrolases, oxidoreductases, isomerases, lyases or ligases. A GOI typically comprises or consists at least any of 20, 30, 40, or 50 consecutive nucleotides of a non-coding nucleotide sequence or a gene encoding a POI.

In particular, the term "gene" shall also include DNA fragments of a gene, in particular those that are partial genes. A fragment can also contain several open reading frames, either repeats of the same ORF or different ORFs. The term shall specifically include nucleotide sequences, which are non-coding, e.g. untranscribed or untranslated sequences, or encoding polypeptides, in whole or in part. Exemplary non-coding "genes" are regulatory genes or promoter sequences. Therefore, specific examples of GOI variants relate to promoter variants and gene variants encoding polypeptides or proteins, such as antibodies, antibody-fragments or peptidic/polypeptidic antigen-binding molecules.

Specific examples of a POI are antigen-binding molecules, such as an antibody, or a fragment thereof. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH or VHH or V-NAR. Further antigen-binding molecules are selected from (alternative) scaffold proteins such as e.g. engineered Kunitz domains, Adnectins, Affibodies, Anticalins, and DARPins. The term "scaffold" describes a multifaceted group of compact and stably folded proteins—differing in size, structure, and origin—that serve as a starting point for the generation of antigen-binding molecules. Inspired by the structure-function relationships of antibodies (immunoglobulins), such an alternative protein scaffold provides a robust, conserved structural framework that supports an interaction site which can be reshaped for the tight and specific recognition of a given (bio)molecular target.

The proteins of interest expressed with the plasmids and methods described herein may be non-secreted or secreted (including proteins integrated or attached to the cell wall or on the cell surface. The non-coding RNA transcribed from the ARS plasmid for example may have regulatory properties. Non-coding RNAs of special interest are snRNAs, antisense RNAs, long non-coding RNAs, siRNAs, ribozymes.

The protein examples described herein are non-limiting and any protein or peptide or polypeptide capable of being expressed in a eukaryotic cell, i.e., in yeast, can be expressed employing the episomal plasmid vectors, host cells, and methods described herein. The proteins of interest described above can be from any species (e.g., mammalian or human proteins). Specifically, the term "POI" as used herein refers to a recombinant polypeptide or a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. In some cases the term POI as used herein also refers to any metabolite product by the host cell as mediated by the recombinantly expressed protein.

As used herein, the terms "polypeptide" and "protein" are used interchangeably to refer to polymers of any length comprising amino acid residues linked by peptide bonds. The conventional one-letter or three-letter codes for amino acid residues are used herein. Polypeptides may include disulfide bonds, glycosylation, lipidation, acetylation, phosphorylation, amidation or any other modifications. By "functional protein" or "functional polypeptide" is intended that the protein or polypeptide operates for its intended purpose. For example, a functional enzyme will catalyze a specific reaction.

The term "recombinant" as used herein shall mean "being prepared by or the result of genetic engineering". Thus, a recombinant microorganism or host cell comprises at least one "recombinant nucleic acid". A recombinant microorganism specifically comprises an expression vector or cloning vector, or it has been genetically engineered to contain a recombinant nucleic acid sequence. A "recombinant protein" is produced by expressing a respective recombinant nucleic acid in a host. A "recombinant promoter" is a genetically engineered non-coding nucleotide sequence suitable for its use as a functionally active promoter as described herein.

The term "isolated" as used herein with respect to a nucleic acid such as a promoter of the invention shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized. This term specifically refers to a DNA molecule that is separated from sequences with which it is immediately contiguous in the naturally occurring genome of the organism in which it originated. For example, an "isolated promoter" may comprise a DNA molecule inserted into a vector, such as a plasmid, or integrated into the genomic DNA of a host organism. An isolated promoter may further represent a molecule produced directly by biological or synthetic means and separated from other components present during its production.

It is well understood that the episomal plasmid or library of episomal plasmids described herein can be provided in the isolated form, which is conveniently used as a tool to further engineer recombinant hosts incorporating such episomal plasmids.

A "plasmid" as used herein is defined as a vector which is a nucleic acid construct used to transform a host cell for expression of a protein, polypeptide, or peptide, and the vector is not found in nature in the host cell it transforms. A plasmid or vector, also referred to as "plasmid vector" is specifically understood as an extrachromosomal nucleic acid which is particularly physically separated from a chromosomal DNA. A plasmid may or may not include DNA sequences that are required for the transcription of cloned recombinant nucleotide sequences, i.e., of recombinant genes and the translation of their mRNA in a suitable host organism. Plasmid vectors usually comprise an origin for autonomous replication in the host cells, selectable markers, a number of restriction enzyme cleavage sites, a suitable promoter sequence and a transcription terminator, which components are operably linked together. Plasmids may as well serve as a carrier of a GOI and variants of a GOI produced by mutagenesis, such that a library of plasmids is produced comprising a repertoire of GOI variants. According to a certain embodiment, the plasmid described herein is a *Pichia* plasmid, in particular a *P. pastoris* plasmid which is capable of replicating and expressing a GOI in a *P. pastoris* cell culture.

Though the plasmid described herein may contain naturally-occurring nucleotide sequences, the plasmid comprising a heterologous sequence, such as a promoter or GOI which is heterologous (foreign) to the plasmid. Therefore, the plasmid described herein though obtainable by a biosynthesis method, is considered a synthetic product, i.e., an artificially created nucleotide sequence that is not produced naturally but is a man-made design.

A plasmid or vector which is "episomal" is herein understood as an episomally or autonomously replicating plasmid which is replicating independently of the host cell chromosome and advantageously maintained as extrachromosomal vector in a culture of the host cell, such that it is not significantly integrated into the host cell chromosome when cultivated over several generations. A recombinant host cell comprising an episomal plasmid vector is advantageously (genomically) stable, in which the episomal plasmid persists for many generations. If unstable, the episomal plasmid would be gradually diluted out of the population by successive cell divisions. A stable episomally replicating plasmid may be maintained in a cell population by selective pressure (e.g., in the presence of an antibiotic). The use of episomal plasmid described herein results in a higher transfection efficiency than the use of chromosome-integrating plasmids. Furthermore, the episomal plasmid can be introduced into a series of eukaryotic host cells and replicate as extrachromosomal construct.

An episomal plasmid may be stably maintained in a host cell. The stability can be determined by methods described herein and known in the art, e.g. by sequencing the host cell genome. In particular, the genomic stability of a host cell comprising the episomal plasmid can be determined upon cultivating the host cell in a host cell culture, and stability is e.g. determined after a period of time reflecting about 10, 15 or 20 generations of cultivation.

The term "vector backbone" as used herein refers to a nucleic acid construct used for the transformation of cells in gene manipulation procedures. Vector backbones typically comprise selectable markers, restriction enzyme cleavage sites, and may comprise polynucleotide sequences necessary to express protein molecules, which confer specific properties on the host cell to be transformed, and/or respective control sequences for protein expression, e.g. regulatory sequences such as promoter sequences and transcription terminator sequences. Artificial vectors may be constructed by various molecular biology techniques such as cutting DNA molecules from different sources using restriction enzymes, assembly of individual DNA molecules using polynucleotide polymerase reactions or artificial DNA synthesis and joining such DNA molecules using ligases. A vector backbone may contain all elements of an expression vector, yet, without a GOI.

The term "insert" as used herein refers to a vector insert which is a linear nucleic acid molecule suitable for integrating into a vector backbone, e.g. through homologous recombination.

A vector insert described herein specifically comprises a GOI, in particular fragments of a gene or selected regions of mutagenesis to produce variants of a GOI. In addition, the insert comprises sequences at the 5' and 3' end of the insert which are homologous to a region of a vector (herein referred to as 5' and 3' homologous sequences), in particular recombination sites of a vector which is targeted for integrating the vector insert. The 5' and 3' homologous sequences are fragments of DNA that is identical to recombination sites or has a sequence identity which is considered at least homologous. The 5' and 3' homologous sequences are preferably flanking said GOI, in particular immediately adjacent to said GOI or located upstream or downstream of the GOI. A vector insert is conveniently inserted into a circular or linear vector element, in particular a linearized vector, e.g. by homologous recombination of the 5'-terminus of the insert with the 3'-terminus of a linearized vector, and homologous recombination of the 3'-terminus of the insert with the 5'-terminus of a linearized vector. Upon recombination, the GOI is inserted and incorporated into the vector.

In some embodiments, the 5' and 3' homologous sequences are artificial sequences added to the insert, in particular on both sides of a GOI (e.g. by ligating artificial sequences to the 5' and 3' terminus of the GOI or to nucleotide sequences extending the GOI sequence). In some embodiments, the 5' and 3' homologous sequences are endogenous sequences of the GOI or an expression cassette comprising the GOI. In such embodiment, the 5' and 3' homologous sequences may be part of the protein encoding sequence or of upstream and downstream regulatory elements.

The 5' and 3' homologous sequences of the vector insert and/or the recombination sites of the vector backbone may each comprise or consist of at least any of 30, 50, 70, 100, 130, 150, 250, or 500, e.g. at least 30, and conveniently up to any of 1000, 500, or 300.

A "repertoire" as used herein refers to a population of diverse molecules which are variants of nucleic acids produced by mutagenesis of a nucleotide sequence referred. A repertoire of a GOI specifically includes a population of variants of a parent GOI, wherein the variants differ in at least one point mutation at a predefined position or randomly positioned within the GOI.

In some embodiments, variants of a parent GOI may be produced to obtain a repertoire of GOIs, wherein each of the variants have a certain sequence identity, e.g. any one of at least 60%, 70%, 80%, 90%, 95% sequence identity to the parent GOI. In some embodiments, each of the variants of a parent GOI in a repertoire of GOIs differ from the parent GOI in any one of at least 1, 2, 3, 4, 5, 10, 15, 20, 50, 100 nucleotides.

A repertoire of vector inserts may be produced, wherein the insert has a variable region comprised in the nucleotide sequence representing the GOI which is besides the 5' and 3' homologous regions. The variable region is specifically subject to mutagenesis to produce GOI variants which differ in at least one position (point mutation) within the variable region, while keeping the 5' and 3' homologous regions unchanged. As a result of mutagenesis, the library of vector inserts is produced, which includes a population or diversity of linear nucleotide constructs which differ in their nucleotide sequence, in particular in the GOI nucleotide sequence.

The term "mutagenesis" as used in the context of the present invention shall refer to a method of providing mutants of a nucleotide sequence, e.g. through insertion, deletion and/or substitution of one or more nucleotides, so to obtain variants thereof with at least one change in the non-coding or coding region. Mutagenesis may be through random, semi-random or site directed mutation. Specific GOI variants are derived from a parent GOI, which is e.g. a wild-type GOI which naturally occurs in a host organism. A mutagenesis method particularly encompasses those methods of engineering the nucleic acid or de novo synthesizing a nucleotide sequence using the a parent GOI information as a template. Specific mutagenesis methods apply rational engineering of variants.

Specific mutagenesis methods provide for point mutations of one or more nucleotides in a sequence, in particular tandem point mutations, such as to change at least 1, 2, 3, 4, 5, 6, 7, 8, 9, 10, or even more continuous nucleotides within the nucleotide sequence of the promoter. Such mutation is typically at least one of a deletion, insertion, and/or substitution of one or more nucleotides.

"Homologous recombination" (HR) as used herein refers to a type of genetic recombination in which nucleotide sequences (in particular DNA strands) of homologous nucleotide sequences are exchanged and thereby connected.

"Recombination site(s)" as used herein refers to one or more sequences on a first nucleotide compound which are homologous or sufficiently homologous to sequences on a second nucleotide compound to enable homologous recombination to occur between the two nucleotide compounds.

In certain embodiments, the vector backbones described herein comprise two or more homologous recombination site(s). The recombination site(s) may be part of/overlapping with the sequence elements present on the vector backbone, such as a promoter sequence, transcription terminator sequence, selection markers, sequences encoding the GOI or sequences of the vector backbone connecting such elements. In some embodiments, the vector backbone comprises two recombination sites (e.g. one recombination site on each end of a linear vector backbone). In some embodiments, the vector backbone comprises two recombination sites wherein the two recombination sites are split parts of a contiguous sequences. For example a contiguous sequence within a GOI sequence on a vector backbone is split into two parts, and the two parts are located at the two termini of the linear vector backbone (e.g. the contiguous sequence on a circular vector backbone is cleaved within said sequence thereby generating two parts), then a homologous sequence to the first part, i.e to a first recombination site, is added as 5'-homologous (flanking) sequence to a GOI and a homologous sequence to the second part, i.e. to a second recombination site, is added as 3'-homologous (flanking) sequence to the GOI. Upon transformation of the vector backbone comprising such recombination sites and the insert comprising the GOI with the respective flanking sequences, the GOI is integrated within the contiguous sequence of the GOI sequence. In some embodiments, the vector backbone comprises two recombination sites which are independent from each other, e.g. the first recombination site being a sequence within the promoter sequence which is followed by the sequence of a GOI, and the second recombination site being a sequence within the transcription termination sequence following the 3' end of the GOI. Upon transformation of such linear vector backbone (comprising the recombination sites at both ends) together with an insert comprising a variant of the GOI with 5' and 3' homologous (flanking) regions which are homologous to the first and second recombination sites, respectively, the variant GOI is inserted into the vector backbone thereby replacing the original GOI.

The term "promoter" as used herein refers to a DNA sequence capable of controlling the transcription of a coding sequence or functional RNA. The promoter of the invention specifically initiates, regulates, or otherwise mediates or controls the expression of a coding DNA. The promoter is recognized by RNA polymerase, which then initiates transcription. Thus, a promoter contains a DNA sequence that is either bound directly by, or is involved in the recruitment, of RNA polymerase. Promoter DNA and coding DNA may be from the same gene or from different genes, and may be from the same or different organisms. The promoter may be derived from the same or different species (e.g. yeast species) as the host cell used for protein expression. The promoter may also be a synthetic promoter, i.e., an artificially created nucleotide sequence that is not produced naturally but is a man-made design.

A promoter may include a TATA box sequence that acts as a recognition site to direct initiation of transcription, including, but not limited to one or more transcriptional enhancer elements. The enhancer elements (i.e. a regulatory element that can stimulate promoter activity) may be proximal or distal to the TATA box sequence and may be in a normal 5' to 3' orientation or may be in a 3' to 5' orientation. An enhancer element may be an enhancer element native to the promoter sequence or it may be a heterologous (i.e., the combination does not occur in nature) enhancer element inserted into the expression vector construct.

A promoter can be constitutive or regulatable. A constitutive promoter is understood to be a promoter whose expression is constant under the standard culturing conditions. Thus, a constitutive promoter controls expression without the need for induction, or the possibility of repression. A constitutive promoter can have some inducible activity, but the maximal activity obtained with the promoter is not inducible.

Regulatable promoters are promoters that are responsive to one or more induction cues. For example, a promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). A regulatable promoter can also be indirectly activated or repressed by one or more transcription factors that are themselves directly regulated by chemical or physical cues.

In some embodiments, the regulatable promoter is a carbon source regulatable promoter. In some embodiments, the promoter may be activated by the presence or a certain concentration of a specific carbon source, for example by the presence of methanol, lactose, galactose, glycerol, glucose, sucrose, citrate, formiate, lactate or acetate. Alternatively the promoter may be regulated by other substances, for example metal ions or tetracyclin. In some embodiments, the promoter may be repressed in a eukaryotic cell in the presence of an excess amount of a carbon source (e.g., during the growth phase of the cell culture) and de-repressed in the presence of a limited amount of a specific carbon source to exert strong promoter activity (e.g. in the production phase of the cell culture upon reduction of the amount of carbon, such as upon feeding of a growth limiting carbon source to a culture cultivated in a fed-batch process). In this regard, "carbon source regulatable" refers to the de-repression of a promoter by carbon (e.g. glucose or glycerol) consumption, reduction, shortcoming or depletion, or by limited addition of the carbon source so that it is readily consumed by the cells or by slow conversion to a repressing metabolite if the non-metabolized carbon source is not directly the repressing substance. Therefore one method to induce a de-repression effect may be the use of a glycerol kinase (GUT1) knockout strain or a strain with reduced GUT1 activity caused by an alternative promoter or less efficient GUT1 gene variant, which cannot efficiently metabolize glycerol to the repressing glycerol phosphate anymore. Reduced metabolization to the repressing glycerol3-phosphate may also be obtained by a deletion or down-regulation of glycerol transporter activity In some embodiments, the regulatable promoter is a fatty-acid inducible promoter, such as a promoter inducible with oleic acid.

In some embodiments, the promoter is a fungus or yeast promoter, such as a promoter from the yeast *Pichia, Candida, Torulopsis, Arxula, Hansenula, Yarrowia, Kluyveromyces, Saccharomyces, Komagataella*. Preferably the promoter is a promoter from the yeast *Pichia pastoris*.

Exemplary promoters that can be used in the plasmids and methods described herein include, but are not limited to CAT1, AOX1, GAP, AOD, AOX2, DAS1, DAS2, ENO1, FLD1, FMD, GPM1, HSP82, ICL1, ILV5, KAR2, KEX2, PET9, PEX8, PGK1, PHO89/NSP, SSA4, TEF1, THI11, TPI1, YPT1, GTH1, GCW14, and GUT1 or a functionally active variant thereof characterized by a certain sequence identity of e.g. at least 60%, or at least any of 70%, 80%, 90%, or 95%, or analogous promoter sequences thereof (i.e., a respective promoter sequence in another species).

In some embodiments, the promoter is a CAT1 promoter, i.e. a promoter driving transcription of the peroxisomal catalase gene. In some embodiments, the CAT1 promoter is the CAT1 promoter of *P. pastoris*. In some embodiments, the CAT1 promoter is the CAT1 promoter of another yeast or fungus, for example the CAT1 promoter of the yeast *S. cerevisiae, Hansenula polymorpha, Yarrowia lipolytica, Candida boidinii, Pichia stipitis, Schizosacharomyces pombe* or of filamentous fungi such as *Aspergillus niger, Aspergillus nidulans, Penicillium, Trichoderma*. In some embodiments, the promoter is the CAT1 promoter comprising the nucleotide sequence of SEQ ID NO:4 or a functionally active variant thereof.

In some embodiments, the promoter is a AOD promoter, i.e. a promoter driving transcription of the alcohol oxidase gene. In some embodiments, the AOD promoter is the AOD promoter of *Candida boidinii* (*C. boidinii*). In some embodiments the promoter is the AOD promoter comprising the nucleotide sequence of SEQ ID NO:5.

An "Autonomously Replicating Sequence" or "ARS" is a sequence that serves as an origin of DNA replication on eukaryotic chromosomes. An ARS, when incorporated into a DNA molecule, supports replication of the DNA molecule by binding a protein complex that unwinds and replicates the DNA. An ARS can be confirmed, i.e. functionally validated by incorporating the sequence into a DNA molecule that is not self-replicating in a given host and demonstrating that the DNA molecule replicates autonomously in the host only when the ARS is present.

In some embodiments the ARS comprises the nucleotide sequence of SEQ ID NO:2 or a functional variant thereof. In some embodiments, the ARS comprises the nucleotide sequence of SEQ ID NO:3 or a functional variant thereof. In some embodiments, the ARS comprises the nucleotide sequence of SEQ ID NO:5 or a functional variant thereof. In some embodiments, the ARS comprises the nucleotide sequence of any one SEQ ID NO:6-11 or a functional variant thereof.

In some embodiments, the ARS comprises a transcriptional terminator sequence. The term "transcription terminator" or "transcription terminator sequence" as used herein is intended to mean a sequence which leads to or initiates a stop of transcription of a nucleic acid sequence initiated from a promoter. A transcription terminator sequences may furthermore comprise sequences, which cause polyadenylation of the transcript, for example, comprise one or more polyadenylation signal sequences, or one or more polyadenylation attachment sequences.

The "functionally active" variant of an ARS or promoter sequence as used herein specifically means a mutant sequence, e.g. resulting from modification of a parent sequence by insertion, deletion or substitution of one or more nucleotides within the sequence or at either or both of the distal ends of the sequence, and which modification does not affect or impair the activity of this sequence. Functionally active variants may be generated by recombinant engineering, mutagenesis or by chemical synthesis.

In some embodiments, the functionally active variants of the promoter or ARS sequences disclosed herein are fragments of the parent sequence, e.g. fragments comprising at least 50%, at least 60%, at least 70%, at least 90% or at least 95% of the length of the parent sequence. Such fragments may be generated by deletion(s) of the parent sequence at the 5'-end and/or 3'-end of the parent sequence.

Functionally active variants of the promoter sequences disclosed herein will have minor variations that do not disrupt the promoter activity. Functionally active promoter variants include promoter sequences with at least about 60% nucleotide sequence identity, or at least any of 70%, 80%, 90%, or 95% sequence identity, to the promoter sequences disclosed herein and/or analogous promoter sequences (e.g., the respective promoter sequences of other yeast species such as the CAT1 promoter of *S. cerevisiae*). Functionally active variants also include engineered promoter variants, i.e., variants generated by mutagenesis, substitution, insertion or deletion of native promoter sequences.

By "functionally active promoter" or "functionally active promoter variant" is intended that the promoter or promoter variant initiates or enhances transcription. Those skilled in the art recognize that functionality of a promoter is readily determined by whether an operably linked nucleotide sequence is transcribed in the presence of the promoter. Methods of determining if transcription and translation occur are well known in the art and include measuring the mRNA production or protein production that occurs when a coding sequence for a protein of interest is placed under the control of the promoter. Necessarily, a promoter sequence incapable of inducing transcription or translation is non-functional.

Promoter activity may be determined by standard means, such as by measuring the quantity of expression products or the quantity of transcripts, e.g. employing a microarray, Northern Blot, RNA sequencing or qRT-PCR, digital PCR or else in a cell culture, such as by measuring the quantity of respective gene expression products in recombinant cells. See, for example, Sambrook et al. (1989) Molecular Cloning: *A Laboratory Manual* (2d ed., Cold Spring Harbor Laboratory Press, Cold Spring Harbor, N.Y.). Alternatively, levels of a reporter gene such as green fluorescent protein (GFP), luciferase, beta-galactosidase (lacZ), chloramphenicol acetyl transferase (CAT), or the like produced under the control of a promoter fragment or variant promoter sequence can be measured. See, for example, Astola et al. (2003); Hwang et al. (2003); Kim et al. (2000); Volckaert et al. (1994). Biological activity of the promoter can be measured using assays specifically designed for measuring the activity and or level of the polypeptide being expressed from the promoter. Such assays are known in the art.

The term "functionally active ARS" or "functionally active ARS variant" refers to an ARS that is capable of transforming a non-self replicating DNA construct into an autonomously replicating DNA construct upon insertion of the ARS into the DNA construct. ARS activity may be determined by the methods described herein or assays known in the art. Typically ARS function in yeast can be easily tested by transforming circular plasmids as demonstrated by (Liachko and Dunham, 2013; Liachko et al. 2010, 2014; Liachko, et al. 2013; Peng et al. 2015). For example, growth of single colony on selective media when ARS present as shown in Example 2 and FIG. 2C. Typically, plasmids without an ARS will give either no or very low numbers of transformants, whereas ARS containing plasmids show pronounced growth and the colony size may depend on the efficiency of the ARS. In addition, ARS function can be demonstrated on the molecular level by investigating replication intermediates by 2D gel analysis.

Functionally active ARS variants of the ARS sequences disclosed herein, i.e. functionally active ARS variants of ARS sequences comprising the nucleotide sequence of SEQ ID NO. 2, SEQ ID NO: 3 or SEQ ID NOs: 5-11, will have minor variations that do not disrupt ARS activity. Functionally active ARS variants include ARS sequences with at least about 60% nucleotide sequence identity to the ARS sequences disclosed herein and/or analogous ARS sequences or truncated versions of these sequences. In some embodiments, a functionally active ARS variant of any one of the ARS sequences disclosed herein shows at least 60% or at least any of 70% sequence identity, 80% sequence identity, 90% sequence identity, or 95% sequence identity to any one of SEQ ID Nos: 2, 3, 5-11. In some embodiments, a functionally active ARS variant of any one of the ARS sequences disclosed herein comprises or consists of a nucleotide sequence with any one of 1, 2, 3, 4, 5, 6, 7, 8, 9 up to 10 nucleotide substitution(s), insertion(s) and/or deletion(s) compared to the respective ARS sequence of SEQ ID NOs. 2, 3, 5 to 11.

The term "homology" or "homologous" as used herein indicates that two or more nucleotide sequences have the same or conserved base pairs at a corresponding position, to a certain degree, up to a degree close to 100%. A homologous sequence of the invention typically has at least about 60% nucleotide sequence identity, preferably at least about 70% identity, more preferably at least about 80% identity, more preferably at least about 90% identity, more preferably at least about 95% identity, more preferably at least about 98% or 99% identity. Specifically the term "homologous" characterize two nucleotide sequences or a variant compared to a parent sequence indicating the degree of sequence identity (homology) in that two or more nucleotide sequences have the same or conserved base pairs at a corresponding position, to a certain degree, up to 100% or a degree close to 100%.

The homologous promoter sequence or ARS sequence as described herein preferably has a certain homology to any of the native promoter or ARS nucleotide sequences of P. pastoris or to the heterologous C. boidinii ARS in at least specific parts of the nucleotide sequence.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity over the full length of the sequences being compared, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "heterologous" as used herein with respect to a nucleotide or amino acid sequence or protein, refers to a compound which is either foreign, i.e. "exogenous", such as not found in nature, to a given plasmid or host cell; or that is naturally found in a given plasmid or host cell, e.g., is "endogenous", however, in the context of a heterologous construct, e.g. employing a heterologous nucleic acid. The heterologous nucleotide sequence as found endogenously may also be produced in an unnatural, e.g. greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence is understood to be heterologous. An example of a heterologous polynucleotide is a GOI not natively associated with elements of a vector backbone as described herein, e.g. to obtain a hybrid plasmid, or a heterologous promoter operably linked to a GOI, as described herein. As a result, a hybrid or chimeric polynucleotide may be obtained. A further example of a heterologous compound is a POI encoding polynucleotide operably linked to a transcriptional control element, e.g., a promoter described herein, to which an endogenous, naturally-occurring POI coding sequence is not normally operably linked.

Specific embodiments of heterologous sequences are derived from a species or strains and transferred to another strain or species which differs from the original (parent) one. It is expressly understood that any of the heterologous promoter or ARS sequences of the present invention that are derived from species other than P. pastoris, e.g. from other yeast species, may comprise a homologous sequence, i.e. a sequence with a certain homology as described herein. Thus, the term "homologous" may also include heterologous sequences. On the other hand, it is understood that the invention also refers to heterologous sequences and homologs thereof that comprise a certain homology.

The term "operably linked" as used herein refers to the association of nucleotide sequences on a single nucleic acid molecule, e.g. a vector, in a way such that the function of one or more nucleotide sequences is affected by at least one other nucleotide sequence present on said nucleic acid molecule. For example, a promoter is operably linked with a coding sequence of a recombinant gene or GOI, when it is capable of effecting the expression of that coding sequence. As a further example, a nucleic acid encoding a signal peptide is operably linked to a nucleic acid sequence encoding a POI, when it is capable of expressing a protein in the secreted form, such as a preform of a mature protein or the mature protein. Specifically, such nucleic acids operably linked to each other may be immediately linked, i.e. without further elements or nucleic acid sequences in between the nucleic acid encoding the signal peptide and the nucleic acid sequence encoding a POI.

A promoter sequence is typically understood to be operably linked to a coding sequence, if the promoter controls the transcription of the coding sequence. If a promoter sequence is not natively associated with the coding sequence, its transcription is either not controlled by the promoter in native (wild-type) cells or the sequences are recombined with different contiguous sequences.

The ARS comprised in the episomal plasmid described herein is characterized by not being operably linked to the GOI or any promoter that is operably linked to the GOI. Therefore, the ARS is considered as a nucleotide sequence which is expressing its function independent of the GOI expression or a respective promoter which controls the GOI expression. Though the ARS may be derived from a native promoter sequence, its function in the episomal plasmid described herein is not the function of a promoter controlling the expression of a GOI. In specific cases, it is preferred that the ARS is positioned outside an expression cassette that comprises the GOI.

A "selectable marker" or "selection marker" refers to a gene (or the encoded polypeptide) that confers a phenotype which allows the organism expressing the gene to survive under selective conditions. A selectable marker generally is a molecule that, when present or expressed in a cell, provides a selective advantage (or disadvantage) to the cell containing the marker. For example, the genetic markers for selection of transformants can include the ability to grow in the presence of an agent that otherwise would kill the cell, the ability to grow in the absence of a particular nutrient, a selection marker that allows a transformed cell to grow on a medium devoid of a necessary nutrient that cannot be produced by a deficient and untransformed cell, a selection marker that allows a transformed cell to grow on medium, e.g., an energy source, that cannot be used/metabolized by a deficient and untransformed cell, or a selection marker that encodes an enzyme for which chromogenic substrates are known.

In some embodiments, the selection marker provides resistance to a drug, including, but not limited to, G418/Geneticin, Nourseothricin (Nat), Zeocin, Blasticidin, Hygromycin, fluoroacetamide, and 2-deoxyglucose. In some embodiments, the selection marker provides resistance to a gene encoding a protein causing cell death such as a killer toxin or the ribonuclease MazF.

The selectable marker system may include an auxotrophic mutant *P. pastoris* host strain and a wild type gene which complements the host's defect, herein referred to as selection marker based on auxotrophy. Examples of such selectable marker systems include, but are not limited to amino acid auxotrophy such as arginine, methionine or histidine auxotrophy or nucleotide biosynthesis auxotrophy such as uracil auxotrophy or thymidine auxotrophy.

The selectable marker system may include a wildtype or mutant *P. pastoris* host strain, which is not able to use certain nutrients and a gene which complements the host's defect. Examples of such selectable marker systems include, but are not limited to glycerol utilization, sucrose utilization, methanol utilization, inulin utilization, cellobiose utilization, and nitrogen source utilization.

In some embodiments, the selection marker is based on glycerol utilization, where the cell is unable to metabolize glycerol efficiently to use it as a carbon source for growth. For example, a cell deficient in the gene encoding glycerol kinase, GUT1, such as a *P. pastoris* gut-1 knock out strain, which does not grow well in the presence of glycerol unless transformed with a complementation plasmid containing the wild-type GUT1 gene. In some embodiments, the *S. cerevisiae* or *P. pastoris* HIS4 gene is used to complement his4 *Pichia* mutant strains. In some embodiments, the *S. cerevisiae* or *P. pastoris* ARG4 gene is used to complement *P. pastoris* arg mutants. Also met2, ade1, ura3 and ura5 auxotrophies can be complemented using the respective wildtype genes MET2, ADE1, URA3 and URA5.

The episomal plasmid vector specifically described herein comprises the ARS of SEQ ID NO:2, SEQ ID NO:3, SEQ ID NO:5, or SEQ ID NO:6-11, or a functional variant of any of the foregoing. In some embodiments, the episomal plasmid vector further comprises a promoter sequence (e.g., a fungal or yeast promoter sequence) including but not limited to upstream sequences linked to the genes CAT1, AOX1, GAP, AOD, AOX2, DAS1, DAS2, ENO1, FLD1, FMD, GPM1, HSP82, ICL1, ILV5, KAR2, KEX2, PET9, PEX8, PGK1, PHO89/NSP, SSA4, TEF1, THI11, TPI1, YPT1, GTH1, GCW14, and GUT1 of *P. pastoris* or a functionally active variant thereof or (heterologous) promoter sequences linked to the homologs and/or analogues of these genes from other organisms. For example, the episomal plasmid vector comprises the CAT promoter of *P. pastoris* or other yeasts or the promoter of the alcohol oxidase gene of *C. boidinii* or other yeasts In some embodiments, the episomal plasmid vector comprises the ARS of SEQ ID NO:2 or SEQ ID NO:3, or a functionally active variant of SEQ ID NO:2 or SEQ ID NO:3, or the ARS of SEQ ID NO:5 or a functionally active variant thereof and a CAT1 promoter sequence (e.g., a fungal or yeast CAT1 promoter sequence such as the CAT1 promoter sequence of *P. pastoris*, *S. cerevisiae* or *A. nidulans*) or a functionally active variant thereof or the *C. boidinii* AOD promoter sequence (SEQ ID NO:5) or variants thereof such as SEQ ID NO:6-11. Preferred embodiments are any combinations of SEQ ID NO:2, SEQ ID NO:3, SEQ ID NO:5, or SEQ ID NO:6-11, or functionally active variants thereof with the CAT1 promoter or with the AOX1 promoter, or with the histone promoters, or with the GAP promoter or with DAS promoters, or with functionally active variants thereof.

In some embodiments, the plasmid comprises an ARS sequence (i.e., the ARS sequence of SEQ ID NO:2, SEQ ID NO:3, or SEQ ID NO: 5 or a functionally active variant of any of the foregoing, such as the ARS of SEQ ID NO:6-11), a promoter sequence and a transcription terminator sequence which are arranged overlappingly over a sequence of less than 700 base pairs. "Overlappingly" as used herein indicates that the ARS, promoter and/or terminator sequence have one or more nucleotide positions (e.g. at least 5, 10, 15, 25, 50, 100) in common. For example one or more nucleotide positions (e.g. at least 5, 10, 15, 25, 50, 100, 200) at the 5'end of the promoter sequence may be part of the ARS sequence and the ARS and the transcriptional terminator might totally overlap (Ref: Chen et al, NAR 1996).

As used herein, a "contiguous DNA sequence" is a DNA sequence that includes specified elements (e.g., an ARS and a promoter sequence) which elements are substantially uninterrupted by unspecified elements.

The term "cell" or "host cell" as used herein refers to a cell or an established clone of a particular cell type that has acquired the ability to proliferate over a prolonged period of time. A host cell particularly includes a recombinant construct, e.g. engineered to express recombinant genes or products. The term "host cell" also refers to a recombinant cell line as used for expressing a gene or products of a metabolic pathway to produce polypeptides or cell metabolites mediated by such polypeptides, including production cell lines, which are ready-to-use for cultivation in a bioreactor to obtain the product of a production process, such as a protein of interest (POI) or a cell metabolite. The cells may be specifically prokaryotic or eukaryotic, including mammalian, insect, yeast, filamentous fungi and plant cells. In some embodiments the host cell is a yeast cell, specifically the yeast *Pichia, Candida, Torulopsis, Arxula, Hansenula, Yarrowia, Kluyveromyces, Saccharomyces, Komagataella*. Preferably the host cell is a *P. pastoris* cell, in particular a wild-type strain or a mutated strain, preferably a KU70 deletion strain of *P. pastoris*.

The *P. pastoris* strain may be a wild type strain or a genetically engineered strain such as a knockout strain (Näätsaari et al. 2012). In some embodiments the GUT1 knockout strain is utilized.

The term "cell culture" or "cultivation", also termed "fermentation", with respect to a host cell described herein is meant the maintenance of cells in an artificial, e.g., an in vitro environment, under conditions favoring growth, differentiation, protein expression or continued viability, in an active or quiescent state, of the cells, specifically in a controlled bioreactor according to methods known in the industry. The host cell culture may be a batch culture, a fed-batch culture or continuous culture, specifically when the host cell culture is performed for expressing a GOI and producing a POI.

The term "batch culture" as used herein refers to a method of culturing cells in which all the components that will ultimately be used in culturing the cells, including the medium as well as the cells themselves, are provided at the beginning of the culturing process. A batch culture is typically stopped at some point and the cells and/or components in the medium are harvested and optionally purified.

The term "fed-batch culture" as used herein refers to a method of culturing cells in which additional components are provided to the culture at some time subsequent to the beginning of the culture process either periodically or continuously. The provided components typically comprise nutritional supplements for the cells that have been depleted during the culturing process. The fed-batch strategy is typically used in bio-industrial processes to reach a high cell density in the bioreactor. The controlled addition of the nutritional components, e.g., carbon substrate, directly affects the growth rate of the culture and helps to avoid overflow metabolism or the formation of unwanted metabolic byproducts. A fed-batch culture is typically stopped at some point and the cells and/or components in the medium are harvested and optionally purified.

A fed-batch process may be based on feeding of a growth limiting nutrient substrate (e.g. carbon source) to a culture. For example, under carbon source limited conditions, the carbon source specifically may be contained in the feed of a fed-batch process. Thereby, the carbon substrate is provided in a limited amount.

A "continuous culture" is used herein to describe a culture characterized by both a continuous inflow of a liquid nutrient feed and a continuous liquid outflow. Also in a continuous culture the growth rate can be tightly controlled.

The term "carbon source" as used herein shall mean a fermentable carbon substrate, typically a source carbohydrate, suitable as an energy source capable of being metabolized by host organisms or cell cultures, in particular sources selected from the group consisting of monosaccharides (e.g., glucose, fructose, sorbitol, galactose or mannose) disaccharides (e.g., sucrose), oligosaccharides, polysaccharides, alcohols including glycerol, methanol and ethanol, in the purified form, in minimal media or provided in raw materials, such as a complex nutrient material. The carbon source may be used as a single carbon source or as a mixture of different carbon sources such as a mixture of a hexose such as glucose, and an alcohol, such as glycerol or ethanol.

As used herein, the term "expression" refers to the process by which a polypeptide is produced based on the nucleic acid sequence of a gene. The process generally includes both transcription and translation. Expression can be determined at the protein or nucleic acid level, using methods known in the art including Northern hybridization analysis, reverse-transcription-based quantitative PCR assays, digital PCR, microarray analysis, Western blot, immunoassays, fluorescence of reporter proteins or tagged proteins, or assays based on the biological activity of the protein (e.g. enzymatic assays).

For example, the activity of the biocatalysts such as the hydroxynitrile lyase from *Manihot esculenta* (MeHNL) and *Linum usitatissimum* (LuHNL) may be determined using assays based on cleavage of cyanohydrin. Such assays are well known in the art.

LuHNL activity may be measured by mixing lysate supernatants or dilutions thereof with citrate phosphate buffer (pH 5.0, 50 mM) and the substrate acetone cyanohydrin (300 mM) dissolved in citric acid (100 mM). The samples are incubated for 10 min and subsequently N-chlorosuccinimide (100 mM) and succinimide (1 M) are added to stop the reaction (incubated for 5 min). Barbituric acid (125 mM) and isonicotinic acid (65 mM) in 0.2 M NaOH are added for color development, which is measured at 600 nm for 10 min. A calibration curve with potassium cyanide (KCN) in a range of 0.025 to 0.2 mM is used to determine the absolute activities.

MeHNL activity may be determined using a mandelonitrile cyanogenesis assay described in literature (Wiedner et al. 2014) using a final mandelonitrile concentration of 15 mM.

Expression levels of fluorescent reporter proteins such as eGFP may be determined by measuring fluorescence at the main excitation/emission wavelengths (for eGFP at excitation/emission, ex./em., wavelengths of 488/507 nm) and absorption (600 nm, OD600) as described in (Vogl et al. 2014).

As used herein the term "transformation" refers to the introduction of a plasmid vector or vector backbone and/or insert into a cell. Accordingly, a cell into which a plasmid vector has been introduced is considered a "transformant."

Transformation efficiency may be determined by calculating colony forming units per µg of transformed DNA. The transformation rates are specific for the used vector or vector backbone and the employed amount of DNA and might vary when other vectors or DNA concentrations are used. For example transformation rates usually drop with an increase of the vector size and with higher amounts of DNA used for transformation. When lower amounts of DNA are used (for example 10 ng/transformation) then transformation rates are calculated and related to 1 µg of DNA. This may result in higher transformation rates compared to the rate obtained from direct transformation with 1 µg of DNA.

The term "uniform" protein expression as used herein refers to less variable expression levels of the POI between different transformants or between different cultures inoculated with the same transformant.

As described herein it was surprisingly found that the plasmid vectors described herein are capable of stable and increased expression of proteins of interest. Further, transformation of eukaryotic cells with the plasmid vectors described herein results in increased transformation efficiencies and uniform protein expression between individual transformants.

Provided herein are methods of transforming *P. pastoris* with an episomal plasmid, isolating such plasmid from *P. pastoris* and of directly using such isolation for the transformation of competent *P. pastoris* cells again. Such method does not rely on *E. coli* to amplify plasmid DNA for transformation of *Pichia* and accelerates breeding cycles for example for directed enzyme evolution or antibody engineering employing *P. pastoris* as a host.

Provided herein are methods of expressing a POI in a eukaryotic cell using the plasmid vectors as described herein. In some embodiments, the cells are cultivated under selective conditions, e.g., in the presence of a drug such as zeocin or geneticin or a nutrient which is not tolerated/metabolized by a cell not being transformed with a plasmid vector as described herein.

In some embodiments, expression of a POI is increased at least 1.5 fold, preferably at least 3 fold, more preferably at least 5 fold or at least 10 fold compared to protein expression of the same POI using genomic integration of a linear expression cassette comprising the gene of interest encoding the POI.

In some embodiments, transformation efficiency of a plasmid vector described herein comprising a gene of interest is increased at least 20 fold compared to transformation efficiency of a linear expression cassette comprising said gene of interest. In some embodiments, transformation is increased at least 50 fold, at least 100 fold, at least 200 fold, at least 300 fold, at least 500 fold, or at least 500 fold.

In some embodiments, protein expression of a POI in individual transformants with an episomal plasmid vector as described herein is at least 1.5 fold more uniform compared to protein expression using genomic integration of a linear expression cassette comprising the gene of interest encoding said POI.

In some embodiments, protein expression of individual transformants obtained with the episomal plasmid vectors described herein is at least 1.2 fold more uniform compared to protein expression using episomal plasmid based expression employing a state of the art *P. pastoris* ARS1 based plasmid with an expression cassette comprising the gene of interest encoding the POI.

Protein expression and/or transformation efficiency using the methods and episomal plasmids described herein may be influenced/regulated by the type of selection marker and may also vary if variants of the selection marker or alternative promoters or terminators driving transcription of a selection marker are used. For example, protein expression of a particular POI may be increased using Geneticin as selection marker compared to using Zeocin resistance. Methods of determining protein expression to compare the respective expression levels are known in the art and described herein.

The plasmid copy number maintained in the cell may vary, if selection pressure is applied, depend on the employed selection marker and may also vary in dependence of the concentration of the substance used for selection. Analytical methods to determine plasmid copy numbers are known in the art and include for example qPCR, digital PCR, Southern Blotting or other hybridization techniques.

Protein expression and/or transformation efficiency using the methods and plasmids described herein may also be influenced by cultivation methods such as type of nutrients, feed rates and/or concentration of nutrients and/or the concentration of compounds added to the media to tune the selection pressure.

Furthermore provided herein are methods of generating episomal plasmid vectors in *Pichia pastoris* using in vivo homologous recombination. Specifically, the inventors have found that transformation of (i) ARS based vectors (in particular vectors comprising an ARS sequence of *C. boidinii* such as sequences comprising SEQ ID NO: 5-11) comprising homologous recombination site(s) together with (ii) inserts comprising a GOI with 5' end 3' flanking sequences that are homologous to the recombination site(s) on the vector into a KU70 deletion strain of *Pichia pastoris* results in episomal plasmids comprising the GOI. Notably, vectors comprising ARS sequences from yeast other than *P. pastoris*, are functional in a *Pichia pastoris*.

The term "*Pichia pastoris*" as used herein shall refer to methylotrophic yeasts including several different species such as from *Pichia* or *Komagataella*, e.g. *Pichia pastoris*, or *Komagataella pastoris*, or *K. phaffii*, or *K. pseudopastoris*. Examples of *P. pastoris* strains include CBS 704 (=NRRL Y-1603=DSMZ 70382), CBS 2612 (=NRRL Y-7556), CBS 7435 (=NRRL Y-11430), CBS 9173-9189 (CBS strains: CBS-KNAW Fungal Biodiversity Centre, Centraalbureau voor Schimmelcultures, Utrecht, The Netherlands), and DSMZ 70877 (German Collection of Microorganisms and Cell Cultures), but also strains from Invitrogen, such as X-33, GS115, KM71 and SMD1168, or from BioGrammatics, Inc., such as BG10 and mutants thereof, e.g. BG11.

The term "*Pichia pastoris* KU70 deletion strain" as used herein refers to a *Pichia pastoris* strain (e.g. the wild-type strain CBS7435 (NRRL-Y11430, ATCC 76273) or the GS115 strain in which the *Pichia pastoris* homologue of the ku70 gene (e.g. the ku70 gene of *P. pastoris* with Accession No: XM_002492501.1; FR839630, region 1598101-1599963) has been modified (e.g. deleted or disrupted) at the genomic level to eliminate functional KU70 activity, e.g. to inhibit the activity or functionality. This includes, but is not limited to, complete or partial deletion of the gene (comprising the promoter, open reading frame and terminator); introduction of one or more mutations that alter transcription or translation of the gene or encoded mRNA, respectively; and introduction of one or more mutations that inactivate the protein activities. Examples in which protein activity/functionality can be abrogated or disrupted include, but are not limited to, 1) deletion or disruption of the upstream or downstream regulatory sequences controlling expression of the gene; 2) mutation of the gene encoding the protein activity to render the gene non-functional, where "mutation" includes deletion, substitution, insertion, or addition into the gene to render it incapable of activity.

In some embodiments, the KU70 deletion strain is a *P. pastoris* strain comprising a partially deleted ku70 gene with a partial deletion of the ku70 gene, thereby inactivating the gene or its expression product. In some embodiments, the KU70 deletion strain is a *P. pastoris* strain with a gene deletion of the KU70 homologue of *P. pastoris* as described in Nääatsaari et al. 2012. The KU70 homologue of *P. pastoris* is characterized by the sequence information identified In FIG. 33 (SEQ ID 87).

The KU70 deletion strain used for the purpose described herein was surprisingly suitable for biosynthesis and stably maintaining the episomal plasmid described herein over a long period of time.

EXAMPLES

The Examples which follow are set forth to aid in the understanding of the invention but are not intended to, and should not be construed to limit the scope of the invention in any way. The Examples do not include detailed descriptions of conventional methods, e.g., cloning, transfection, and basic aspects of methods for overexpressing proteins in microbial host cells. Such methods are well known to those of ordinary skill in the art.

Materials and Methods

Strains, Materials, Media and Cultivations Conditions

For cloning and plasmid propagation an *Escherichia coli* Top10 F' strain was used. *P. pastoris* transformations were mostly performed with the CBS7435 wildtype strain and an AOX1 deletion variant thereof (Näätsaari et al. 2012). Alternatively *P. pastoris* BG10, which is a killer plasmid free derivative of the NRLL-Y-11430 wt strain and BG11, the AOX1 deletion variant thereof were used (both strains obtained from bisy e.U., Hofstaetten, Austria). The GUT1 complementation plasmids (Näätsaari et al. 2012) were transformed into a gut1 knockout variant of the CBS7435 wt strain. Kits for plasmid isolation, gel purification and enzymes for cloning were used as recently described (Vogl et al. 2014). Gibson assemblies were performed following standard procedures (Gibson et al. 2009) using T5 exonuclease and Taq DNA ligase from New England Biolabs (Ipswich, Mass., USA) and Phusion polymerase from Thermo Fisher Scientific (Waltham, Mass., USA). Sanger sequencing was performed by LGC Genomics GmbH (Berlin, Germany) and Microsynth AG (Balgach, Switzerland). Media were prepared as outlined by Weis et al. (2004), in short standard buffered minimal media with 1% (w/v) glucose/dextrose (BMD) and full media (yeast extract, peptone, 2% glucose; YPD) were used. Additionally also buffered minimal medium with 1% (w/v) glycerol (BMG) was used (Näätsaari et al. 2012). The following antibiotic concentrations were used: *E. coli*: LB-medium containing 25 µg/ml Zeocin, 50 µg/ml Kanamycin, 100 µg/ml Ampicillin; *P. pastoris*: 100 µg/ml Zeocin, 300 µg/ml Geneticin. Zeocin selection in liquid minimal BMD media was attempted, but failed (presumably because of the pH or the high ionic strength). Therefore we used full media for Zeocin and Geneticin selection experiments. Deep well plate cultivations were performed as previously described (Weis et al. 2004), however no methanol induction was required for $P_{CAT1}$ driven expression and the protocol therefore stopped after growth on glucose and its depletion. Shake flask cultivations were performed in 250 ml baffled flask (25 ml BMD starting volume) with a starting $OD_{600}$ of 0.05. The flasks were induced after 48 h with 25 ml BMM2 (1% methanol v/v to achieve a final concentration of 0.5%) and after 12 h, 24 h after the first induction with BMM10 (5% methanol v/v) (Weis et al. 2004). Glucose concentrations were measured using a hexokinase method based kit (Glucose UV kit, DIPROmed (Vienna, Austria)).

Plasmid Construction eGFP reporter gene constructs with different selection markers are based on the shuttle vectors reported by Näätsaari et al. (2012). For Zeocin selection we used the restriction site free cloning (RSFC) vector pPpT4mutZeoMlyI-intArg4-eGFP-Bmrlstuffer previously reported (Vogl et al. 2015 based on the pPpT4_S vector (Näätsaari et al., 2012). $P_{CAT1-1000}$, $P_{CAT1-692}$ and $P_{CAT1-500}$ vectors were available from a previous study.

The 264 bp putative ARS identified in the $P_{CAT1-692}$ promoter fragment (putARS-$P_{CAT1}$) was cloned into the above mentioned eGFP RSFC reporter vector by replacing the stuffer fragment by Gibson assembly (Gibson et al., 2009) after PCR amplification using primers intARG4-pCAT1-764-Gib and eGFP-pCAT1-501rev-Gib (see Table 1) and followed by sequence verification.

Gibson, the ampicillin cassette with primers GUT1TT-AmpR-Gibson and pUC-Ori-AmpR-Gibson. The two PCR fragments were assembled with the above mentioned BamHI and PstI backbone.

Transformation, Fluorescence Measurements and Gut1 Strain

Competent P. pastoris cells were prepared and transformed using the condensed protocol of Lin-Cereghino et al. (Lin-Cereghino et al., 2005). If applicable, plasmids were linearized with SwaI and one μg transformed, for circular plasmids 10 ng were transformed. To avoid contaminations of linearized plasmids with uncut circular forms, the linearization reactions were loaded on agarose gels and the band corresponding to the linearized form was cut and purified.

eGFP fluorescence (ex./em. 488/507 nm) and absorption (600 nm, $OD_{600}$) were measured and normalized using a Synergy MX plate reader (Biotek, Winooski, Vt., USA) as outlined previously (Vogl et al., 2014).

The gut1 knock-out strain reported previously (Näätsaari et al. 2012) was achieved in a ku70 knockout strain. We aimed to use the wildtype strain background and created a gut1 knockout following a similar strategy as Näätsaari et al.

TABLE 1

Primers used in this study.

| Name | Sequence |
| --- | --- |
| intARG4-pCAT1-764-Gib | Gttagtagatatttataccattctgcgagaaggtcctaaaagtgcgaggaagaataaaaatactgcttc; SEQ ID NO: 14 |
| eGFP-pCAT1-501rev-Gib | Agtgaaaagttcttctcctttgctagccatcgtagaaaaaaatgtggtgaaacagtttcataagagttatatac; SEQ ID NO: 15 |
| AOX1TT-BamHI-pILV5-Gibson | Cagaagattaagtgagaccttcgtttgtgcggatccttcagtaatgtcttgtttcttttgttgcag; SEQ ID NO: 16 |
| pUC-Ori-PstI-AODTT-Gibson | Ctacggggtctgacgctcagtggtacctgcagctaaggtaatcagatccaagtttccccaatc; SEQ ID NO: 17 |
| AOX1TT-BamHI-pGUT1-Gibson | Cagaagattaagtgagaccttcgtttgtgcggatccataccgaaaggtaaacaacttcggggaattg; SEQ ID NO: 18 |
| AmpR-GUT1TT-Gibson | Ggcgtatcacgaggccctttcgtctgccagagctgtcacatacttgaaatagggttg SEQ ID NO: 19 |
| GUT1TT-AmpR-Gibson | Caaccctatttcaagtatgtgacagctctggcagacgaaagggcctcgtgatacgcc SEQ ID NO: 20 |
| pUC-Ori-AmpR-Gibson | Gatcttttctacggggtctgacgctcagtaacgaaaactcacgttaagggattttggtc SEQ ID NO: 21 |

The one piece combination of the ARS and $P_{CAT1}$ ($P_{CAT1-692}$) was also tested with alternative selection markers Geneticin and gut1 complementation (Näätsaari et al., 2012). For Geneticin selection, the resistance cassette of the Zeocin vector was replaced with the Kanamycin/Geneticin cassette from pPpKan_S (Näätsaari et al., 2012) (this cassette confers resistance to Kanamycin in E. coli and Geneticin in P. pastoris). The GUT1 cassette was amplified from pPpGUT1r (Näätsaari et al., 2012) (glycerol complementation for P. pastoris, Ampicillin for E. coli).

The Zeocin based reporter vector containing $P_{CAT1-692}$ was digested with BamHI and PstI and the backbones gel purified. The Kan/Gen resistance cassette was PCR amplified from pPpKan_S using primers AOX1TT-BamHI-pILV5-Gibson+pUC-Ori-PstI-AODTT-Gibson and incorporated into the vector backbones by Gibson assembly. The GUT1 cassette was amplified from pPpGUT1 using primers AOX1TT-BamHI-pGUT1-Gibson and AmpR-GUT1TT- (2012). The strain was identified by screening transformants obtained on YPD+Zeo media for abolished growth on glycerol.

Example 1: Mapping the ARS Region of $P_{CAT1}$

The $P_{CAT1}$ length previously used was selected upstream from the start codon of the CAT1 gene up to the end of the adjacent gene LCP5, resulting in a 692 bp fragment ($P_{CAT1-692}$; FIG. 1A). Analysis of the promoter sequence revealed an AT-rich stretch in the 5' end of $P_{CAT1-692}$ (FIG. 1A). Shortening the promoter to 500 bp length ($P_{CAT1-500}$) removes the AT-rich stretch. AT-rich sequences are a common trait of transcription terminators and ARSs (Chen, Reger, Miller, & Hyman, 1996). Recently ARSs of P. pastoris have been mapped by a high-throughput screen (Liachko et al. 2014) based on deep sequencing (ARS-seq. (Liachko et al. 2013)). Liachko et al. (2014) thereby identified an ARS in $P_{CAT1}$ and mapped the functional core to a 388 bp fragment (FIG. 1A). No functional analyses were performed by Liachko et al.

We cloned different fragments of $P_{CAT1}$ into a vector containing an enhanced green fluorescent protein (eGFP) reporter gene to test if this ARS in $P_{CAT1}$ is causing strain instabilities and background growth (small colonies) especially in case if stress situations such as transformations or freeze/thaw cycles. $P_{CAT1-1000}$, $P_{CAT1-692}$ and $P_{CAT1-500}$ provide different lengths of the promoter, the AT-rich stretch (264 bp) was selected as putative ARS of $P_{CAT1}$ (putARS-$P_{CAT1}$) with a shorter length than the functional core of Liachko et al. (FIG. 1A).

Figure 2A:
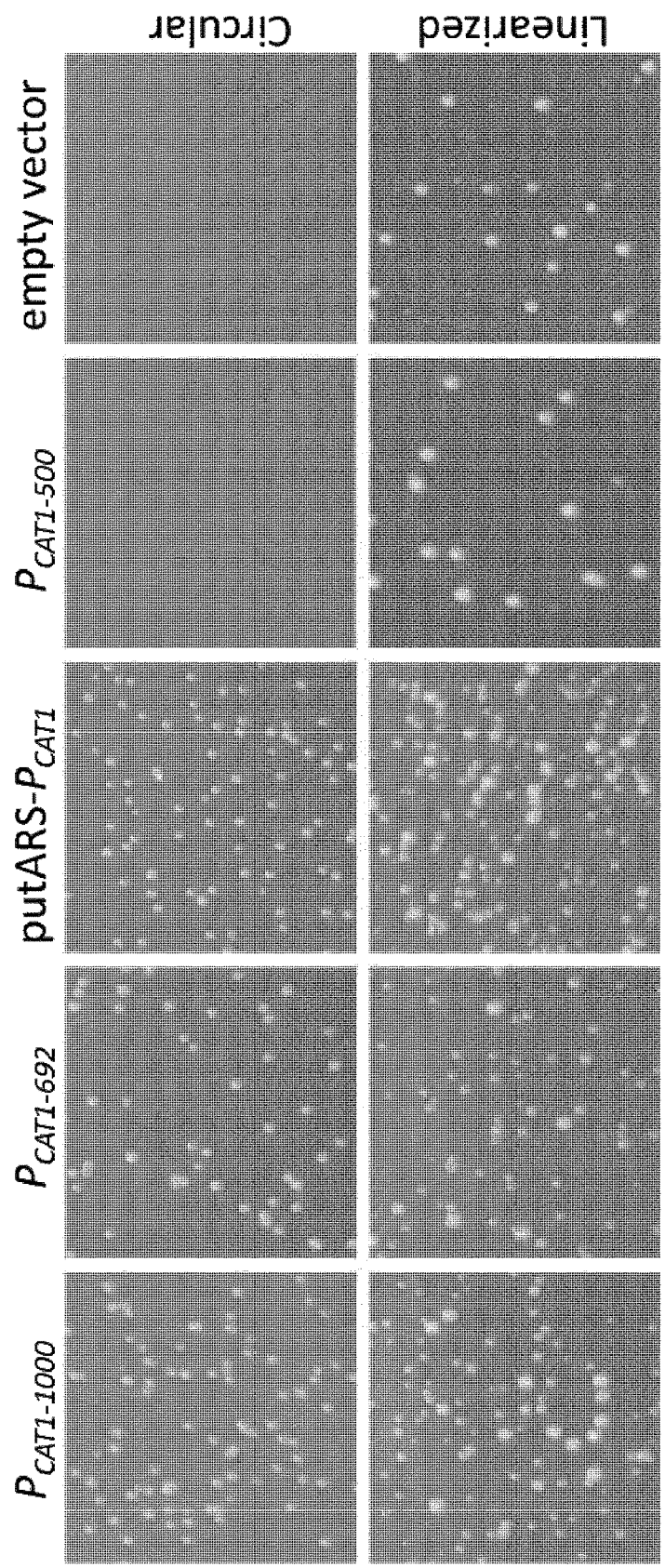
Figure 2B:
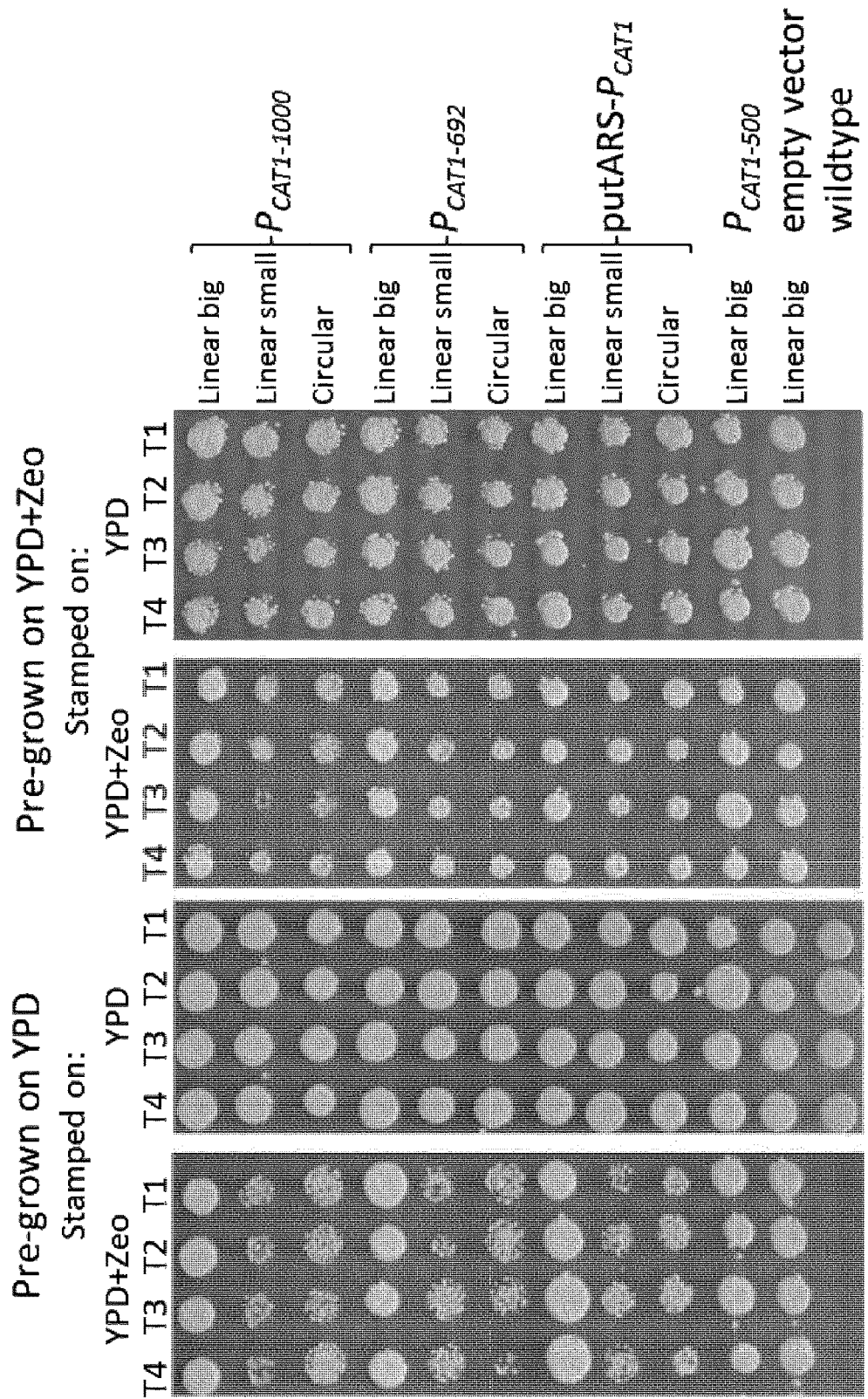

P. pastoris cells were transformed with both circular and linearized forms of these vectors (FIG. 2A). Linearization of plasmids results in highly recombinogenic DNA ends which drastically increase genomic integration rates compared to the circular form in yeast (Orr-Weaver, Szostak, & Rothstein, 1981). Standard P. pastoris vectors do not contain ARSs and cannot replicate episomally. Therefore transformation of cells with the circular form of the empty vector as control did not give any colonies (FIG. 2A). Transformation with the circular forms of $P_{CAT1-1000}$, $P_{CAT1-692}$ and putARS-$P_{CAT1}$ did however show pronounced growth, whereas $P_{CAT1-500}$ did not show any growth. Transformations with linearized forms of the plasmids resulted in transformants for all plasmids. These results confirm the function of the AT-rich stretch of $P_{CAT1}$ as ARS.

Figure 1B:
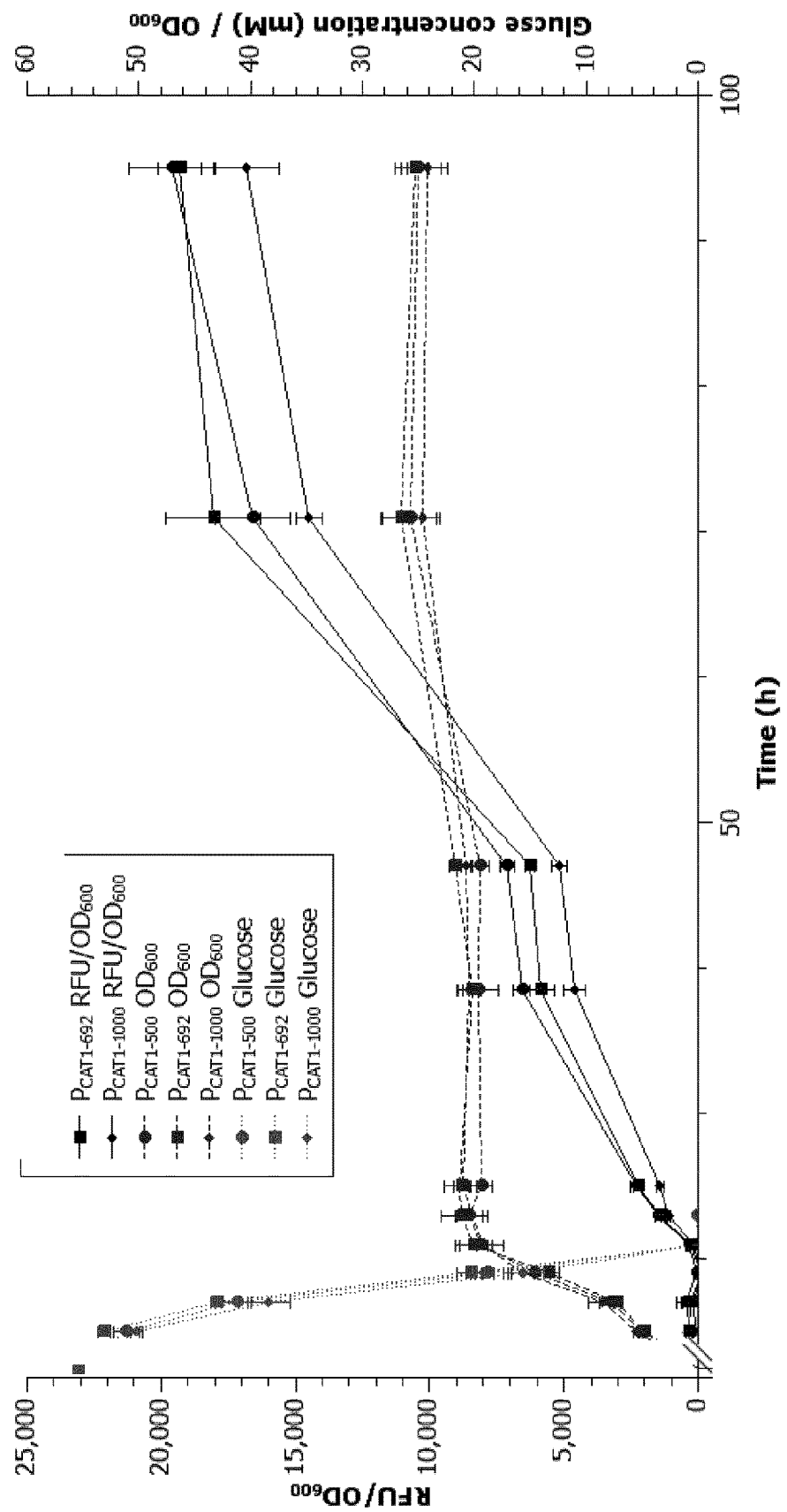

Transformants with stable genomic integration of any promoter length tested showed identical reporter fluorescence (FIG. 1B, FIG. 3A), suggesting that the length of the ARS part is not affecting the strength of $P_{CAT1}$. Also the regulatory profile (repression/derepression/induction) was not affected, as demonstrated by comparing the three different promoter lengths in a time series (FIG. 1B). As these sequences behaved identically, it was concluded that the ARS is not required for the transcriptional regulation of $P_{CAT1}$ by any means.

Example 2: Vectors Bearing the ARS of $P_{CAT1}$ can Replicate Episomally Even after Linearization For transformations with linearized ARS containing sequences ($P_{CAT1-1000}$, $P_{CAT1-692}$ and putARS-$P_{CAT1}$) two distinct types of colonies could be noticed: Big colonies (of similar size as the empty vector control and $P_{CAT1-500}$) and smaller colonies (FIG. 2A). If the cells are incubated longer, the difference between the colonies gets less pronounced, suggesting different growth rates.

To determine whether the small colonies may be episomal, non-genomically integrated versions of these vectors, similar to transformants of the circular plasmids, big and small colonies of the constructs were grown in liquid culture in 96 well deep well plates under selective (YPD+Zeocin) and non-selective conditions (YPD) and subsequently stamped to selective and non-selective media (FIG. 2B). Big colonies of any construct showed uniform growth independent of the cultivation conditions with sizes comparable to colonies of the empty vector. Small colonies showed identical growth to big colonies on non-selective media. But if small colonies were transferred from non-selective media to selective media, they showed weak growth similar to circular plasmids. This would be the expected outcome for episomal plasmids: Under non-selective conditions the plasmids are not efficiently propagated and only maintained in a subset of the cell population, resulting in weaker growth. If the small colonies or circular plasmids are pre-grown under selective conditions, plasmid loss is depending on the experimental conditions: Either less severe than under non-selective conditions (FIG. 2B) or completely rescued (FIG. 6), fully restoring growth under selective conditions.

Figure 2C:
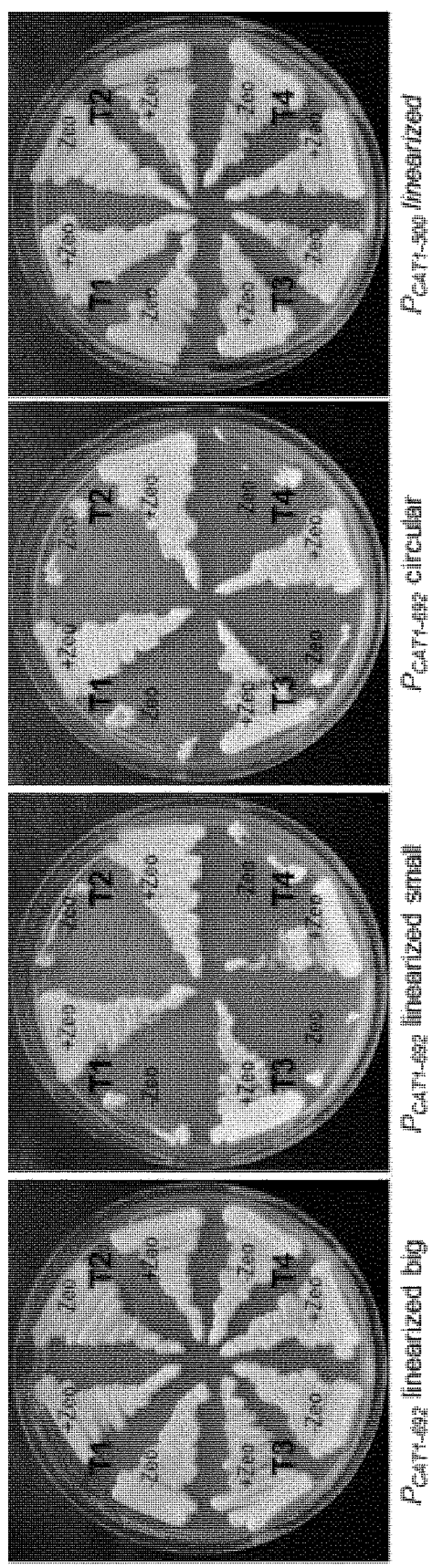

Since stamping from liquid culture involves a mixed population of cells, big and small colonies were streaked from linearized $P_{CAT1-692}$ and also colonies from a circular transformation on selective and non-selective agar plates. Subsequently single colonies were picked and streaked on selective media (FIG. 2C). As expected, big colonies maintained growth under any condition (identical to $P_{CAT1-500}$) whereas small colonies and circular plasmids lost the ability to grow on selective media when pre-cultivated under non selective conditions.

From these results it was concluded, that big colonies contain stably integrated cassettes in the genome, whereas small colonies bear episomally replicating plasmids, providing an explanation for stability issues observed previously. This effect is not specific for selection with Zeocin but occurred also with Geneticin and complementation gut1 knockout strain showing a deficiency in glycerol metabolization.

Notably, the empty vector and $P_{CAT1-500}$ are only showing tiny additional colonies (FIG. 2A). Even if the plates are incubated for a longer time these colonies do not increase in size and also do not grow if streaked again on selective media. Since transformation of circular forms of the empty vector and $P_{CAT1-500}$ are not showing any growth, we assume that the tiny colonies are not related to ARSs and caused by a different phenomenon.

Figure 3A:
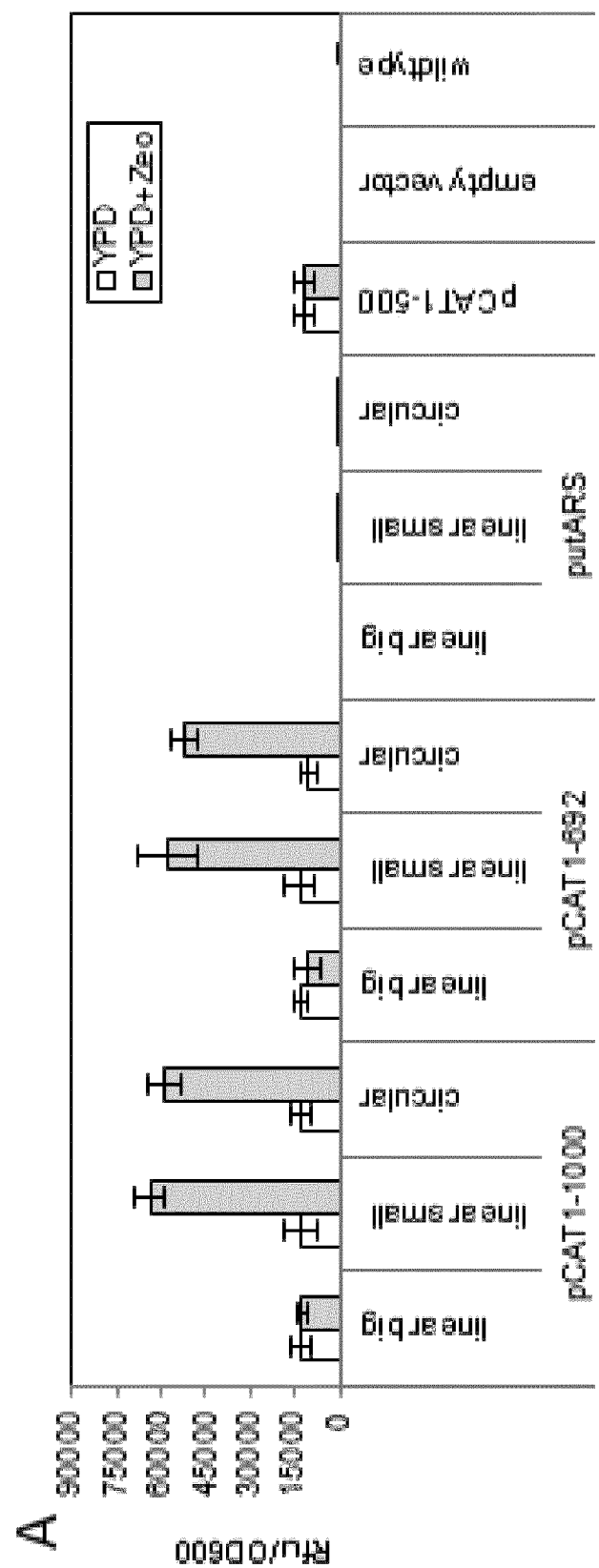
Figure 3B:
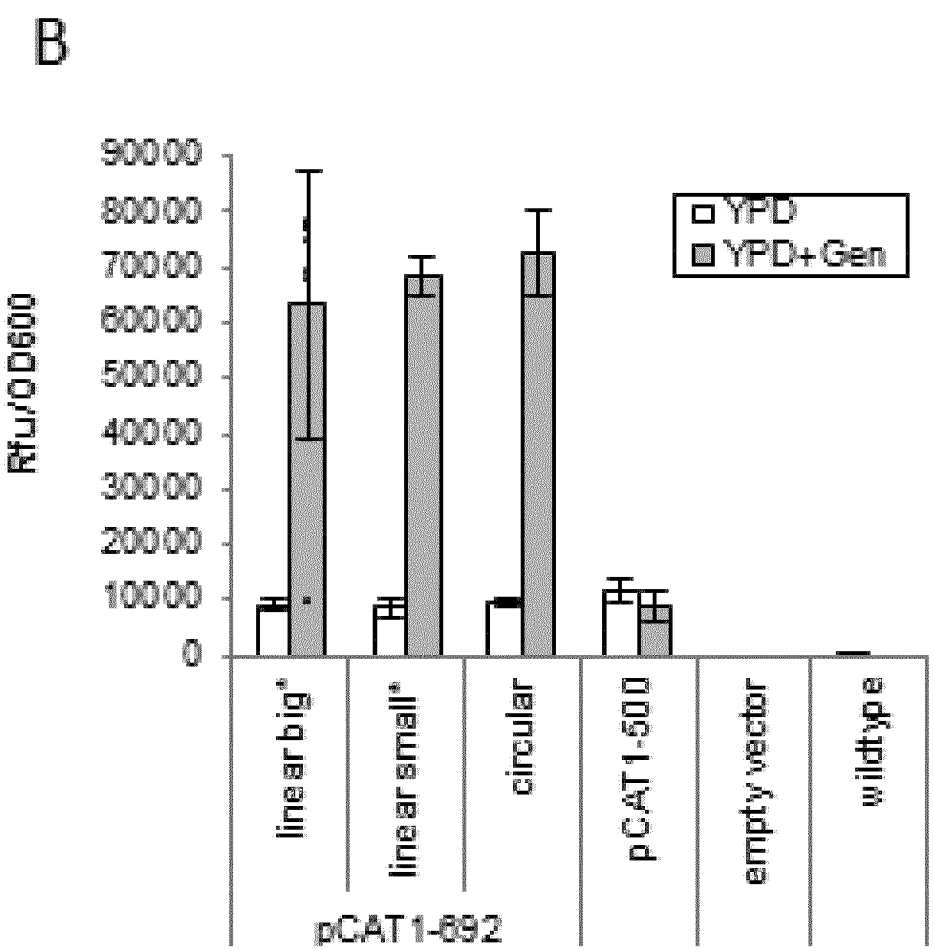
Figure 3C:
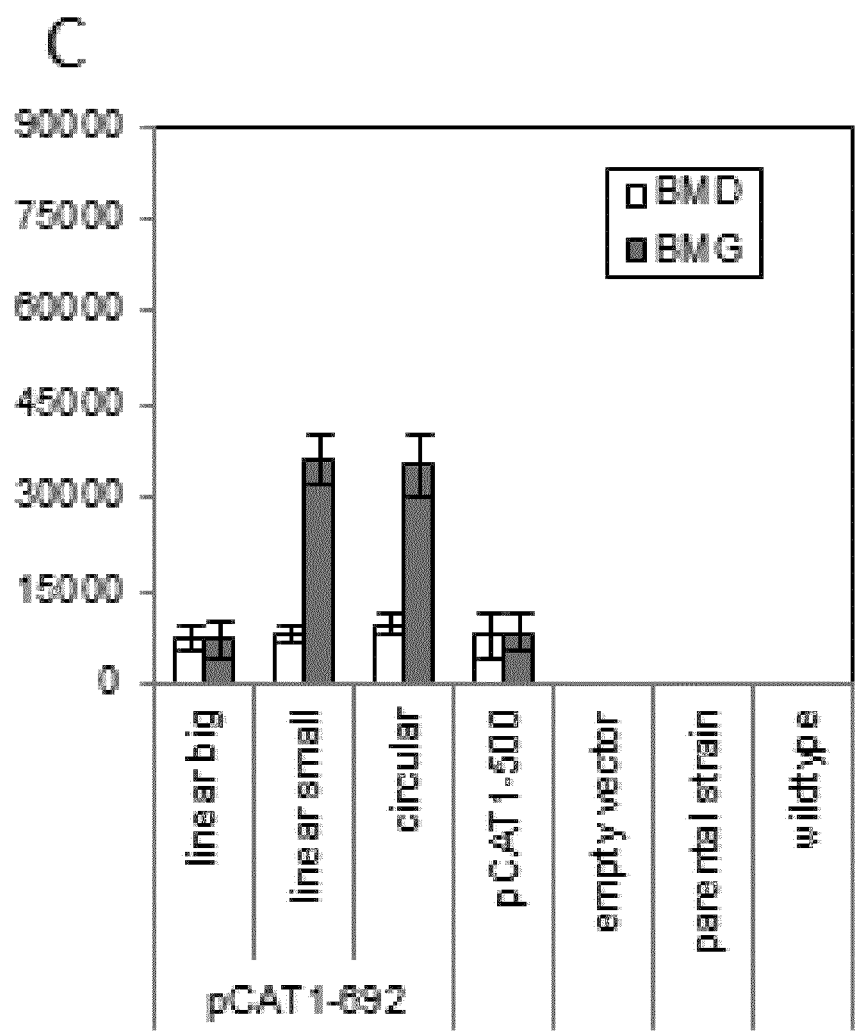
Figure 4A:
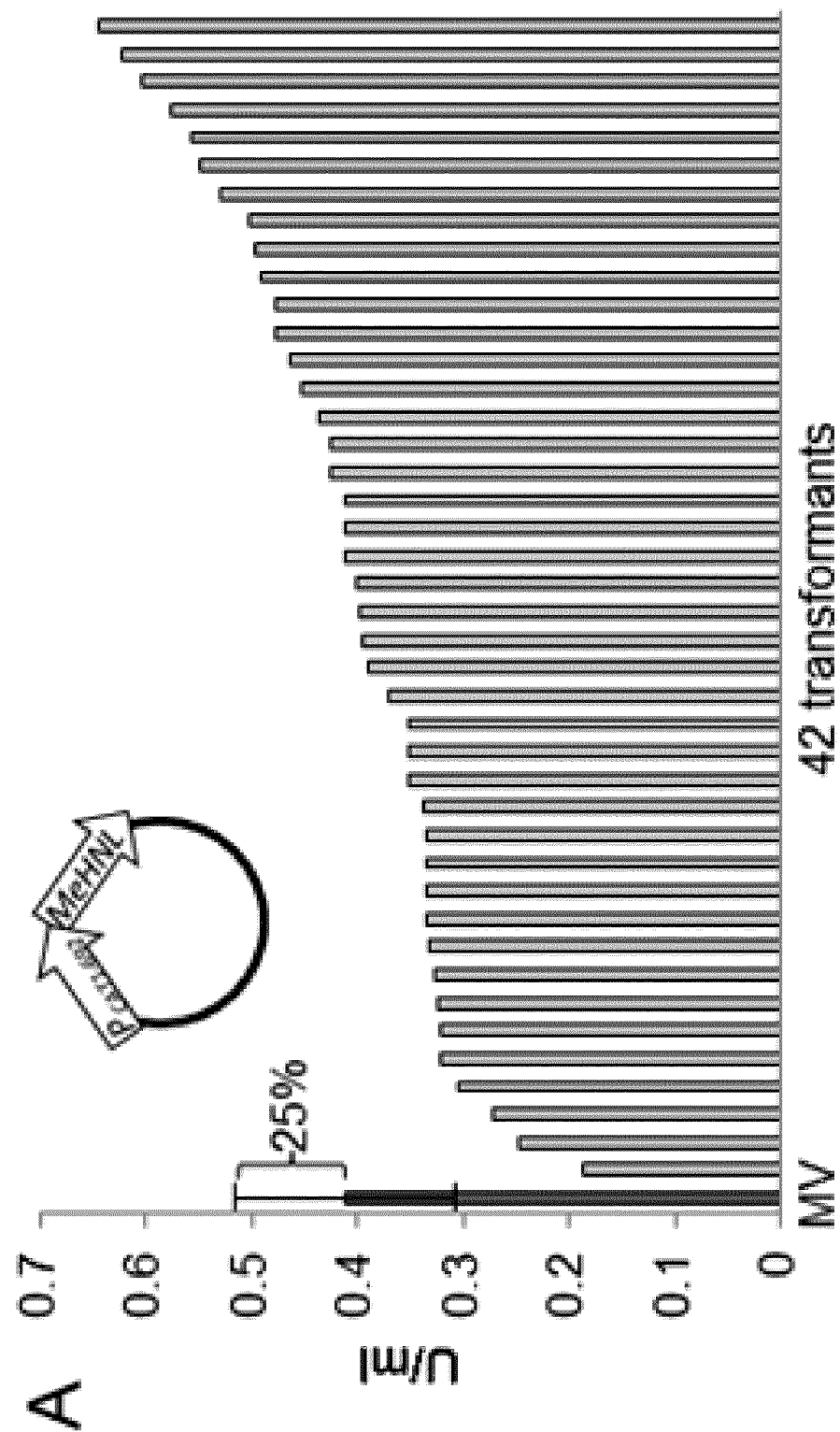
Figure 4B:
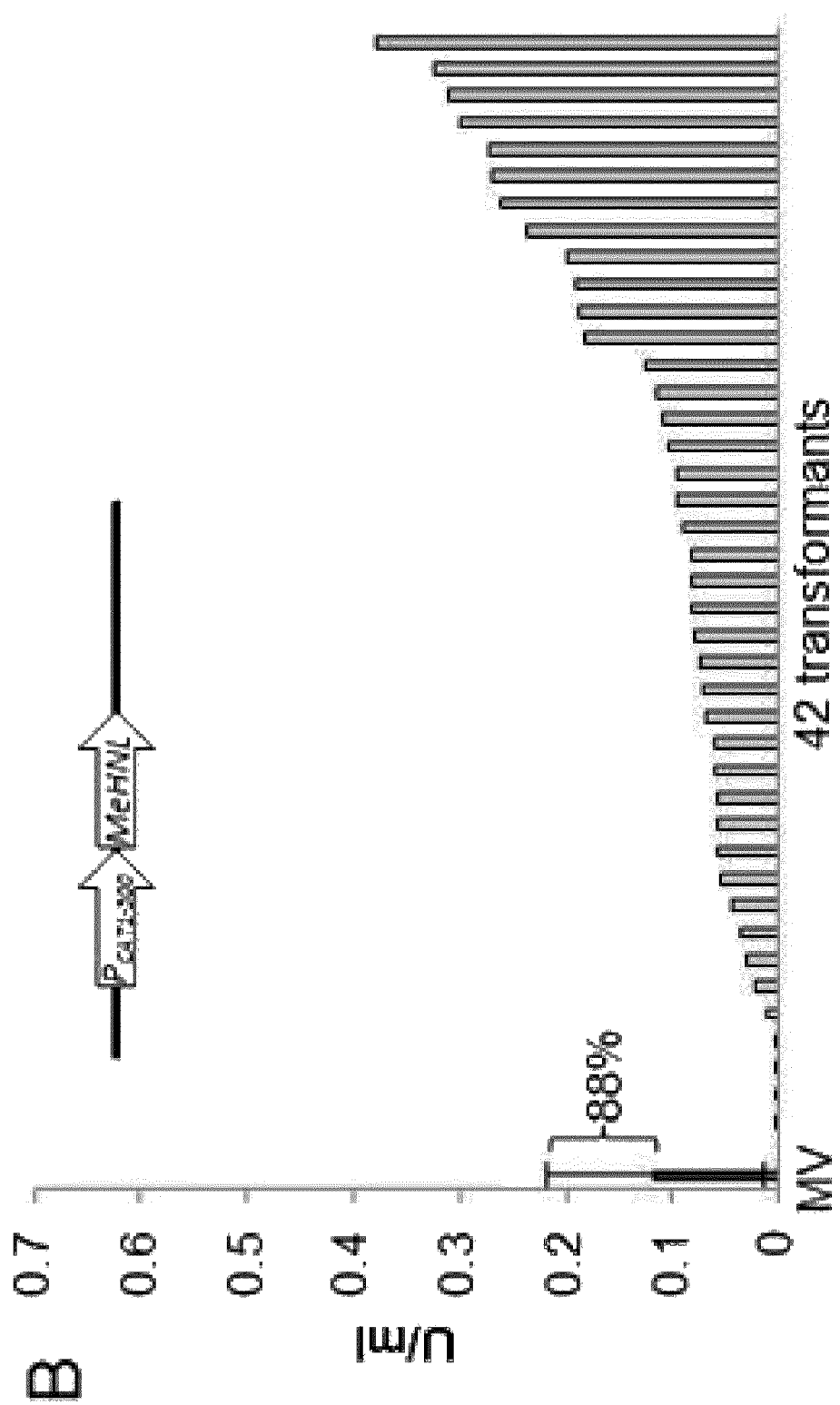
Figure 4C:
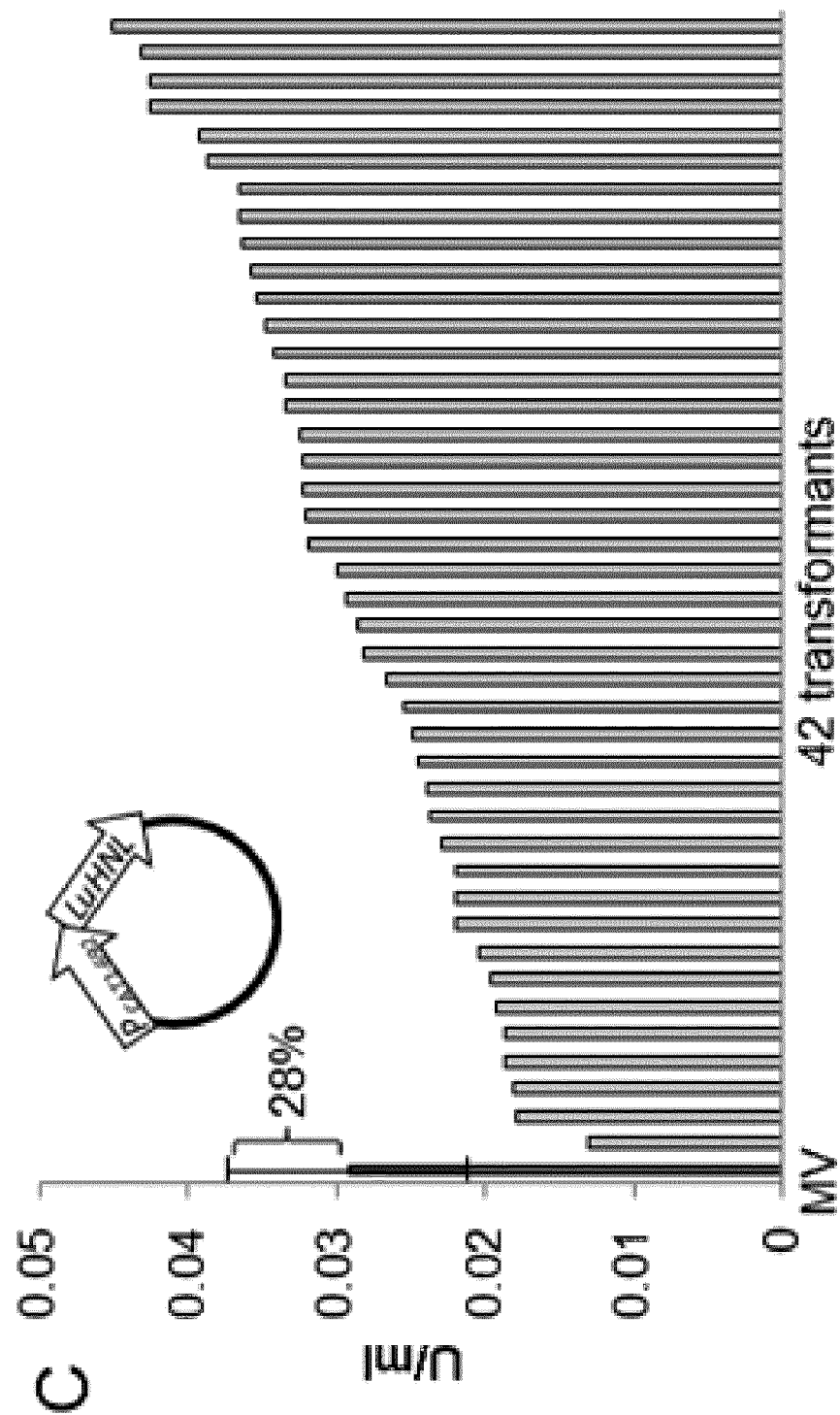
Figure 4D:
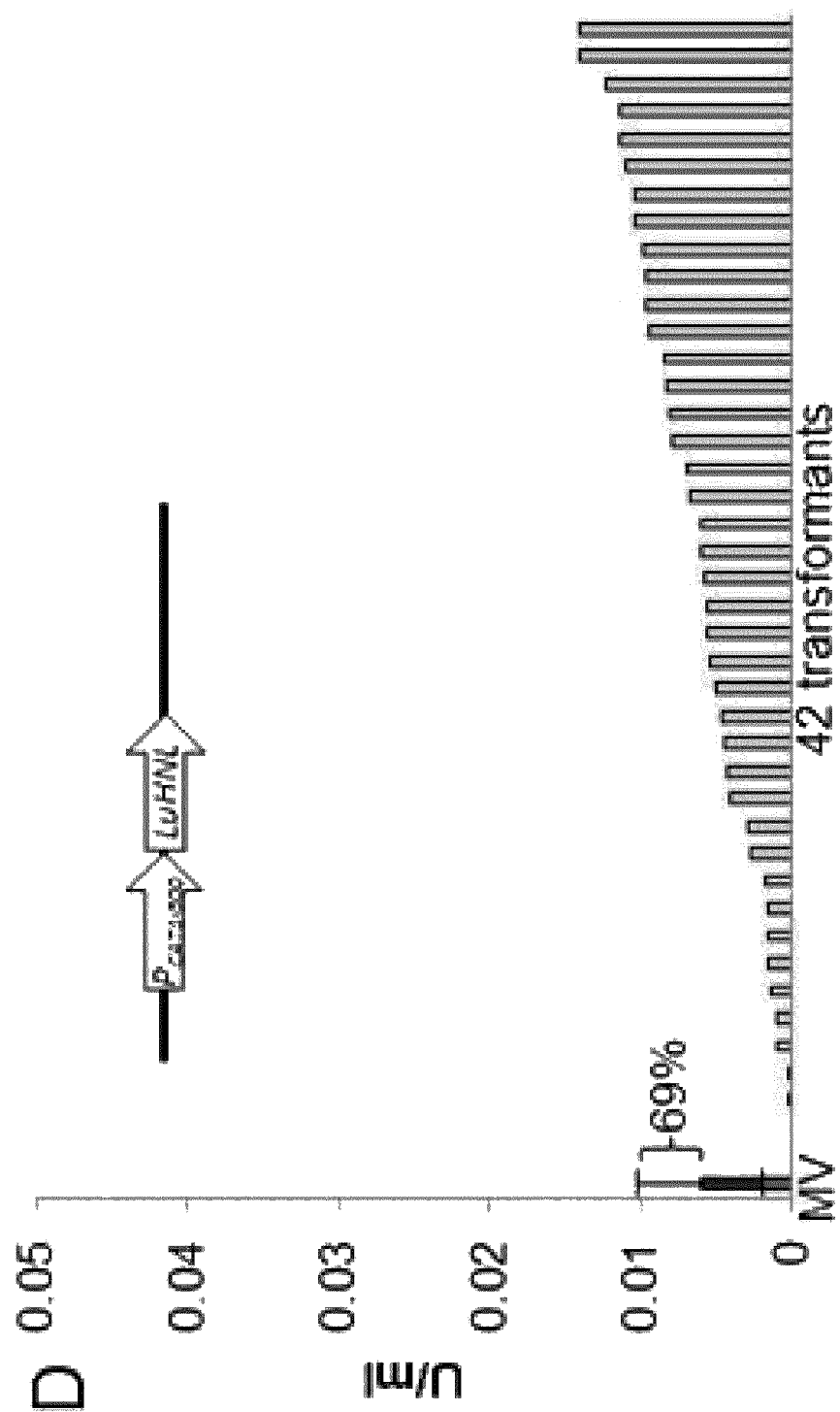

Example 3: The ARS of $P_{CAT1}$ Enables High Episomal Expression Under Selective Pressure Besides the stamping experiments of FIG. 2B, also the fluorescence of the eGFP reporter was measured from the different lengths and colony sizes of $P_{CAT1}$ (FIG. 3A). Surprisingly, small and big colonies showed similar reporter fluorescence when cultivated under non-selective conditions, suggesting that effect of the plasmid loss observed in (FIG. 2B,C) is not severely affecting reporter protein fluorescence upon growth in deep well plates in full media. However, strains bearing episomal plasmids (linearized small colonies, circular) showed on selective media a five-fold higher reporter protein fluorescence than under non-selective conditions or compared to genomic integration (any big colonies, $P_{CAT1-500}$) (FIG. 3A). This effect was even more pronounced with a different selection marker (Geneticin) leading to a more than seven-fold increase (FIG. 3B).

These results suggest that the episomally replicating plasmids under selective pressure are simple tools for increasing expression.

Despite increased yields, it would be in most cases economically unfeasible to maintain selective pressure in larger scale cultivations using Zeocin or Geneticin, two relatively expensive antibiotics. Therefore the ARS was combined with selection by glycerol utilization. Hereto, a glycerol kinase 1 (gut1) knock out strain unable to metabolize glycerol efficiently was used and transformed with complementation plasmids containing the wild-type GUT1 gene with its own promoter and terminator (Näätsaari et al. 2012) and $P_{CAT1-692}$ driving expression of the eGFP reporter gene. Since $P_{CAT1-692}$ and $P_{CAT1-1000}$ showed identical behavior in presence of Zeocin in the media, alternative selection markers were only tested with the shorter promoter variant $P_{CAT1-692}$. Similarly to Zeocin or Geneticin enhanced expression, also a more than 4.4-fold increased reporter protein fluorescence under selective conditions (glycerol as sole carbon source) was obtained (FIG. 3C), proving that also carbon source based selection is suitable to strongly increase expression from episomal plasmids.

Figure 6B:
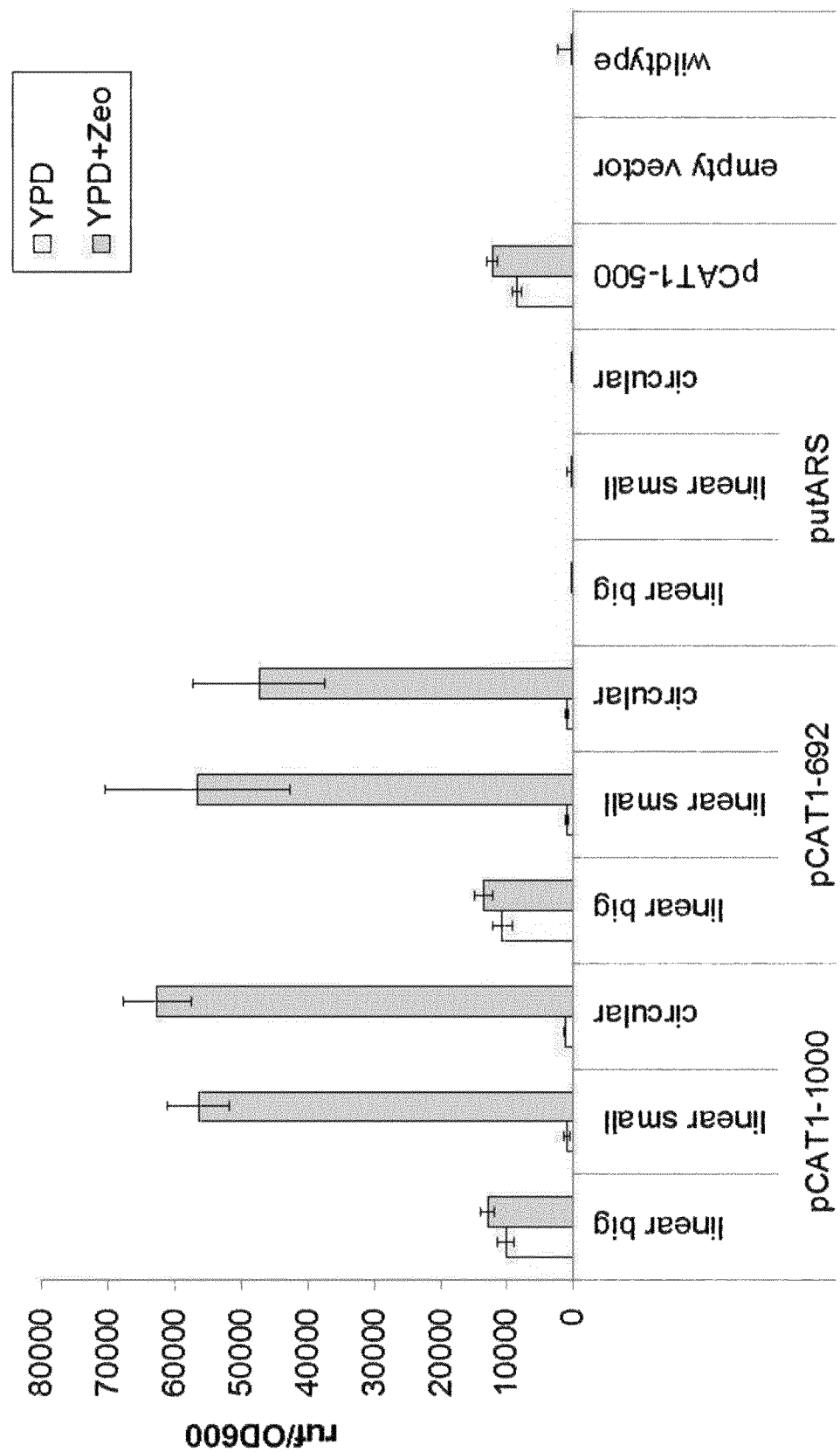

Instability issues were previously especially noted when re-cultivating $P_{CAT1}$ ARS containing plasmids from glycerol stocks. Therefore a glycerol stock of the cultivations shown in FIG. 2B and FIG. 3A was used to inoculate selective and non-selective media (FIG. 6). Plasmid loss determined by stamping assays on selective and non-selective media was even more severe than from direct inoculation (FIG. 6A versus FIG. 2B). Interestingly, in this case also the fluorescence of plasmid bearing constructs strongly decreased under non-selective conditions, suggesting almost complete plasmid loss (FIG. 6B versus FIG. 3A). These results imply that the ARS plasmids are more prone to loss under stress conditions such as freezing and re-cultivation.

Example 4: The Combination of $P_{CAT1}$ and its Endogenous ARS Provide a Screening System with Improved Transformation Rates, Increased Yields and Higher Landscape Uniformity Transformation efficiencies of the circular ARS plasmid were on average 108 fold higher than using linearized expression cassettes needed for genomic integration (FIG. 5). High transformation efficiencies are needed when performing protein engineering and screening large random libraries of variants. However, such screening systems must not add additional bias to the results. Differences between variants should solely arise from mutations in the gene of interest and not because of different copy numbers or integration events. The episomal $P_{CAT1}$ plasmid was tested for the expression of industrially relevant biocatalysts (hydroxynitrile lyases from *Manihot esculenta* (MeHNL) and *Linum usitatissimum* (LuHNL)). A larger number of transformants was screened to compare the uniformity of the expression landscape of episomal replication ($P_{CAT1-692}$) and genomic integration ($P_{CAT1-500}$) (FIG. 4) As for the eGFP reporter gene (FIG. 3), also MeHNL and LuHNL expressed from episomal plasmids under selective pressure showed increased expression compared to genomic integration (3.5 and 4.9 fold comparing the mean values of the whole landscapes). Therefore the beneficial effects of the easy to fold and maintain eGFP could also be reproduced for more complex enzymes. Due to higher transformation efficiencies, considerably lower amounts of the plasmid (10 ng) could be used to achieve similar numbers of transformants of linearized cassettes. In addition no restriction endonuclease digestion and purification/desalting steps are needed for the ARS plasmids shortening experimental time and reducing costs.

The episomal $P_{CAT1}$ plasmid resulted also in up to 3.5-fold more uniform expression than genomic integration (comparing the standard deviations in percent). For MeHNL, the transformant with the highest activity from genomic integration reached similar activity as average ARS transformants. For LuHNL the best genomically integrated transformant reaches only activity comparable to the worst episomal transformant. Some genomically integrated transformants did not show any detectable activity, while all episomal transformants were active. Clonal variability of genomic integration is known for *P. pastoris* (Gregg et al. 2009) and may be attributable to differences in copy number or the locus of genomic integration. *P. pastoris* has lower rates of homologous recombination than *S. cerevisiae* and linearized cassettes integrate at rates between less than 0.1% up to 30% (Näätsaari et al. 2012). Relatively high amounts of linearized DNA (3.5 μg) were used to obtain also multi copy strains, which may lead to a higher variability of the landscape. To this end also lower amounts of plasmid typically resulting only in single copy integration were transformed, resulting in improved landscape uniformities (FIG. 8). The use of larger amounts of DNA for transformation may be preferable in order to obtain libraries with high numbers of individual transformants. Several transformations have to be done and transformants need to be pooled if low amounts of DNA are employed.

Example 5: High Expression Levels can be Obtained with the New ARS and Truncated Variants Thereof The different ARSs (Accession: M11199, SEQ ID: NO3, 5, 6, 7, 8, 9, 10, 11 and 12) were cloned into pPpT4mutZeoMlyI-intArg4-EGFP-pCAT1-500, which also served as integrated control, between the transcription terminator of the selection marker and the *E. coli* origin. The ARSs were PCR amplified using the primers listed in Table 2, and cloned into the PstI linearized vector with Gibson assembly (Gibson et al. 2009). AOD-F6 was amplified using the primers AODTT-PstI-CbAOD1ARS-F3-Gib and pUC Ori-KpnI-CbAOD1ARS-F5-Gib. AOD-Full was amplified using the primers AODTT-PstI-CbAOD1ARS-F1-Gib and pUC Ori-KpnI-CbAOD1ARS-F5-Gib. Afterwards the constructs were sequence verified.

After transformation of the circular plasmids into *P. pastoris* BG10 seven individual transformants of each construct were picked for screening. The same transformants were cultivated in YPD and YPD with 50 mg/L Zeocin. After the first screening the same transformants were also used for the screening with different Zeocin concentrations and the CAT1-692 promoter (plasmid as described in above) was also included. For the integrated control one representative clone, identified by re-screening, was used in biological septuplicates.

TABLE 2

Primers used in this study

| Name | | Sequence |
|---|---|---|
| PARS1 | AODTT-PstI-ARS1-Gib | GAAGATTGGGGAAACTTGGATCTGATTACCTTAGCTGCAGTCG AGATAAGCTGGGGGAACATTCG SEQ ID NO: 22 |
| | pUC Ori-KpnI-ARS1-Gib | CTACGGGGTCTGACGCTCAGTGGTACCTCGACAATTAATATTT ACTTATTTTGGTCAACCCCAAATAG SEQ ID NO: 23 |

TABLE 2-continued

Primers used in this study

| Name | Sequence | |
|---|---|---|
| CAT1-ARS | AODTT-PstI-pCAT1ARS-Gib | GAAGATTGGGGAAACTTGGATCTGATTACCTTAGCTGCAGAGT GTGTAATCATATATATAATAAATGAGGAATAATAATTGAATAGAG ATTTAAC SEQ ID NO: 24 |
| | pUC Ori-KpnI-pCAT1ARS-Gib | CTACGGGGTCTGACGCTCAGTGGTACCCGTAGAAAAAAATGTG GTGAAACAGTTTCATAAGAG SEQ ID NO: 25 |
| AOD-F1 | AODTT-PstI-CbAOD1ARS-F1-Gib | GAAGATTGGGGAAACTTGGATCTGATTACCTTAGCTGCAGGGA GTATACGTAAATATATAATTATATATAATCATATATATGAATACAA TGCAATG SEQ ID NO: 26 |
| | pUC Ori-KpnI-CbAID1ARS-F1-Gib | CTACGGGGTCTGACGCTCAGTGGTACCAAAATAAATTAAATAA GTTAAATAAAATTAAGTGAATAAAGTTTCAGAATTGTTATTAAG SEQ ID NO: 27 |
| AOD-F2 | AODTT-PstI-CbAOD1ARS-F2-Gib | GAAGATTGGGGAAACTTGGATCTGATTACCTTAGCTGCAGTAC CCCAGTTTTTCAGTACAATGCAGC SEQ ID NO: 28 |
| | pUC Ori-KpnI-CbAOD1ARS-F2-Gib | CTACGGGGTCTGACGCTCAGTGGTACCTGCGGAGTGGGGCGT G SEQ ID NO: 29 |
| AOD-F3 | AODTT-PstI-CbAOD1ARS-F3-Gib | GAAGATTGGGGAAACTTGGATCTGATTACCTTAGCTGCAGTAA ACATCCCCAGCAGTTTCCCCAG SEQ ID NO: 30 |
| | pUC Ori-KpnI-CbAOD1ARS-F3-Gib | CTACGGGGTCTGACGCTCAGTGGTACCATTTTAATTAAGCGAA TATAAATTAATATTATAATATGAATTTATTTATAGATAGTAAATAT AG SEQ ID NO: 31 |
| AOD-F4 | AODTT-PstI-CbAOD1ARS-F4-Gib | GAAGATTGGGGAAACTTGGATCTGATTACCTTAGCTGCAGGCT CTTTTCCATCATCATCATCATCATCATC SEQ ID NO: 32 |
| | pUC Ori-KpnI-CbAOD1ARS-F4-Gib | CTACGGGGTCTGACGCTCAGTGGTACCTGATGATACTTAATTT ACGTATATACATATATGAAAATAGAATAAAAAATGC SEQ ID NO: 33 |
| AOD-F5 | AODTT-PstI-CbAOD1ARS-F5-Gib | GAAGATTGGGGAAACTTGGATCTGATTACCTTAGCTGCAGCGC TGCTTACTGTACGTTTAAAATGTGG SEQ ID NO: 34 |
| | pUC Ori-KpnI-CbAOD1ARS-F5-Gib | CTACGGGGTCTGACGCTCAGTGGTACCTATTGAAAAATAATTTT GTTTTTTTTTTTTTGTTTTTTTAAAAGTTCGTTAAAATTC SEQ ID NO: 35 |

High expression levels can be obtained for the new ARSs and also truncated fragments thereof with applied selection pressure during cultivation and expression. Higher expression levels were obtained with increasing Zeocin concentrations (FIG. 22), while it remained the constant for the integrated control (CAT1-500). Especially at lower Zeocin concentrations the new ARSs showed higher expression than the previously known ARS1 sequence from *P. pastoris*.

Digital PCR experiments which were performed in order to quantify the cellular plasmid content for the individual ARS plasmids and for the same plasmids under different growth conditions confirmed a higher plasmid content for the CbARS based plasmid compare to the CAT1-ARS based plasmid and also for cells grown in presence of 300 mg/L Zeocin, compared to 50 mg/L.

Example 6: Analysis of Bifunctional Activity of ARS as ARS and Terminator of Transcription The best fragment from the *C. boidinii* PAOD1 (F1), PARS1, CAT1-ARS and the 692 bp long version of the PCAT1 as well as the promoter without the core promoter (SEQ ID NO:13; last 78 bp, beginning with the TATA box were deleted) were tested for their activity as transcription terminators. They were compared to the terminators for the selection marker, which are present in the pPpT4_S and pPpGUT1 vectors, and to the best in house terminators (heterologous and homologous).

Therefore a terminator reporter plasmid was built based on the pPpT4_S vector (Näätsaari et al. 2012) containing PAOX1 and an eGFP reporter gene (reported in Vogl et al. 2014). The AOX1* terminator present was replaced with a stuffer fragment. Therefore the vector was cut with NotI and BamHI. A THIS sequence from *S. cerevisiae* already previously used as stuffer (Vogl et al. 2015) was again used as stuffer fragment and amplified using primers eGFP-ScTHI5fwd-Gib and pILV5-ScTHI5rev-Gib. In this case, the stuffer is not flanked by BmrI sites (since PAOX1 contains a BmrI site), but a NotI and a BamHI site. The PCR fragment was cloned by Gibson assembly (Gibson et al. 2009) into the NotI and BamHI digested vector backbone and confirmed by sequencing using primers seqEGFP-520 . . . 5 43-fwd and seq-pILV5-150 . . . 173-rev.

The terminators and ARSs were PCR amplified using the primers listed in Table 3 and cloned by Gibson assembly or the NEBuilder HIFI DNA assembly Kit into the reporter vector. Alternatively the CAT1-ARS was ordered as double stranded DNA fragment and used directly (Table 3) for fusion with the vector. Seamless fusions of the terminators were achieved relying on restriction site removal by the recombination cloning procedure. The terminators were sequenced using primers seqEGFP-520 . . . 543-fwd and seq-pILV5-150 . . . 173-rev.

Example 7: Comparative Transformation Efficiency and Expression Yields for ARS Plasmids In order to test the transformation efficiency of our new episomal *P. pastoris* plasmid where the new heterologous *C. boidinii* ARS was used as a short DNA element with dual function (ARS and transcription terminator) transformation

TABLE 3

| Name | | Sequence |
|---|---|---|
| Stuffer | eGFP-ScTHI5fwd-Gib | acacatggcatggatgaattgtacaagtaagcggccgcGACCTCTGTTGCCTCTTT GTTG; SEQ ID NO: 36 |
| | pILV5-ScTHI5rev-Gib | caaaagaaacaagacattactgaaggatccTTAAGCTGGAAGAGCCAATCTC TTGAAAG; SEQ ID NO: 37 |
| sequencing primers | seqEGFP-520..543-fwd | Gatggttccgttcaactagcagac SEQ ID NO: 38 |
| | seq-pILV5-150..173-rev | caaaagaaacaagacattactgaaggatccGCTTATTTTCTGCCGAATTTTCA TGAAGTT; SEQ ID NO: 39 |
| SPG5 | ScSPG5T-Fwd | acacatggcatggatgaattgtacaagtaaCAAAGACGTTGTTTCATCGCGCT ATTAC; SEQ ID NO: 40 |
| | ScSPG5T-Rev | caaaagaaacaagacattactgaaggatccGCTTATTTTCTGCCGAATTTTCA TGAAGTT; SEQ ID NO: 41 |
| CAT1 ARS dsDNA fragment | CAT1-ARS | Gtttgtaactgctgctgggattacacatggcatggatgaattgtacaagtaaagtgtgtaatcatat atataataaatgaggaataataattgaatagagatttaacgagtcgaagtttctgaaatatacgc acagtttatatttatgattttgatatctaactacagtcttctccatatatttaactataaataataaagt atataactcttatgaaactgtttcaccacatttttttctacgggatccttcagtaatgtcttgtttcttt tgttgcagtg; SEQ ID NO: 42 |
| PARS1 | eGFP-ARS1-Gib | CACATGGCATGGATGAATTGTACAAGTAATCGAGATAAGCTGGG GGAACATTC; SEQ ID NO: 43 |
| | pILV5-BamHI-ARS1-Gib | CACTGCAACAAAAGAAACAAGACATTACTGAAGGATCCTCGACA ATTAATATTTACTTATTTTGGTCAACCCCAAATAG SEQ ID NO: 44 |
| AOD-TT | eGFP-AOD_TT-Gib | CACATGGCATGGATGAATTGTACAAGTAAAATTGACACCTTACGA TTATTTAGAGAGTATTTATTAG; SEQ ID NO: 45 |
| | pILV5-BamHI-AOD_TT-Gib | CACTGCAACAAAAGAAACAAGACATTACTGAAGGATCCTGCAGC TAAGGTAATCAGATCCAAG; SEQ ID NO: 46 |
| GUT1-TT | eGFP-GUT1_TT-Gib | CATGGCATGGATGAATTGTACAAGTAAGAAGAGCAGCTGTAATT ATATTATCATGTTAGG; SEQ ID NO: 47 |
| | pILV5-BamHI-GUT1_TT-Gib | CACTGCAACAAAAGAAACAAGACATTACTGAAGGATCCTGCCAG AGCTGTCACATACTTG; SEQ ID NO: 48 |
| AOD-F1 | eGFP-CbAOD1-F1-Gib | CACATGGCATGGATGAATTGTACAAGTAAGGAGTATACGTAAATA TATAATTATATATAATCATATATATGAATACAATGCAATG SEQ ID NO: 49 |
| | pILV5-BamHI-CbAOD1-F1-Gib | CACTGCAACAAAAGAAACAAGACATTACTGAAGGATCCAAAATAA ATTAAATAAGTTAAATAAAATTAAGTGAATAAAGTTTCAGAATTG SEQ ID NO: 50 |
| pCAT1-692 | eGFP-pCAT1-Gib | GCATGGATGAATTGTACAAGTAAAGTGTGTAATCATATATATAAT AAATGAGG; SEQ ID NO: 51 |
| | pILV5-BamHI-pCAT1-Gib | CAAAAGAAACAAGACATTACTGAAGGATCCTTTAATTGTAAGTCT TGACTAGAGC; SEQ ID NO: 52 |
| pCAT1no Core | pILV5-BamHI-pCAT1noCore-Gib | CAAAAGAAACAAGACATTACTGAAGGATCCTGATTTTGGCCTGAT GAG; SEQ ID NO: 53 |

For the *P. pastoris* transformation the constructs were SwaI linearized in order to facilitate genomic integration. After a first round of screening four representative clones from the middle of the expression landscape of more than 80 clones were chosen for a re-screening and re-streaked for single colonies. After the re-screening one representative clone for each construct was chosen and all constructs were cultivated together in one 96-well deep well plate in biological septuplicates.

rates with competent *P. pastoris* BG10 cells were determined in comparison to a plasmid employing the state of the art ARS1 sequence for autonomous replication.

The two ARSs were cloned into pPpT4_S containing the CAT1-500 promoter. The AOD terminator was removed by digesting the vector with SapI and KpnI and the two ARSs were cloned seamlessly behind the selection marker with recombination cloning (Gibson et al. 2009) after amplifying them with the primers from Table XY. These primers also add an *E. coli* transcription terminator.

The multiple cloning site was removed by digesting the vector with EcoRI and NotI and exchanged by a stuffer fragment (SEQ ID NO:14) containing a part of ScTHI5 as a stuffer DNA fragment to facilitate cloning and restriction sites enabling SapI cloning. The stuffer fragment was amplified using the primers listed in Table 4 and cloned with Gibson assembly. Afterwards eGFP was cloned into the vector using SapI cloning.

TABLE 4

Primers used in this study.

| Name | | Sequence |
|---|---|---|
| SapI cloning stuffer | pCAT1-SapCloning-ScTHI5-Gib | CATAACACTTGCTCTAGTCAAGACTTACAATTAAAATGAGAAGAG CGAATTCGGCGCGCCGGTAAGATCCAAATCGATGAATTGACCAA G SEQ ID NO: 54 |
| | AOX1_TT-SapCloning-ScTHI5-Gib | GCAAATGGCATTCTGACATCCTCTTGAGCGGCCGCTTATGAAGA GCTGTTCAATTGAGGCTTGAAGTCGATG SEQ ID NO: 55 |
| eGFP SapI cloning | SapI-eGFP fwd | TACACGTACTTAGTCGCTGAAGCTCTTCTATGGCTAGCAAAGGA GAAGAACTTTTCAC SEQ ID NO: 56 |
| | eGFP-SapI rev | AGGTACGAACTCGATTGACGGCTCTTCTTTACTTGTACAATTCAT CCATGCCATGTG SEQ ID NO: 57 |
| PARS1 | ZeoMutSapI-PARS1-GIB | GCTGGTAACTGCGTGCATTTCGTCGCAGAGGAACAGGACTAATC GAGATAAGCTGGGGGAACATTCG SEQ ID NO: 58 |
| | KpnI-T4 backbone-PARS1-GIB | CTACGGGGTCTGACGCTCAGTGGTACCTAAAAAAAATCCTTAGC TTTCGCTAAGGATTCGACAATTAATATTTACTTATTTTGGTCAACC CCAAATAG SEQ ID NO: 59 |
| CbARS | ZeoMutSapI-CbAOD1-F1-GIB | GCTGGTAACTGCGTGCATTTCGTCGCAGAGGAACAGGACTAAG GAGTATACGTAAATATATAATTATATATAATCATATATATGAATAC AATGCAATG SEQ ID NO: 60 |
| | KpnI-T4 backbone-CbAOD1-F1-GIB | CTACGGGGTCTGACGCTCAGTGGTACCTAAAAAAAATCCTTAGC TTTCGCTAAGGATAAAATAAATTAAATAAGTTAAATAAAATTAAGT GAATAAAGTTTCAGAATTG SEQ ID NO: 61 |

For testing the transformation efficiency the plasmids containing PARS1 and CbARS as well as the pPpT4-S (linearized and circular) were diluted to 100 ng/μl and transformed into electro-competent *P. pastoris* BG10 cells. 1 μl was transformed and 100 μl (for the pPpT4-S plasmid also 1000 μl) of different dilutions were plated onto YPD-Zeo plates.

Table 5 shows the high transformation rate in *P. pastoris* BG10 (9.5*10^5 cfu/μg). Results are shown for final ARS vectors containing the ARSs also as terminator (TT) for the selection marker cassette and eGFP as a reporter gene downstream of the CAT1 promoter.

TABLE 5

| | Volume plated | Dilution factor | Colonies counted | CFU/μg | Mean | SD |
|---|---|---|---|---|---|---|
| PARS1 | 100 | 1 | n.c. | | 461500 | 170578 |
| | 100 | 10 | 474 | 474000 | | |
| | 100 | 100 | 54 | 540000 | | |
| | 100 | 1 | n.c. | | | |

TABLE 5-continued

| | Volume plated | Dilution factor | Colonies counted | CFU/μg | Mean | SD |
|---|---|---|---|---|---|---|
| | 100 | 10 | 612 | 612000 | | |
| | 100 | 100 | 22 | 220000 | | |
| CbARS | 100 | 1 | n.c. | | 950000 | 443095 |
| | 100 | 10 | 640 | 640000 | | |
| | 100 | 100 | 57 | 570000 | | |

TABLE 5-continued

| | Volume plated | Dilution factor | Colonies counted | CFU/μg | Mean | SD |
|---|---|---|---|---|---|---|
| | 100 | 1 | n.c. | | | |
| | 100 | 10 | 1060 | 1060000 | | |
| | 100 | 100 | 153 | 1530000 | | |
| pPpT4-S SmiI | 100 | 1 | 84 | 8400 | 7375 | 1293 |
| | 1000 | 1 | 844 | 8440 | | |
| | 100 | 1 | 69 | 6900 | | |
| | 1000 | 1 | 576 | 5760 | | |

The transformation efficiency was highest for the heterologous *C. boidinii* ARS CbARS. The high transformation efficiency even allows re-transformation of *Pichia* after simple plasmid isolation with Zymolyase and a miniprep kit. The plasmid isolation from *Pichia* was performed from a 5 ml ONC grown in YPD with 300 mg/L Zeocin in order to get a higher plasmid copy number. The ONC was harvested and the pellet re-suspended in 1 ml yeast lysis buffer (1 M Sorbitol, 100 mM EDTA, 14 mM β-mercaptoethanol. Afterwards 100 μl of a Zymolyase stock (1000 U/ml) were added and the reaction mix was incubated at 30° C. for 1 hour. The spheroblasts were then harvested by centrifugation for 5 min at maximal speed, the supernatant was removed and the plasmids isolated using the GeneJET Plasmid Miniprep Kit. The DNA was eluted with 20 µl ddH$_2$O and the whole miniprep was used for the *Pichia* transformation and eGFP measurements of cultures of 84 individual transformants proved the presence of the correct plasmid.

Transformants from direct transformation with plasmid DNA isolated from *Pichia pastoris* without prior amplification and isolation from *E. coli* are shown in FIG. 24.

eGFP expression of individual transformants under the control of PCAT1 promoter, using episomal plasmids with different sequence parts (A,B with ARS1, C&D with CbARS) used as bifunctional ARS and terminator sequences for the selection marker (with and without selective pressure) and autonomous plasmid replication are shown in FIG. 25.

Example 8: Reliability of CbARS Plasmid Based Expression Strains

In order to test the reliability of protein expression employing the new episomal plasmids, the frequently used strong constitutive GAP promoter (P$_{GAP}$) was used to drive eGFP expression in combination with the new heterologous CbARS part. Very uniform and high expression levels were obtained with the Zeo ARS plasmid containing P$_{GAP}$ and CbARS.

P$_{GAP}$ was cloned into the SapI cloning vector described in Experiment 7 by digesting the vector and the PCR product of the promoter (amplified with the primers pUCori-SwaI-pGAP and pGAP rev) with NotI and EcoRI followed by ligation. Afterwards eGFP was cloned into the vector using SapI cloning.

and without dephosphorylation) in the WT strain whereas the number of transformants in the KU70 deletion strain was significantly lower. Therefore we concluded that vector relegation to circular episomal plasmids is higher in the WT strain compared to the KU70 deletion strain.

Example 10: Homologous Recombination (HR) Cloning in *Pichia pastoris*

To evaluate the possibility to use CbARS plasmids for HR cloning in *Pichia* a constitutive expression vector containing P$_{GAP}$ and a zeocin resistance gene for selection was used.

The reporter protein (eGFP) was amplified with different lengths of homologous regions to the vector backbone ranging from 50 to 500 bp.

Fifty ng of vector backbone and 3-fold molar excess of insert were used for co-transformation of a *P. pastoris* dKU70 strain BSY11dKU70 (FIG. 28).

A strain with a KU70 deletion was used to minimize integration of the linear DNA fragments, because non-homologous end-joining, which is quite common in *Pichia* and would lead to ectopic integration of the fragments, is impaired in this strain (6). Integration of the vector backbone into the genome would also lead to colonies with zeocin resistance without showing expression or with low expression because the GOI could also integrate somewhere into the genome.

As shown in FIG. 28, HR cloning worked with short overhangs of just 50 bp, but showed increased transformation efficiency with longer overlapping regions. Homologous regions of 250 bp seemed to be ideal in this set-up, since increase to 500 bp did not show any improvement.

TABLE 6

Primers used in this study

| Name | Sequence |
|---|---|
| pUCori-SwaI-pGAP | CCTTTTGCTCACATGTATTTAAATTTTTTGTAGAAATGTCTTGGTGTCCTC<br>SEQ ID NO: 62 |
| pGAP rev | GATTTGGATCTTACCGGCGCGCCGAATTCGCTCTTCTCATTGTGTTTTGATAGTT<br>GTTCAATTGATTG<br>SEQ ID NO: 63 |

Ten ng of circular plasmid DNA were transformed into *P. pastoris* BG10 and the GAP promoter driven eGFP expression of 21 individual transformants was measured after 60 h of cultivation in a 96-well deep well plate using YPD with 50 mg/L Zeocin (see FIG. 26).

Example 9: Strain Comparison for Transformation of *P. pastoris* with Linearized and Circular Plasmid DNA In order to evaluate the transformation efficiency of different *P. pastoris* platform strains a wildtype like strain of *Komagataella phaffii* with a disrupted AOX1 gene (WT) (strain described in Näätsaari et al. 2012) and a *K. phaffii* strain with additionally disrupted KU70 gene (BSY11dKU70) were used for transformation with linearized, both with and without dephosphorylation (cut in non homologous region for ectopic integration) and circular plasmid DNA containing the CAT1 promoter with ARS element (PCAT1_692) or without (PCAT1_500).

As shown in FIG. 27, high numbers of transformants were seen with the ARS containing linearized plasmids (both with With this set-up approximately 10$^\wedge$5 CFU/µg were reached. Just minimal background containing religated vector backbone was observed.

To evaluate the possible integration of the expression vectors, the transformants were cultivated and compared in Deep Well Plates (DWPs) with and without selection pressure (i.e. YPD with 50 µg/ml zeocin (YPD-Zeo) and YPD without zeocin). Transformants, which carry the expression plasmid episomally should show elevated expression levels under selection pressure due to multicopy effect and because the plasmids get lost without selection pressure. Transformants, which have integrated the expression cassette, should behave similar under both conditions.

100% of the tested colonies (n=168, 42 per overlap length) showed vastly higher eGFP expression levels under selective conditions. Transformants from the background control (i.e. just vector backbone used for transformation) did not show any fluorescence. Therefore, we concluded that the transformants contained the episomal expression plasmid.

Uptake of multiple plasmids per cell when circular ARS plasmids are used for transformation in high amounts was already observed before. Since this might be an unwanted effect for generating and screening libraries, transformation of high amounts of DNA and two different reporter proteins (eGFP and sTomato) with 250 bp homologous regions to the vector was tested (FIG. 29).

Different amounts of vector backbone and twice the amount of insert were used for transformation.

Even with three µg of DNA (1 µg vector backbone and 2 µg insert) just below 30% of the transformants showed expression of both reporter proteins. With this high amount of DNA up to $5*10^{\wedge}6$ CFU/µg vector backbone were reached (FIG. 29).

Transformants, which carried both plasmids were re-streaked and single colonies used for another round of cultivation. In the second round presence of both reporter proteins for any of the colonies was not detected.

This indicates that after several generations there is just one variant present in single cells.

Experimental Details:

HR cloning experiments with eGFP and sTomato were performed with the vector described in SEQ ID NO:72. The vector was linearized with SapI and gel purified for HR cloning. The ARS identified as SEQ ID NO:6 was used.

eGFP and sTomato with different lengths of homologous regions to the vector were amplified with primers (Table 7) binding in the promoter and terminator region of this vector backbone. In order to generate templates for the reporter proteins, eGFP and sTomato were cloned seamlessly into the SapI linearized backbone using SapI cloning.

The cut backbone and the amplified insert with overlapping regions to the vector backbone were used for co-transformation. 50 ng of the backbone and a 3:1 molar ratio (insert:vector) was used for the first test.

For the subsequent evaluation if more than one variant is taken up by one cell, the two inserts (i.e. eGPF and sTomato with 250 bp overlapping region) were mixed in equal amounts and the mixture was used for co-transformation with the cut backbone. Higher amounts of DNA with up to 1 µg of backbone and 2 µg of insert were used for the transformation.

All PCR products were gel purified prior transformation.

TABLE 7

Primers used for HR cloning with eGFP and sTomato

| Primer name | Sequence |
|---|---|
| HR50fw | TTTAATTTATTTGTCCCTATTTCAATC<br>SEQ ID No: 64 |
| HR50rv | AAAATGAAGCCTGCATCTCTC<br>SEQ ID No: 65 |
| HR100fw | AGGCGAACACCTTTCCC<br>SEQ ID No: 66 |
| HR100rv | AATGACAAAAAAATCCTATACTATATAGGTTAC<br>SEQ ID No: 67 |
| HR250fw | TGTTCTTCCCAGCATTACG<br>SEQ ID No: 68 |
| HR250rv | AGGTCTCACTTAATCTTCTGTACTCTG<br>SEQ ID No: 69 |
| HR500fw | ACATGTATTTAAATTTTTTGTAGAAATGTC<br>SEQ ID No: 70 |
| HR500rv | CGGTACATTGTTGCCATATG<br>SEQ ID No: 71 |

Example 11: Generation of Antibody Library

Following the tests with eGFP, the feasibility of the system for an IgG antibody (Herceptin, trastuzumab, Roche) expression vectors was evaluated. Different molar ratios of up to 5:1 (insert:vector) and longer homologous regions were used, but the amount of DNA was still kept low with 50 ng vector backbone (FIG. 30). The strain BSY11dKU70 was used for HR cloning as described above.

The use of more insert increased the transformation efficiency, and the results from first pre-tests regarding overlap length were confirmed, since increasing length of above 250 bp did not improve efficiency anymore and for very long homologous regions of 1000 bp the efficiency even decreased (FIG. 30).

In general, different sizes of colonies were observed (data not shown) after transformation and therefore big and small colonies for each length of overlapping regions were chosen for the cultivation (FIG. 31).

The presence as episomal vector was also tested by isolating the plasmids from the *Pichia* colonies, transforming *E. coli* and subsequent restriction analysis and sequencing (data not shown). All of the 24 tested clones contained the correct plasmid and just two of them harbored a single point mutation, most probably due to PCR errors, because the mutations were not in the overlapping regions.

Correct integration of the antibody expression cassette was checked by isolating the plasmid from 24 transformants followed by restriction analysis to check the presence of the insert and sequencing the regions of recombination. All of the vectors tested were positive, just two of them contained a single point mutation, which was not located in the overlapping regions and therefore most probable due to PCR errors when amplifying the backbone and the insert (data not shown).

With this knowledge the HR cloning system was scaled-up in a way that it could be used in final applications for antibody library generation and screening, employing the variable region of the antibody light chain (LC) with 250 bp overlaps as insert and the rest of the expression vector containing the other antibody genes, such as variable region of the heavy chain, constant regions. Since large libraries are needed for discovery of antibody variants/mutant CDR binding regions/mutant VH or VL sequences, 1 µg of vector backbone and 2 µg of insert were used for transformation. With this system and the frozen competent cells of Biogrammatics transformation efficiencies of $3.5*10^{\wedge}6$ CFU/µg vector and just approximately every $170^{th}$ transformant containing re-ligated vector were routinely reached repeatedly on several occasions.

This set-up also showed that it is not probable that the transformation efficiency decreases if a larger vector backbone is used, since in the pre-tests always small vector backbones were used, but in the final application the efficiency was even higher Since large libraries are needed for antibody discovery, 1 µg of vector backbone and 2 µg of insert were used for transformation. With this system and the frozen competent cells of Biogrammatics transformation efficiencies of $3.5*10^{\wedge}6$ CFU/µg vector and just approximately every $170^{th}$ transformant containing re-ligated vector were routinely reached repeatedly on several occasions.

Experimental Details:

Initial HR cloning experiments for the antibody constructs were performed by amplifying (SEQ ID NO:85 as a template and primers shown in Table 8) the whole CDSs of the IgG, including also a bidirectional promoter and signal sequences, with different lengths of overhangs to the vector. The vector backbone was also PCR amplified using the primers listed in Table 8 and the vector described in SEQ ID NO:85 as a template. Fifty ng of backbone and different molar ratios (1:1, 3:1 and 5:1) of insert:vector backbone were used for transformation. Overlapping regions of 250 to 1000 bp were tried. As already seen for eGFP as reporter protein, an increase above 250 bp did not further improve the transformation efficiency, but it was significantly higher when more insert was used.

With the knowledge, that high amounts of insert improve the efficiency we tried to make the system feasible for the final application (i.e. generation of antibody libraries) by using high amounts of DNA and exchanging just the variable region of the IgG's light chain.

This final proof of principle was carried out by amplifying the variable region of the light chain (with appropriate 250 bp long overhangs to the vector) and the vector backbone using the primers listed in Table 9 and the vector described in SEQ ID NO:86 as a template.

One µg of backbone and 2 µg of insert were used for co-transformation of P. pastoris BSY11dKU70. With this set-up transformation efficiencies of >3*10^6 CFU/µg were reached routinely (FIG. 32).

All PCR products were gel purified prior transformation.

TABLE 8

Primers used for HR cloning with whole IgG CDS including signal sequences and promoters as insert

| Primer name | Sequence |
|---|---|
| Her-HR250fw | GACCCTTGTGACTGACACTTTG SEQ ID No: 73 |
| Her-HR250rv | AGGTCTCACTTAATCTTCTGTACTCTGAAG SEQ ID No: 74 |
| Her-HR500fw | TCGATTTTTGTGATGCTCGTC SEQ ID No: 75 |
| Her-HR500rv | CGGTACATTGTTGCCATATGC SEQ ID No: 76 |
| Her-HR1000fw | TACCAGCGGTGGTTTGTTTG SEQ ID No: 77 |
| Her-HR1000rv | GCAAAGTCGTCCTCTACGAAG SEQ ID No: 78 |
| Her-Backbone-fw | TCAAGAGGATGTCAGAATGC SEQ ID No: 79 |
| Her-Backbone-rv | ACGGGAAGTCTTTACAGTTTTAGTTAG SEQ ID No: 80 |

TABLE 9

Primers used for HR cloning with the variable region of the IgG light chain as insert

| Primer name | Sequence |
|---|---|
| HR-LC-vec-fw | AGAACTGTTGCAGCTCCTTC SEQ ID No: 81 |
| HR-LC-vec-rv | AACACGGCTACCACCACCTC SEQ ID No: 82 |
| V-LC250-fw | TGCCCCCGTTAATACGACTAC SEQ ID No: 83 |
| V-LC250-rv | CTTTGTGTTTTTCATAGTCGGCTTTG SEQ ID No: 84 |

REFERENCES

Ahmad, M. et al., Appl Microbiol Biotechnol. 2014 June; 98(12):5301-1
Arenhart, S. et al., Brazilian J Microbiol 2016; 2-8
Astola et al., Gen. Comp. Endocrinol. 2003 134:57-61
Camattari, A et al. Microb Cell Fact 2016, 15:139
Chen, S. et al., Nucleic Acids Research 1996, 24(15), 2885-93.
Gregg, J. M. et al., Methods in Enzymology, 2009; 463(09), 169-89
Curran, K A. et al., Metab Eng 2013; 19C:88-97.
Gasser, B. et al., Future Microbiol. 2013 February; 8(2): 191-208
Gibson, D. G. et al., Nat Methods, 2009; 6(5), 343-5.
Hartner, F. S. et al., Nucleic Acids Res. 2008 July; 36(12), e76.
Hwang et al., Biochim. Biophys. Acta 2003 1625:11-18.
Joska, T. M. et al., J Microbiol Methods 2014; 100(1):46-51
Kim et al., Gene 2000 252:173-181;
Küberl, A. et al., J Biotechnol. 2011 Jul. 20; 154(4):312-20
Lee, C C et al., Plasmid 2001, vol. 54 (1), p. 80-85
Liachko, I. et al., PLoS Genet. 2010 May 13; 6(5):e1000946
Liachko, I., and Dunham, M. J. FEMS Yeast Res. 2014 March; 14(2):364-7
Liachko, I. et al., Genome Res. 2013 April; 23(4):698-704
Liachko, I. et al., PLoS Genet. 2014 Mar. 6; 10(3):e1004169
Lin-Cereghino, J. et al., Biotechniques. 2005 January; 38(1): 44-48.
Näätsaari, L. et al., PLoS One. 2012; 7(6):e39720
Oldenburg, K. R. et al., Nucleic Acids Res. 1997; 25(2): 451-2
Orr-Weaver, T. L. et al., Proc Natl Acad Sci USA. 1981 October; 78(10): 6354-6358
Peng, C. et al., Front Microbiol. 2015 Feb. 19; 6:117
Ruth, C et al. Chembiochem 2010, vol. 11 (6), p. 761-765
Sohn. J. H. et al. Journal of Bacteriology 1996, vol. 178 (15), p. 4420-4428
van Leeuwen, J. et al., Cold Spring Harb Protoc 2015 (9):pdb.prot085100
Vina-Gonzalez, J. et al., J Vis Exp JoVE; 2016; (110): e53761
Vogl, T. et al., Microb Cell Fact. 2015 Jul. 14; 14:103
Vogl, T., and Glieder, A. N Biotechnol. 2013 May 25; 30(4):385-404
Vogl, T. et al., ACS Synth. Biol., 2014, 3 (3), pp 188-191
Volckaert et al. Mol. Mar. Biol. Biotechnol. 1994 3:57-69.
Weis, R. et al., FEMS Yeast Res. 2004 November; 5(2):179-89
Wiedner, R. et al., Computational and Structural Biotechnology Journal, 2014, 10(16), 58-62.
Yurimoto, H. et al., Bioscience Biotechnology Biochemistry 2001, vol. 65 (3), p. 627-633

The invention claimed is:

1. A host cell of the genus *Pichia* having an episomal plasmid, wherein the episomal plasmid comprises an autonomously replicating sequence (ARS) and an expression cassette comprising a recombinant gene of interest (GOI), and wherein the ARS is positioned on said plasmid outside of said expression cassette and comprises a nucleotide sequence selected from the group consisting of SEQ ID NO:5-11.

2. The host cell of claim 1, wherein the episomal plasmid further comprises a selection marker and wherein the selection marker provides the host cell with a trait selected from the group consisting of auxotrophy and chemical resistance.

3. The host cell of claim 2, wherein the trait is selected from the group consisting of glycerol utilization, sucrose utilization, inulin utilization, cellobiose utilization, amino acid auxotrophy, thymidine auxotrophy, nitrogen source utilization, resistance to fluoracetamide, resistance to deoxyglucose, resistance an antibiotics, and resistance to a gene encoding a toxin.

4. The host cell of claim 1, wherein the episomal plasmid comprises a promoter which is operably linked to the GOI.

5. The host cell of claim 4, wherein the promoter is a regulatable or constitutive promoter of *Pichia pastoris* selected from the group consisting of alcohol oxidase 1 promoter (AOX1), glyceraldehydes-3-phosphate dehydrogenase promoter (GAP), alcohol oxidase promoter (AOD), alcohol oxidase 2 promoter (AOX2), dihydroxyacetone synthase 1 promoter (DAS1), dihydroxyacetone synthase 2 promoter (DAS2), enolase 1 promoter (ENO1), formaldehyde dehydrogenase 1 promoter (FLD1), formate dehydrogenase 1 promoter (FMD), glycerate phosphomutase 1 promoter (GPM1), heat shock protein 82 promoter (HSP82), isocitrate lyase 1 promoter (ICL1), acetohydroxyacid reductoisomerase promoter (ILV5), karyogamy 2 promoter (KAR2), kexin 2 promoter (KEX2), ADP, ATP carrier protein 2 promoter (PETS), peroxisomal biogenesis factor 8 promoter (PEX8), 3-phosphoglycerate kinase 1 promoter (PGK1), phosphate-responsive promoter/nuclear shuttle protein promoter (PHO89/NSP), stress-seventy subfamily A promoter (SSA4), translational elongation factor 1 promoter (TEF1), thiamine repressible promoter (THI11), triosephosphate isomerase 1 promoter (TPI1), GTP-binding protein promoter (YPT1), GTP binding protein 1 promoter (GTH1), GCW14 promoter (GCW14), and glycerol kinase promoter (GUT1).

6. The host cell of claim 4, wherein the promoter comprises the nucleotide sequence of SEQ ID NO:4.

7. The host cell of claim 1, wherein the episomal plasmid is produced in a host cell by a method comprising the steps of:
 (i) providing a linear vector backbone comprising recombination sites at its 5' and 3' ends and the ARS;
 (ii) providing a vector insert comprising a GOI and 5' and 3' homologous sequences which are homologous to the recombination sites; and
 (iii) introducing the linear vector backbone and the vector insert into the host cell and recombining the vector insert with the recombination sites by homologous recombination, thereby producing the episomal plasmid comprising the GOI.

8. The host cell of claim 7, wherein the linear vector backbone and the insert are introduced into the host cell at a molar ratio of between 1:1 and 1:10.

9. The host cell of claim 7, wherein the vector backbone further comprises a selection marker and wherein the selection marker provides the host cell with a trait selected from the group consisting of auxotrophy and chemical resistance.

10. The host cell of claim 9, wherein the trait is selected from the group consisting of glycerol utilization, sucrose utilization, inulin utilization, cellobiose utilization, amino acid auxotrophy, thymidine auxotrophy, nitrogen source utilization, resistance to fluoracetamide, resistance to deoxyglucose, resistance to an antibiotic, and resistance to a gene encoding a toxin.

11. The host cell of claim 1, wherein the host cell is a strain of *Pichia pastoris*.

12. A method of producing a protein of interest (POI) that is encoded by the GOI of the episomal plasmid of claim 1, comprising the step of cultivating the host cell of claim 1 under conditions to express said GOI, thereby producing the POI.

* * * * *